US010969380B2

(12) United States Patent
Perfettini et al.

(10) Patent No.: US 10,969,380 B2
(45) Date of Patent: Apr. 6, 2021

(54) SIMULTANEOUS DETECTION OF CANNIBALISM AND SENESCENCE AS PROGNOSTIC MARKER FOR CANCER

(71) Applicant: Institut Gustave-Roussy, Villejuif (FR)

(72) Inventors: Jean-Luc Perfettini, Meaux (FR); Guido Kroemer, Paris (FR); Eric Deutsch, Paris (FR)

(73) Assignee: Institut Gustave Roussy, Villejuif (FR)

( * ) Notice: Subject to any disclaimer, the term of this patent is extended or adjusted under 35 U.S.C. 154(b) by 37 days.

(21) Appl. No.: 15/642,273

(22) Filed: Jul. 5, 2017

(65) Prior Publication Data

US 2017/0363613 A1 Dec. 21, 2017

Related U.S. Application Data

(62) Division of application No. 14/412,571, filed as application No. PCT/EP2013/064408 on Jul. 8, 2013, now Pat. No. 9,726,661.

(60) Provisional application No. 61/668,775, filed on Jul. 6, 2012.

(51) Int. Cl.
| | |
|---|---|
| *G01N 33/50* | (2006.01) |
| *G01N 33/566* | (2006.01) |
| *G01N 33/68* | (2006.01) |
| *C12N 15/113* | (2010.01) |
| *C12Q 1/6881* | (2018.01) |
| *C12Q 1/6886* | (2018.01) |
| *G01N 33/574* | (2006.01) |

(52) U.S. Cl.
CPC ........ *G01N 33/5011* (2013.01); *C12N 15/113* (2013.01); *C12N 15/1135* (2013.01); *C12Q 1/6881* (2013.01); *C12Q 1/6886* (2013.01); *G01N 33/566* (2013.01); *G01N 33/574* (2013.01); *G01N 33/57496* (2013.01); *G01N 33/6872* (2013.01); *C12N 2310/14* (2013.01); *C12N 2310/141* (2013.01); *C12Q 2600/106* (2013.01); *C12Q 2600/136* (2013.01); *C12Q 2600/156* (2013.01); *G01N 2800/52* (2013.01)

(58) Field of Classification Search
CPC ............................... C12N 15/113; G01N 33/50
USPC ........................................................ 435/7.23
See application file for complete search history.

(56) References Cited

U.S. PATENT DOCUMENTS

2005/0215497 A1    9/2005 Harel-Bellan et al.

FOREIGN PATENT DOCUMENTS

| EP | 2272979 A1 | 1/2011 |
|---|---|---|
| WO | 2005100990 A2 | 10/2005 |
| WO | 2006078774 A2 | 7/2006 |
| WO | 2009064590 A3 | 9/2009 |
| WO | 2010083880 A1 | 7/2010 |
| WO | 2011131472 A1 | 10/2011 |
| WO | 2013079215 A1 | 6/2013 |
| WO | 2013130791 A1 | 9/2013 |
| WO | 2013009979 A3 | 5/2014 |

OTHER PUBLICATIONS

Bourdon et al (Genes & Development, 2005, 19: 2122-2137).*
Marcel et al (Cell Death and Differentiation, 2012, 19: 816-826).*
Koch et al (Cell Oncol, 2012, 35: 243-257).*
Chae et al (Jpn J Clin Oncol, 2009, 39(4): 217-224).*
Thor et al (J Natl Cancer Inst, 1992, 84(11): Abstract).*
Thompson et al (Br J Cancer, 1990, 61: 74-78).*
Abdueva et al (Journal of Molecular Diagnostics, 2010, 12(4): 409-417).*
Vanaja et al (Clin Cancer Res, 2006, 12(4): 1128-1136).*
Li etal (PLOSONE, 2015, 10(7): e0133165, 1-15).*
Xie et al (Clin Cancer Res, 2011, 17(17): 5705-5714).*
de Cremoux et al (BMC Cancer, 2011, 11(215): 1-10).*
Bigelow et al (Breast Cancer Res Treat, 2009, 117:31-44).*
Burdick et al (Carcinogenesis, 2006, 27(11): 2331-2340).*
Ostrakhovitch et al (Journ of Cell Biochem, 2005, 95: 1120-1134).*
Zaparte etal (Eur J Pharmacol, 2020, Abstract).*
Eun et al (Oncology Reports, 2015, 34: 195-202).*
Chang et al (Oncogene, 2005, 24: 714-723).*
Campisi et al., "Cellular senescence: when bad things happen to good cells," Nature Reviews, vol. 8, pp. 729-740, Sep. 2007.
Collado et al., "Cellular Senescence in Cancer and Aging," Cell, vol. 130, pp. 223-233, Jul. 2007.
Janicke et al., "The dark side of a tumor suppressor: anti-apoptotic p53," Cell Death and Differentiation, vol. 15, pp. 959-976, 2008.
Arthur et al: "Autophagic cell death, polyploidy and senescence induced in breast tumor cells by the substituted pyrrole JG-03-14, a novel microtubule poison", Biochemical Pharmacology, vol. 74, pp. 981-991, Oct. 1, 2007.
Bagchi S et al.. "The P2Y2 nucleotide receptor interacts with alphav integrins to activate Go and induce cell migration," J Biol Chem. Nov. 25, 2005;280(47):39050-7.
Bensaad et al., "A p53-inducible regulator of glycolysis and apoptosis," Cell, Jul. 14, 2006;126(1):107-20.

(Continued)

*Primary Examiner* — Sean E Aeder
(74) *Attorney, Agent, or Firm* — Rouget F Henschel; Potomac Law Group, PLLC

(57) ABSTRACT

The present inventors show that cannibal cells can undergo senescence after entosis in vivo and that the tumor suppressive protein p53 act as a repressor of this phenomenon. They therefore propose new tools to study the molecular pathways involved in the cannibalism process, for example by measuring the expression levels of p53 or splice variants thereof (such as Δ133TP53, TP53β, TP53γ or Δ40TP53), the release of extracellular ATP or purinergic P2Y2 receptor activity. The present inventors also demonstrated that the detection of senescent cannibal cells in breast adenocarcinoma obtained from patients treated with neo-adjuvant therapy positively correlates with good patient's response to treatment. Altogether, these results provide the first evidence that detection of cellular cannibalism and senescence simultaneously in tumors helps for the diagnosis of disease outcomes and for the prediction of treatment efficiency against cancer diseases.

15 Claims, 15 Drawing Sheets

Figure 1:
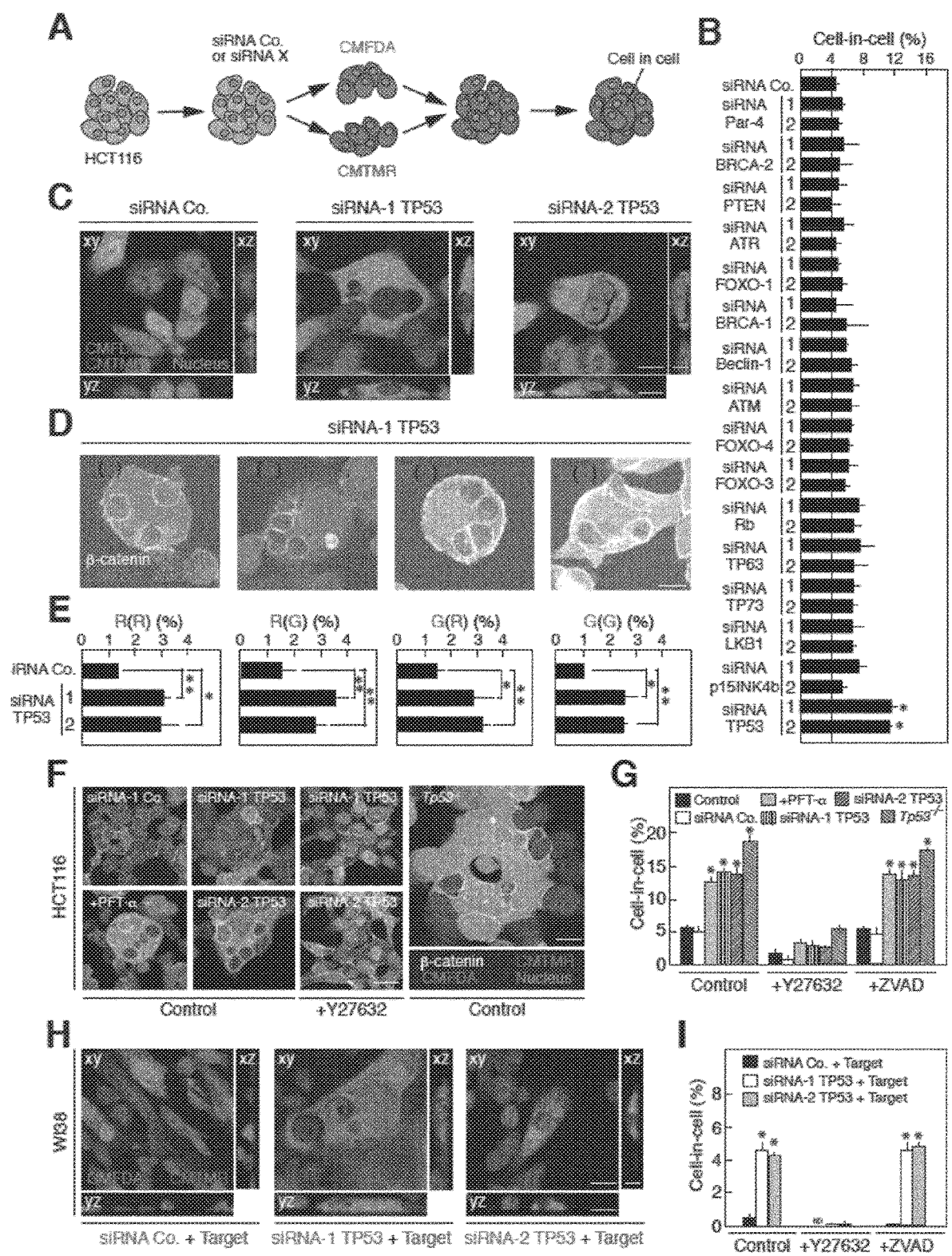

Specification includes a Sequence Listing.

(56) References Cited

OTHER PUBLICATIONS

Bourdon JC. "p53 and its isoforms in cancer," Br J Cancer. Aug. 6, 2007;97(3):277-82.
Brummelkamp et al., "A System for Stable Expression of Short Interfering RNAs in Mammalian Cells," Science, vol. 296, pp. 550-553, Apr. 2002.
Burnstock G, "Purine and pyrimidine receptors," Cell Mol Life Sci. Jun. 2007;64(12):1471-83.
Cano et al., "Homotypic cell cannibalism, a cell-death process regulated by the nuclear protein 1, opposes to metastasis in pancreatic cancer," EMBO Mol Med. Sep. 2012;4(9):964-79.
Cartier-Michaud et al., "G.Matrix-bound PAI-1 supports cell blebbing via RhoA/ROCK1 signaling. PLoS One," 2012;7(2) :e32204.
Chekeni et al., "Pannexin 1 channels mediate 'find-me' signal release and membrane permeability during apoptosis," Nature. Oct. 14, 2010; 467(7317): 863-867.
Chen et al. "ATP release guides neutrophil chemotaxis via P2Y2 and A3 receptors," Science. Dec. 15, 2006;314 (5806):1792-5.
Chevallier et al., "A prognostic score in histological node negative breast cancer," Br J Cancer. Mar. 1990; 61 (3): 436-440.
Coppé et al., "Senescence-Associated Secretory Phenotypes Reveal Cell-Nonautonomous Functions of Oncogenic RAS and the p53 Tumor Suppressor," PLoS Biol. Dec. 2008; 6(12): e301.
Corriden et al., , Basal Release of ATP: An Autocrine-Paracrine Mechanism for Cell Regulation. Sci Signal. Jan. 12, 2010; 3(104): re1.
Demidenko, Z.N. et al."Paradoxical suppression of cellular senescence by p53," Proc Natl Acad Sci U S A. May 25, 2010; 107(21): 9660-9664.
Di et al: "Apoptosis, autophagy, accelerated senescence and reactive oxygen in the response of human breast tumor cells to Adriamycin", Biochemical Pharmacology, vol. 77, pp. 1139-1150, Apr. 1, 2009.
Elliott et al: "Nucleotides released by apoptotic cells act as a find-me signal to promote phagocytic clearance", Nature, vol. 461, pp. 282-287, Sep. 10, 2009.
Fasanaro et al, "microRNA: Emerging therapeutic targets in acute ischemic diseases," Pharmacol. Ther. 2010; 125 (1):92-104.
Florey et al., "Autophagy machinery mediates macroendocytic processing and entotic cell death by targeting single membranes," Nat Cell Biol. Oct. 16, 2011; 13(11): 1335-1343.
Florey et al., "Autophagy proteins in macroendocytic engulfment," Trends Cell Biol. Jul. 2012; 22(7): 374-380.
Fujita et al., "p53 isoforms, Δ133p53 and p53β, are endogenous regulators of replicative cellular senescence," Nat Cell Biol. Sep. 2009; 11(9): 1135-1142.
Gadea et al., "Loss of p53 promotes RhoA-ROCK-dependent cell migration and invasion in 3D matrices" J Cell Biol. Jul. 2, 2007; 178(1): 23-30.
Gadéa et al., "Regulation of Cdc42-mediated morphological effects: a novel function for p53," EMBO J. May 15, 2002;21(10):2373-82.
Garanina et al., "Stages of Cell Cannibalism—Etosis—in Normal Human Keratinocyte Culture," Biochemistry, vol. 80, No. 11, pp. 1469-1477, 2015.
González-Pastor et al., "Cannibalism by sporulating bacteria," Science. Jul. 25, 2003;301(5632):510-3.
Gottlieb et al., "p53 regulation of metabolic pathways," Cold Spring Harb., Perspect Biol. Apr. 2010;2(4):a001040.
Grimsley et al., "Cues for apoptotic cell engulfment: eat-me, don't eat-me and come-get-me signals," Trends Cell Biol. Dec. 2003;13(12):648-56.
Guiral et al., "Competence-programmed predation of noncompetent cells in the human pathogen *Streptococcus pneumoniae*: genetic requirements," Proc Natl Acad Sci U S A. Jun. 14, 2005;102(24):8710-5.
Guo et al., "p19Arf-p53 tumor suppressor pathway regulates cell motility by suppression of phosphoinositide 3-kinase and Rac1 GTPase activities," Biol Chem. Apr. 18, 2003;278(16):14414-9.
Ha et al., "ARF functions as a melanoma tumor suppressor by inducing p53-independent senescence," Proc Natl Acad Sci U S A. Jun. 26, 2007;104(26):10968-73.

Ha et al., "Melanomagenesis: overcoming the barrier of melanocyte senescence," Cell Cycle, Jul. 1, 2008;7(13):1944-8.
Hanahan et al., "Hallmarks of cancer: the next generation," Cell. Mar. 4, 2011;144(5):646-74.
Hanahan et al., "The Hallmarks of Cancer," Cell. Jan. 7, 2000;100(1):57-70.
Hopfner et al: "Growth inhibition and apoptosis induced by P2Y 2 receptors in human colorectal carcinoma cells: involvement of intracellular calcium and cyclic adenosine monophosphate", International Journal of Colorectal Disease, vol. 16, pp. 154-166, Jun. 1, 2001.
International Search Report issued in application No. PCT/EP2013/064408 dated Dec. 16, 2013.
Kaghad et al., "Monoallelically expressed gene related to p53 at 1p36, a region frequently deleted in neuroblastoma and other human cancers," Cell, Aug. 22, 1997;90(4):809-19.
Kamb et al., "Analysis of the p16 gene (CDKN2) as a candidate for the chromosome 9p melanoma susceptibility locus," Nat Genet. Sep. 1994; 8(1):23-6.
Khoury et al., "The isoforms of the p53 protein," Cold Spring Harb Perspect Biol. Mar. 2010;2(3):a000927.
Krajcovic et al., "A non-genetic route to aneuploidy in human cancers," Nat Cell Biol. Mar. 2011;13(3):324-30.
Krajcovic et al., "Mechanisms of ploidy increase in human cancers: a new role for cell cannibalism," Cancer Res. Apr. 1, 2012;72(7):1596-601.
Kuilman et al., "The essence of senescence," Genes Dev. Nov. 15;24(22):2463-79.
Lai et al., "Silencing the Metallothionein-2A Gene Induces Entosis in Adherent MCF-7 Breast Cancer Cells," The Anatomical Record, vol. 293, pp. 1685-1691, 2010.
Laurence Zitvogel et al: "Inflammasomes in carcinogenesis and anticancer immune responses", Nature Immunology, vol. 13, No. 4, pp. 343-351, Apr. 1, 2012.
Le et al., "MicroRNA-125b is a novel negative regulator of p53," Genes and Development, vol. 23, pp. 862-876, 2009.
Lefort et al., "Notch1 is a p53 target gene involved in human keratinocyte tumor suppression through negative regulation of ROCK1/2 and MRCKalpha kinases," Genes Dev. Mar. 1, 2007;21(5):562-77.
Li et al, "Therapeutic MicroRNA Strategies in Human Cancer," AAPSJ, 2009; 11(4):747-757.
Li et al, "Engulfment is required for cell competition," Cell. Jun. 15, 2007;129(6):1215-25.
Liao et al, "The P2Y2 nucleotide receptor requires interaction with alpha v integrins to access and activate G12," J Cell Sci. May 1, 2007;120(Pt 9):1654-62.
Lin et al., "Skp2 targeting suppresses tumorigenesis by Arf-p53-independent cellular senescence," Nature. Mar. 18, 2010;464(7287):374-9.
Liu et al., "Src homology 3 binding sites in the P2Y2 nucleotide receptor interact with Src and regulate activities of Src, proline-rich tyrosine kinase 2, and growth factor receptors," J Biol Chem. Feb. 27, 2004;279(9):8212-8.
Lowe et al., "Intrinsic tumour suppression," Nature 432, 307-315 (2004).
Lugini et al., "Cannibalism of Live Lymphocytes by Human Metastatic but Not Primary Melanoma Cells," Cancer Research, vol. 66, No. 7, 2006, pp. 3629-3638.
Lukas et al., "53BP1 nuclear bodies form around DNA lesions generated by mitotic transmission of chromosomes under replication stress," Nat Cell Biol. Mar. 2011;13(3):243-53.
Malorni et al., "Reno-Cannibalism: A Survival 'Escamotage'", Autophagy, vol. 3, No. 1, 2007, pp. 75-77.
Martins et al: "Chemotherapy induces ATP release from tumor cells", Cell Cycle, vol. 8, Issue 22, pp. 3723-3728, Nov. 15, 2009.
Mathew et al: "Role of autophagy in cancer", Nature Reviews, Cancer, vol. 7, pp. 961-967 Dec. 1, 2007.
Matsuura et al., "Senescent phenotypes of skin fibroblasts from patients with Tangier disease." Biochem Biophys Res Commun. Jun. 1, 2007;357(2):493-8. Epub Apr. 9, 2007.

(56) References Cited

OTHER PUBLICATIONS

Mormone et al., "Genotype-dependent priming to self- and xeno-cannibalism in heterozygous and homozygous lymphoblasts from patients with Huntington's disease," Journal of Neurochemistry, vol. 98, 2006, pp. 1090-1099.
Nardella et al, "Pro-senescence therapy for cancer treatment," Nature Reviews, vol. 11, pp. 503-510, Jul. 2011.
Notice of Allowance for U.S. Appl. No. 14/412,571 dated Apr. 5, 2017.
Office Action for U.S. Appl. No. 14/412,571 dated Dec. 18, 2015.
Office Action for U.S. Appl. No. 14/412,571 dated Sep. 21, 2016.
Ostrakhovitch et al., "Basal and copper-induced expression of metallothionein isoform 1,2 and 3 genes in epithelial cancer cells: The role of tumor suppressor p53," Journal of Trace Elements in Medicine and Biology, vol. 35, pp. 18-29, 2016.
Overholtzer et al. "The cell biology of cell-in-cell structures," Nature reviews Molecular cell biology 9, 796-809. (2008).
Overholtzer et al., "A nonapoptotic cell death process, entosis, that occurs by cell-in-cell invasion," Cell, 2007, vol. 131, 966-979.
Paoletti et al., "Multfaceted roles of purinergic receptors in viral infection," Microbes and Infection, vol. 14, pp. 1278-1283, 2012.
Parr "Cloning and Expression of a human P2u nucleotide receptor, a target for cystic fibrosis pharmacology," PNAS 91(8):3275-9, 1994 (correction).
Rivetti Di Val Cervo et al., "p63-microRNA feedback in Keratinocyte senescence," Proc Natl Acad Sci U S A. Jan. 24, 2012;109(4):1133-8.
Roger et al., "Control of cell migration: a tumour suppressor function for p53?," Bio. Cell 98, 141-152, 2006.
Ru et al., "The dark side of a tumor suppressor: anti-apoptotic p53," Cell Death Differ. Jun. 2008;15(6):959-76.
Sablina et al., "The antioxidant function of the p53 tumor suppressor," Nature Medicine 11, 1306-1313, Dec. 2005.
Sabuna et al., "Tumor suppressor p53 and its homologue p73alpha affect cell migration," The Journal of Biological Chemistry 278, 27362-27371, Jul. 25, 2003.
Schmitt, C.A., "Senescence, apoptosis and therapy—cutting the lifelines of cancer," Nature Reviews Cancer 3, 286-295, Apr. 2003.
Seror, C. et al, "Extracelluar ATP acts on P2Y2 purinergic receptors to facilitate HIV-1 infection," The Journal of Experimental Medicine, vol. 208, No. 9, 2011.
Sharma et al., "Cell Cannibalism and Cancer," Diagnostic Cytopathology, vol. 39, No. 3, 2010, pp. 229-233.
Shen et al., "Gene silencing by adenovirus-delivered siRNA," FEBS Letters, vol. 539, pp. 111-114, 2003.
Tamajusuku et al: "Characterization of ATP-induced cell death in the GL261 mouse glioma", Journal of Cellular. Biochemistry, vol. 109, pp. 983-991, Jan. 12, 2010.
Tasdemir et al., "Regulation of autophagy by cytoplasmic p53," Nature Cell Biology, vol. 10, No. 6, pp. 676-687, S1-S7, Jun. 2008.
Teodoro et al., "Inhibition of tumor angiogenesis by p53: a new role for the guardian of the genome," J. Mol. Med., vol. 85, pp. 1175-1186, 2007.
Tinari et al., "Hyperphagia by self- and xeno-cannibalism: Cell death by indigestion? A reminiscence of the Phedrus Fabula 'Rana Rupta et Bos'?", Autophagy, vol. 4, No. 1, 2008, pp. 128-130.
Tolstonog et al., "Metabolic sensing by p53: keeping the balance between life and death," Proceedings of the National Academy of Sciences of the United States of America 107, 13193-13194, Jul. 27, 2010.
Trautmann, "Extracellular ATP in the Immune System: More than just a "Danger Signal"," Science Signaling, vol. 2, Issue 56, Feb. 3, 2009.
Vogelstein et al., "Surfing the p53 network," Nature 408, 307-310, Nov. 16, 2000.
Vousden et al., "Blinded by the Light: The Growing Complexity of p53," Cell 137, 413-431, May 1, 2009.
Vousden et al., "Live or let die: the cell's response to p53," Nature Reviews Cancer 2. 594-604, Aug. 2002.
Vousden et al., "p53 in health and disease," Nature Reviews Molecular Cell Biology 8, 275-283.
Waddell et al., "Breakdown of self/nonself recognition in cannibalistic strains of the predatory slime mold, Dictyostelium caveatum," The Journal of Cell Biology 102, 298-305, Jan. 1986.
Wei et al., "p53 Family: Role of Protein Isoforms in Human Cancer," vol. 2012, pp. 1-19, Oct. 2011.
Xia et al., "Tumor suppressor p53 restricts Ras stimulation of RhoA and cancer cell motility," Nature Structural & Molecular Biology 14, 215-223, Mar. 2007.
Yang et al., "p63, a p53 homolog at 3q27-29, encodes multiple products with transactivating, death-inducing, and dominant-negative activities," Mol Cell. Sep. 1998; 2(3):305-16.
Yonish-Rouach et al., "Wild-type p53 induces apoptosis of myeloid leukaemic cells that is inhibited by interleukin-6," Nature 352, 345-347, Jul. 25, 1991.
Young et al: "Autophagy mediates the mitotic senescence transition", Genes & Development, vol. 23, pp. 798-803, Apr. 1, 2009.
Shi et al., "Regulation of Interleukin-8 Expression by Tumor-Associated Stress Factors," Journal of Interferon and Cytokine Research, vol. 21, pp. 553-566, 2001.
Erb et al., "Coupling of P2Y receptors to G proteins and other signaling pathways," WIREs Membr. Transp. Signal, vol. 1, pp. 789-803, Nov./Dec. 2012.
Liao et al., "The P2Y2 nucleotide receptor requires interaction with av integrins to access and activate G12," J. Cell Sci., vol. 120, Pt 9, pp. 1654-1662, May 2007.

\* cited by examiner

SIMULTANEOUS DETECTION OF CANNIBALISM AND SENESCENCE AS PROGNOSTIC MARKER FOR CANCER

This application is a divisional of U.S. patent application Ser. No. 14/412,571, filed Jan. 2, 2015, now U.S. Pat. No. 9,726,661, which is a U.S. National Stage of PCT/EP2013/064408, filed Jul. 8, 2013, which claims priority to U.S. Provisional Application No. 61/668,775, filed Jul. 6, 2012, all of which are incorporated herein in their entirety by reference.

SUMMARY OF THE INVENTION

The present inventors show that cannibal cells can undergo senescence after entosis in vivo and that the tumor suppressive protein p53 act as a repressor of this phenomenon. They therefore propose new tools to study the molecular pathways involved in the cannibalism process, for example by measuring the expression levels of p53 or splice variants thereof (such as Δ133TP53, TP53β, TP53γ or Δ40TP53), the release of extracellular ATP or purinergic P2Y2 receptor activity. The present inventors also demonstrated that the detection of senescent cannibal cells in breast adenocarcinoma obtained from patients treated with neo-adjuvant therapy positively correlates with good patient's response to treatment. Altogether, these results provide the first evidence that detection of cellular cannibalism and senescence simultaneously in tumors helps for the diagnosis of disease outcomes and for the prediction of treatment efficiency against cancer diseases.

BACKGROUND OF THE INVENTION

Cannibalism constitutes a consumption strategy used by micro- and higher organisms to adapt to environmental stresses and to survive. Gram positive species, *Bacillus subtilis* and *Streptococcus pneumonia* exert cannibalistic activities during the early stages of sporulation (Gonzalez-Pastor et al., *Science* 2003) or during natural genetic transformation (Guiral et al., *PNAS* 2005). In contrast, the slime molde *Dictyostelium caveatum* represses its predatory abilities during its quasi-multicellular differentiation stage (Waddell and Duffy, *The Journal of cell biology* 1986). In *Drosophila*, studies on genetic mosaics that place cells in competition within tissues unrevealed that cannibalism is a genetically controlled process that may occur at the single cell level and actively participates to cell competition during tissue repair and tumor development (Li and Baker, *Cell* 2007). Although cellular cannibalism is poorly reported in physiological situations, cannibal cells have been frequently detected in various human tumor types such as melanoma, leukemia and cervical carcinoma, colon carcinoma, stomach carcinoma, liver carcinoma adenocarcinoma and in metastatic breast carcinoma (Overholtzer and Brugge, *Nature reviews Molecular cell biology* 2008).

On a one hand, cellular cannibalism was suggested to cause the destruction of cancer cells by other malignant cells by entosis. In contrast to oilier (apoptotic, necrotic or autophagic) cell death forms that are controlled in a cell-autonomous fashion, entosis (from the Greek word entos, which means inside, into, or within) requires the internalization of a live target cancer cell by a live <<cannibal >> cancer cell (Overholtzer and Brugge, *Nature reviews Molecular cell biology* 2008). An inverse correlation between entosis and metastasis appearance in human pancreatic adenocarcinoma was furthermore reported, suggesting that this atypical death process may represent intrinsic tumor suppression mechanism (Cana et al., *EMBO Mol Med.* 2012).

On another hand, cellular cannibalism was shown to provoke the polyploidization of the engulfing cell by disrupting cytokinesis, and hence to promote oncogenesis indirectly, by generating polyploid cells that tend to generate aneuploidy daughter cells (Krajcovic et al., *Nat. Cell Biol.* 2011; Krajcovic and Overholtzer, *Cancer Res.* 2012).

As a consequence of (homotypic or heterotypic) interactions between cancer cells or between cancer cells and other (stromal or immune) cells, cannibalism could have—depending on the genetic status of cancer cells (target and cannibal cells) and on tumor microenvironment—variable consequences on tumor growth and disease outcomes.

Although the "cell-in-cell" cytological features have been widely reported in human tumors, the molecular and cellular bases of cellular cannibalism remain unknown.

In this context, the present inventors provide evidence that TP53 and, more specifically, Δ133TP53, acts as repressors of cellular cannibalism. Their results also unrevealed that cellular cannibalism is functionally connected to senescence, both in vitro (in cellular models of senescence) and in vivo (in human breast carcinoma), where they may influence the efficiency of a chemotherapeutic treatment.

FIGURE LEGENDS

FIG. 1. Identification of TP53 as repressor of cellular cannibalism. (A) Schematic representation of experimental procedure used to evaluate the ability to tumor suppressive depletion to enhance cell in cell internalization. (B) Frequencies of cell-in-cell structures induced by depletion of tumor suppressive proteins in HCT116. After 48 hours of transfection indicated siRNA, colorectal HCT116 cells were stained with CMTMR and CMFDA cell trachers, mixed and cultured during 24 hours. Quantification of cell-in-cell structures induced by depletions of tumor suppressor proteins was realized by confocal microscopy. The frequencies of cell-in-cell structures were determined for at least 300 cells in 3 independent experiments (mean+/−s.e.m, p<0.001). (C) Detection of cell-in-cell structures induced by depletion of TP53, as visualized by confocal microscopy. Inserts represent xz and yz optical sections and show that after p53 depletion, red CMTR labeled HCT116 cells are internalized by green CMFDA labeled HCT116 cells. Representative micrographs of xy (scale bar, 5 µm), xz (scale bar, 4 µm) and yz (scale bar, 1 µm) optical sections are shown. Images are representative of at least four independent experiments. (D) Representative micrographs of cell-in-cell structures showing that after depletion of TP53 by two specific siRNAs, (red) CMTR labeled HCT116 cells internalized (red) CMTR labeled HCT116 cells (noted R(R)) or (green) CMFDA labeled HCT116 cells (noted R(G)), and (green) CMFDA labeled HCT116 cells engulfed (red) CMTR labeled HCT116 cells (noted G(R)) or (green) CMFDA labeled HCT116 cells (noted G(G)) (scale, 5 µm). (E) Frequencies of cell-in-cell structures showing R(R), R(G), G(R) or G(G) cell internalization detected after depletion of TP53 by two distinct siRNAs (as compare to control). The frequencies of cell-in-cell structures were determined for at least 300 cells in 3 independent experiments (mean+/−s.e.m, p<0.001). (F) Cell-in-cell structures induced by 10 µM PFT-α, TP53 knockdown, or TP53 knockout in HCT116. Cell-in-cell structures were identified by b-catenin (white), CMFDA (green) and CMTMR (red) staining of internalizing HCT116 cells. Images are representative of at least four independent experiments (scale bar in a, 5 μm and scale bar in b 1 μm). (G) Frequencies of cell-in-cell structures induced by 10 μM PFT-α, TP53 knockdown, or TP53 knockout in HCT116 in presence or in absence of 20 μM of ROCK inhibitor (Y27632) or 100 μM of pan-caspase inhibitor (z-VAD). The frequencies of cell-in-cell structures were determined for at least 300 cells in 3 independent experiments (mean+/−s.e.m, p<0.001). (H) Detection of cell-in-cell structures in TP53 depleted human diploid fibroblasts strain WI38, as visualized by confocal microscopy. Inserts represent xz and yz optical sections and show that after TP53 depletion, red CMTR labeled primary WI38 cells are internalized by green CMFDA labeled HCT116 cells. Representative micrographs of xy (scale bar, 5 μm), xz (scale bar, 4 μm) and yz (scale bar, 1 μm) optical sections are shown. Images are representative of at least four independent experiments. (1) Frequencies of cell-in-cell structures induced by depletion of TP53 in human diploid fibroblasts strain WI38. The frequencies of cell-in-cell structures were determined for at least 300 cells in 3 independent experiments (mean+/−s.e.m, p<0.001).

Figure 2:
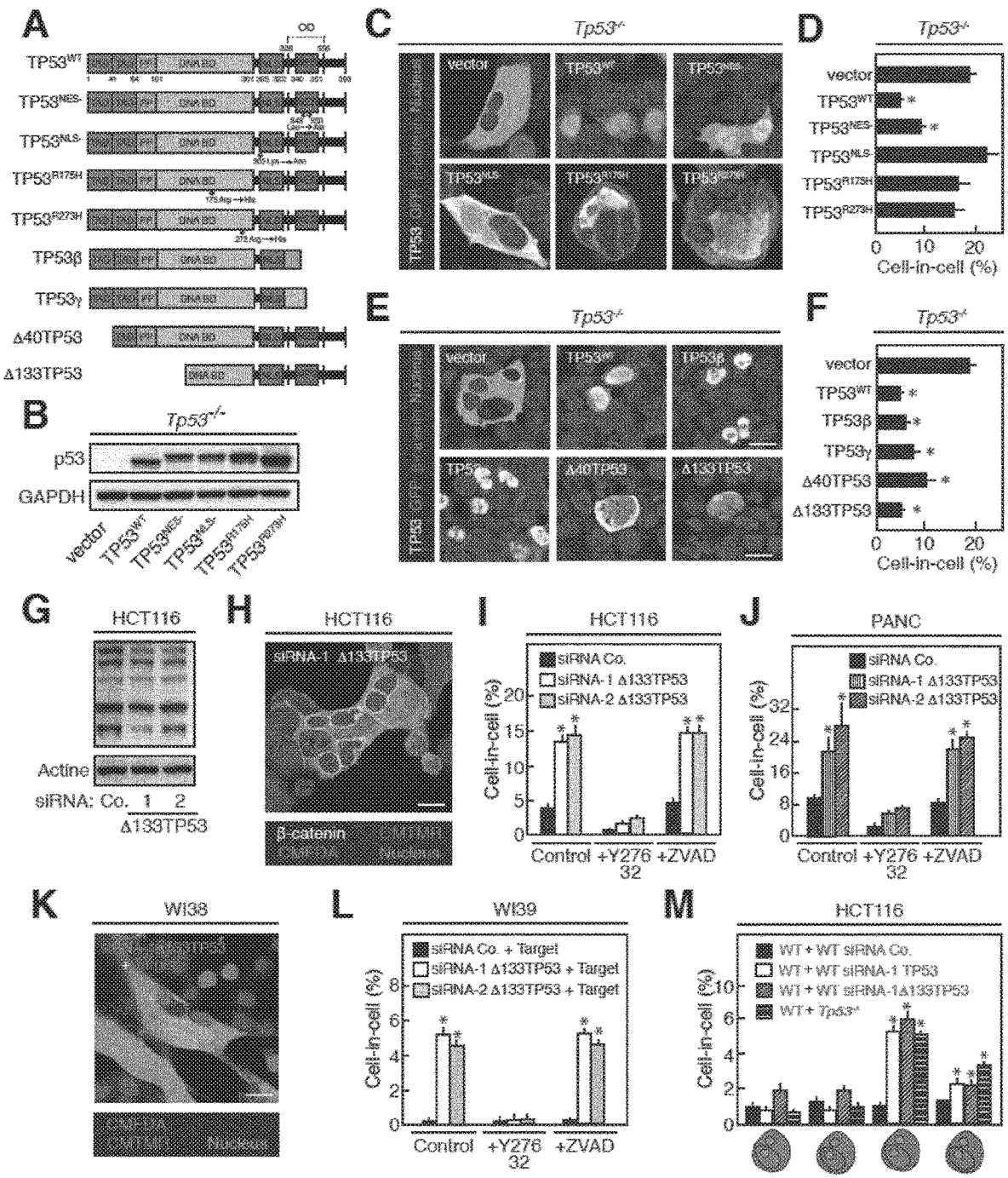

FIG. 2. Δ133TP53 isoform is also a repressor of cellular cannibalism. (A-D) Effects of TP53 mutants and TP53 isoforms on cell-in-cell internalization in Tp53$^{-/-}$ HCT116 cells. Schematic representation of TP53 mutants and isoforms used in this study (A). Expression of TP53 mutants in Tp53$^{-/-}$ HCT116 cells was validated by Western blot. Immunoblot shown is representative of 3 independent experiments (B). Representative micrographs of Tp53$^{-/-}$ transfected with plasmids expressing WI (TP53$^{WT}$), nuclear (TP53$^{NES-}$), cytoplasmic (TP53$^{NLS-}$) or mutated TP53 (TP53$^{R175H}$ and TP53$^{R273H}$) are shown (C). Quantification of cell-in-cell structures of Tp 53$^{-/-}$ cells transiently transfected with TP53 mutants is shown (mean+/−s.e.m, n=3, p<0.001) (D). Micrographs of Tp53$^{-/-}$ cells transfected with plasmids expressing wild type TP53, TP53β, TP53γ, Δ40TP53 or Δ133TP53 isoforms are shown (E). Quantification of cell-in-cell structures of Tp53$^{-/-}$ cells transiently transfected with wild type TP53 or TP53 isoforms (TP53, TP53β, TP53γ, Δ40TP53 or Δ133TP53) is shown (mean+/−s.e.m, n=3, p<0.001) (F). (G-I) Effects of Δ133TP53 depletion on cell-in-cell internalization in HCT116 cells. Depletion of Δ133TP53 in HCT116 cells was validated by Western blot (n=3)(G). Detection of cell-in-cell structures induced by depletion of Δ133TP53 by confocal microscopy. Representative micrographs of xy (scale bar, 5 μm), is shown. Image is representative of at least four independent experiments (K). Frequencies of cell-in-cell structures induced by depiction of Δ133TP53 in human diploid fibroblasts strain WI38. The frequencies of cell-in-cell structures were determined for at least 300 cells in 3 independent experiments (mean+/− s.e.m, p<0.001) (L). Effects of TP53 or Δ133TP53 knockdown and TP53 knock out on cell engulfment. Quantification of cell-in-cell structures obtained after culture of TP53- or Δ133TP53-depleted HCT116 cells (red) with CMFDA labeled HCT116 target cells is shown (mean+/−s.e.m, n=3, p<0.001) (M).

Figure 3:
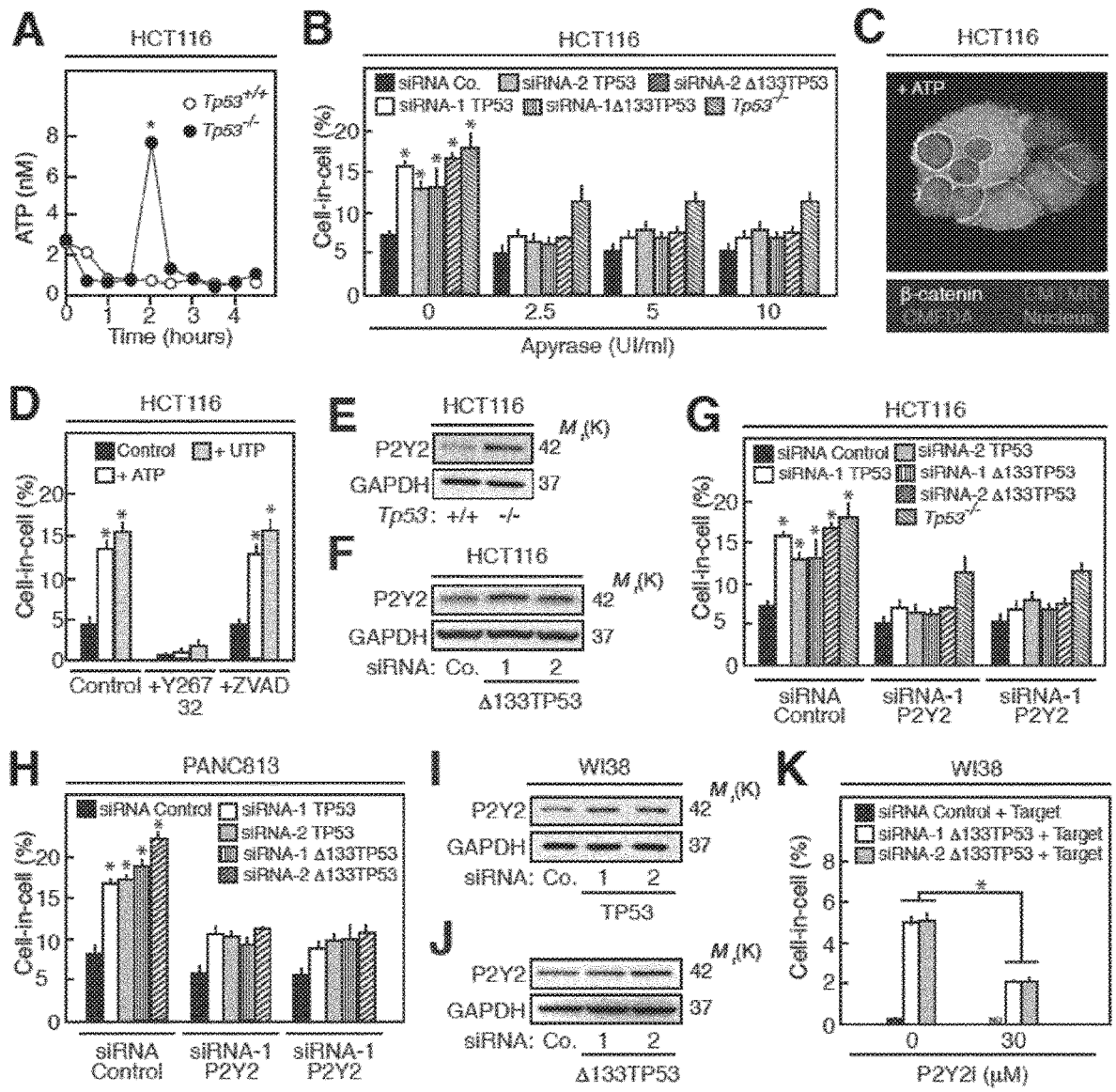

FIG. 3. Extracellular ATP and purinergic receptor P2Y2 participate in cellular cannibalism induced by TP53 or Δ133TP53 depletion. (A) Release of ATP during coculture of Tp53$^{-/-}$ (black circle) or Tp53$^{+/+}$ (white circle) HCT116 cells was determined at different time points by ATP-dependent bioluminescence in 3 independent experiments. One representative experiment is shown (mean±SEM of triplicates; *P <0.01). (B) Effect of apyrase on cellular cannibalism. Cocultures of TP53 or Δ133TP53 depleted HCT116 cells in presence of different concentrations of apyrase were performed. Then, detection of cell-in-cell structures was performed by confocal microscopy (mean+/− s.e.m, n=3, p<0.001). (C,D) Effects of extracellular ATP and UTP on cellular cannibalism. Detection of cell-in-cell structures induced after the supplementation of ATP or UTP on culture of CMFDA and CMTMR labeled HCT116 cells. Representative micrographs are shown (scale bar, 5 μm). Images are representative of at least 3 independent experiments (C). Frequencies of cell-in-cell structures induced by ATP or UTP supplementations in HCT116 in presence or in absence of 20 μM of ROCK inhibitor (Y27632) or of 100 μM pan-caspase inhibitor (zVAD). The frequencies of cell-in-cell structures were determined for at least 300 cells in 3 independent experiments (mean+/−s.e.m, p<0.0011) (D). (E-F) Overexpression of P2Y2 after TP53 or Δ133TP53 depletions on colorectal carcinoma HCT116 cells. Expression was determined by immunoblot. Representative immunoblots of 3 independent experiments are shown. (G,H) Effects of P2Y2 depletion on cellular cannibalism observed after TP53 or Δ133TP53 depletions. As previously described, HCT116 (G) or PANC813 (H) cells that are depleted for P2Y2 and/or inactivated for TP53 or Δ133TP53 were stained, mixed and cultured during 24 hours in presence or in absence of 20 μM of Y27632 or 100 μM of zVAD. The frequencies of cell-in-cell structures were determined for at least 300 cells in 3 independent experiments (mean+/− s.e.m, *p<0.001). (I-J) P2Y2 expression on human primary fibroblasts after TP53 or Δ133TP53 depletions. Expression was determined by immunoblot. Representative immunoblots of 3 independent experiments are shown. (K) Effects of pharmacological inhibition of P2Y2 on cellular cannibalism induced by Δ133TP53 depletion. Human primary fibroblasts that are depleted for Δ133TP53 were stained, mixed and cultured during 24 hours in presence or in absence of the 20 μM of P2Y? inhibitor Kaempferol. The frequencies of cell-in-cell structures were determined for at least 300 cells in 3 independent experiments (mean+/−s.e.m, p<0.001).

Figure 4:
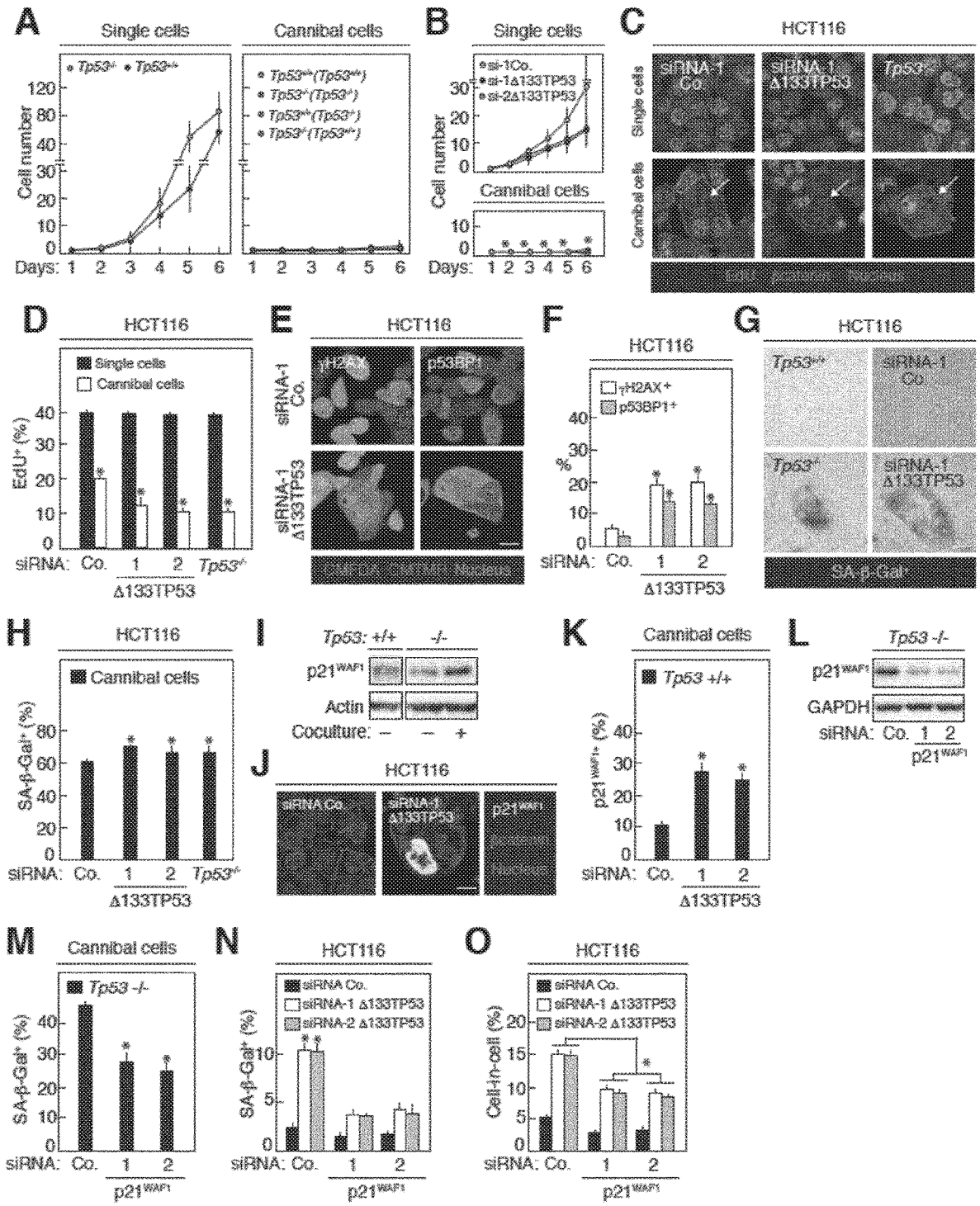

FIG. 4. Cellular cannibalism leads to senescence. (A,B) Effects of cellular cannibalism on cell proliferation. After cell sorting, cell proliferation of TP53 or Δ133TP53 knocked down and TP53 knocked out single or cannibal cells were performed during 6 days. (C-H) Effects of cellular cannibalism on senescence induction. Cannibal cells mediated by TP53 knockout or Δ133TP53 knockdown were examined in EdU incorporation assay (C,D), in DNA damage response (E,F) and in SA-β-Gal assay (G,H). (C) Determination of EdU incorporation on cannibal cells induced by Δ133TP53 knockdown, or TP53 knockout. Cell-in-cell structures were identified by β-catenin (red) and Hoechst 33342 (blue) staining of internalizing HCT116 cells. EdU positive cells are green. Images are representative of at least three independent experiments (scale bar: 5 μm). (D) Determination of EdU incorporation in single and cannibal cells after TP53 or Δ133TP53 inactivation. The number of EdU positive single or cannibal cells per total number of cells examined (at least 300 per well) was recorded. (E) Detection of DNA damage response (DDR) foci in single and cannibal cells after TP53 or Δ133TP53 inactivation. DNA damage response (DDR) foci were identified by γ-H2AX or p53BP1 (White), CMFDA (green), CMTMR (red) and Hoechst 33342 (blue) staining of internalizing HCT116 cells. Images are representative of at least three independent experiments (scale bar: 5 μm). (F) Quantification of DNA damage foci in single and cannibal cells after TP53 or Δ133TP53 inactivation. The percentage of γ-H2AX$^+$ cells or p53BP1$^+$ cells were determined by confocal microscopy. Error bars represent means±SEM (n=3; *P 0.01). Representative pictures of SA-β Gal staining of single and cannibal cells obtained after TP53 or Δ133TP53 inactivation. (H) Summary of SA-β Gal assay. The data are mean±SEM (n=3; *P <0.01). (I) p21$^{WAF1}$ expression during coculture of Tp53$^{+/+}$ or TP53$^{-/-}$ cells, P21$^{WAF1}$ expression was determined by immunoblot. Representative immunoblots of 3 independent experiments are shown. (J) Detection of p21$^{WAF1}$ expression in cannibal cells after Δ133TP53 depletion. Expression of p21$^{WAF1}$ was examined by confocal microscopy using antibodies against p21$^{WAF1}$ (white) or β-catenin (red). Nuclei are stained with Hoechst 33342 (blue). Images are representative of at least three independent experiments (scale bar: 5 μm). (K) Quantification of p21$^{WAF1}$ expression in single and cannibal cells after TP53 or Δ133TP53 inactivation. The percentage of ☐21WAF$^+$ cells in cannibal cells was determined by confocal microscopy. Error bars represent means±SEM (n=3; *P <0.01). (L) Expression of p21$^{WAF1}$ on HCT116 Tp53$^{-/-}$ after knockdown of p21$^{WAF1}$. P21$^{WAF1}$ expression was determined by immunoblot. Representative immunoblots of 3 independent experiments are shown. (M) Effects of p21$^{WAF1}$ depletion on SA-βGal activity of cannibal cells. The number of SA-β Gal positive single or cannibal cells per total number of cells examined (at least 300 per well) was recorded. Error bars represent means±SEM (n=3; *P <0.01). (N) Effects of p21$^{WAF1}$ knockdown on SA-β Gal activity of cannibal cells obtained after TP53 or Δ133TP53 inactivation. Quantification of SA-β Gal positive cells were realized as described above (n=3; means±SEM; *P <0.01). (O) Effects of p21$^{WAF1}$ knockdown on cell-in-cell internalization detected after TP53 or Δ133TP53 inactivation. Cell-in-cell structures were identified by β-catenin (white), CMFDA (green) and CMTMR (red) staining of transfected HCT116 cells. The frequencies of cell-in-cell structures were determined for at least 300 cells in 3 independent experiments (mean+/−s.e.m, p<0.001).

Figure 5:
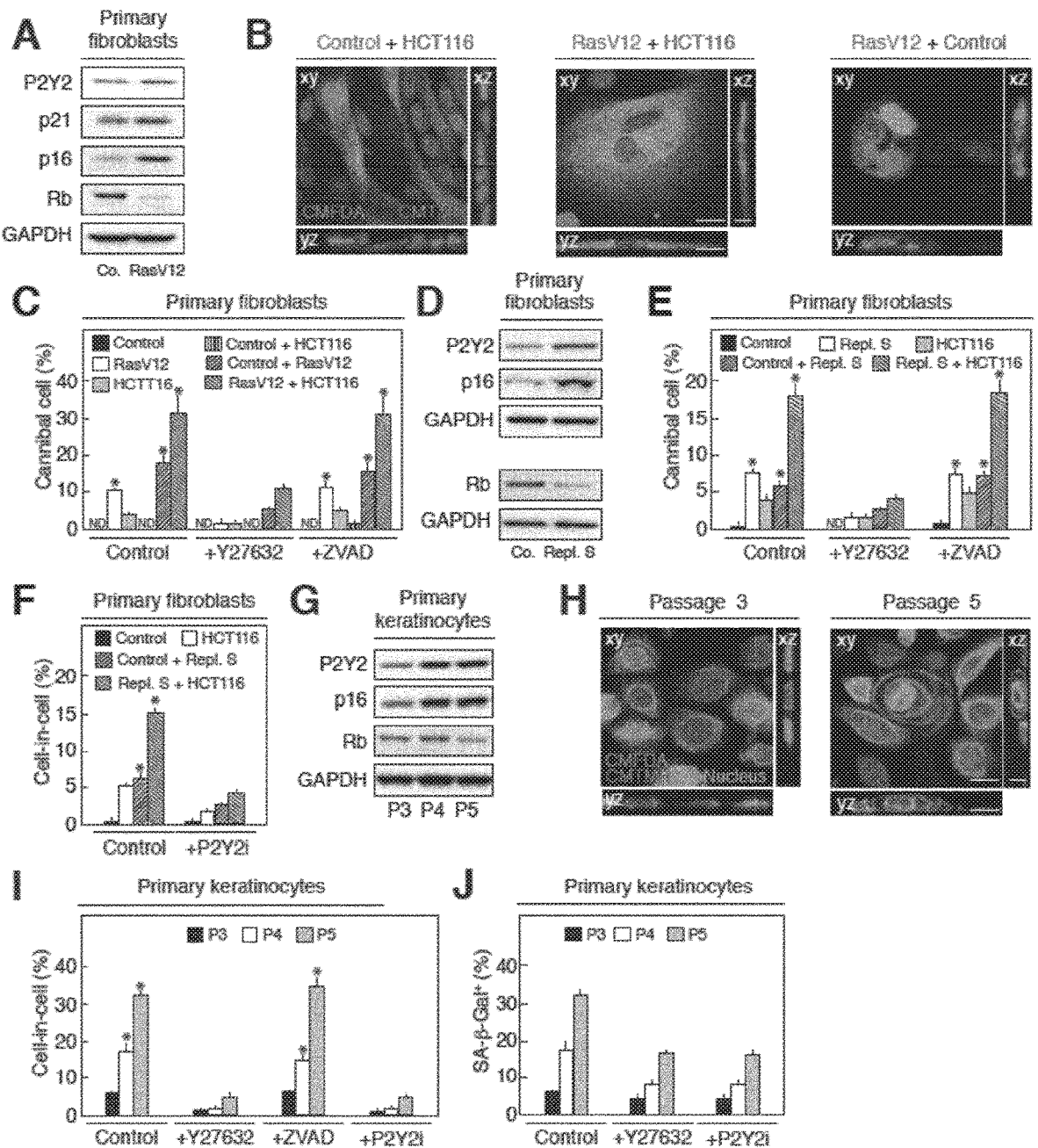

FIG. 5. Senescent cells exert cannibalistic activity. (A) Detection of P2Y2 overexpression during oncogenic induced senescence. Expression of P2Y2, p21$^{WAF1}$, p16$^{INK4b}$ and Rb during retroviral transduction of oncogenic Ras$^{V12}$ in human primary fibroblasts (WI38) were determined by immunoblot. Representative immunoblot of three independent experiments was shown. GAPDH was used as loading control. (B) Detection of cell-in-cell structures during coculture of human primary fibroblasts or RasV12 expressing human primary fibroblasts with human primary fibroblasts, with RasV12 expressing human primary fibroblasts or with colorectal HCT116 cells. Cell-in-cell structures were analyzed by confocal microscopy. Inserts represent xz and yz optical sections and show that Ras$^{V12}$ expressing fibroblasts internalized neighboring cells (human primary fibroblasts or HCT116 cells—. Representative micrographs of xy (scale bar, 5 μm) xz (scale bar, 4 μm) and yz (scale bar, 1 μm) optical sections are shown. Images are representative of at least three independent experiments. (C) Frequencies of cell-in-cell structures induced after transduction of oncogenic Ras$^{V12}$ in human diploid fibroblasts (WI38). The frequencies of cell-in-cell structures were determined for at least 300 cells in 3 independent experiments (mean+/−s.e.m, p<0.001). (D) Detection of P2Y2 overexpression during replicative stress induced senescence. Expression of P2Y2, p21$^{WAF1}$, p16$^{INK4b}$ and Rb during replicative senescence in human primary fibroblasts (WI38) were determined by immunoblot. Representative immunoblot of three independent experiments was shown. GAPDH was used as loading control, (E) Frequencies of cell-in-cell structures induced during replicative stress in human diploid fibroblasts (WI38). The frequencies of cell-in-cell structures were determined for at least 300 cells in 3 independent experiments (mean+/−s.e.m, p<0.001). (F) Effects of pharmacological inhibition of P2Y2 on cellular cannibalism detected during replicative induced senescence. Coculture of replicative stress induced senescent human fibroblasts with human primary fibroblast or colorectal HCT116 cells were realized during 24 hours in presence or in absence of 33 μM of Kaempferol. Then, frequencies of cell-in-cell structures induced during replicative stress in human diploid fibroblasts (WI38) were determined for at least 300 cells in 3 independent experiments (mean/−s.e.m, p<0.001). (G) Detection of P2Y2 overexpression during replicative stress induced senescence on human primary keratinocyte. Expression of P2Y2, p16$^{INK4b}$ and Rb during replicative senescence in human primary keratinocytes (HEKn) were determined by immunoblot. Representative immunoblot of three independent experiments was shown. GAPDH was used as loading control. (H) Detection of cell-in-cell structures during culture of human primary keratinocytes after 3 passages (P3), 4 passages (P4) or 5 passages (P5). A previously described, cell-in-cell structures were analyzed by confocal microscopy. Inserts represent xz and yz optical sections and show that replicative stress induced senescent fibroblasts internalized neighboring cells (human primary fibroblasts or HCT116 cells). Representative micrographs of xy (scale bar, 5 μm), xz (scale bar, 4 μm) and yz (scale bar, 1 μm) optical sections are shown. Images are representative of at least three independent experiments. (I) Effects of pharmacological P2Y2 inhibitor of P2Y2 on cellular cannibalism detected during replicative induced senescence. Coculture of replicative stress induced senescent human fibroblasts with human primary fibroblast or colorectal HCT116 cells were realized during 24 hours in presence or in absence of 33 μM of Kaempferol, 20 μM of Y27632 and 100 μM of ZVAD. Then, frequencies of cell-in-cell structures induced during replicative stress in human primary keratinocytes (HeKn) were determined for at least 300 cells in 3 independent experiments (mean+/−s.e.m, p<0.001).

Figure 6:
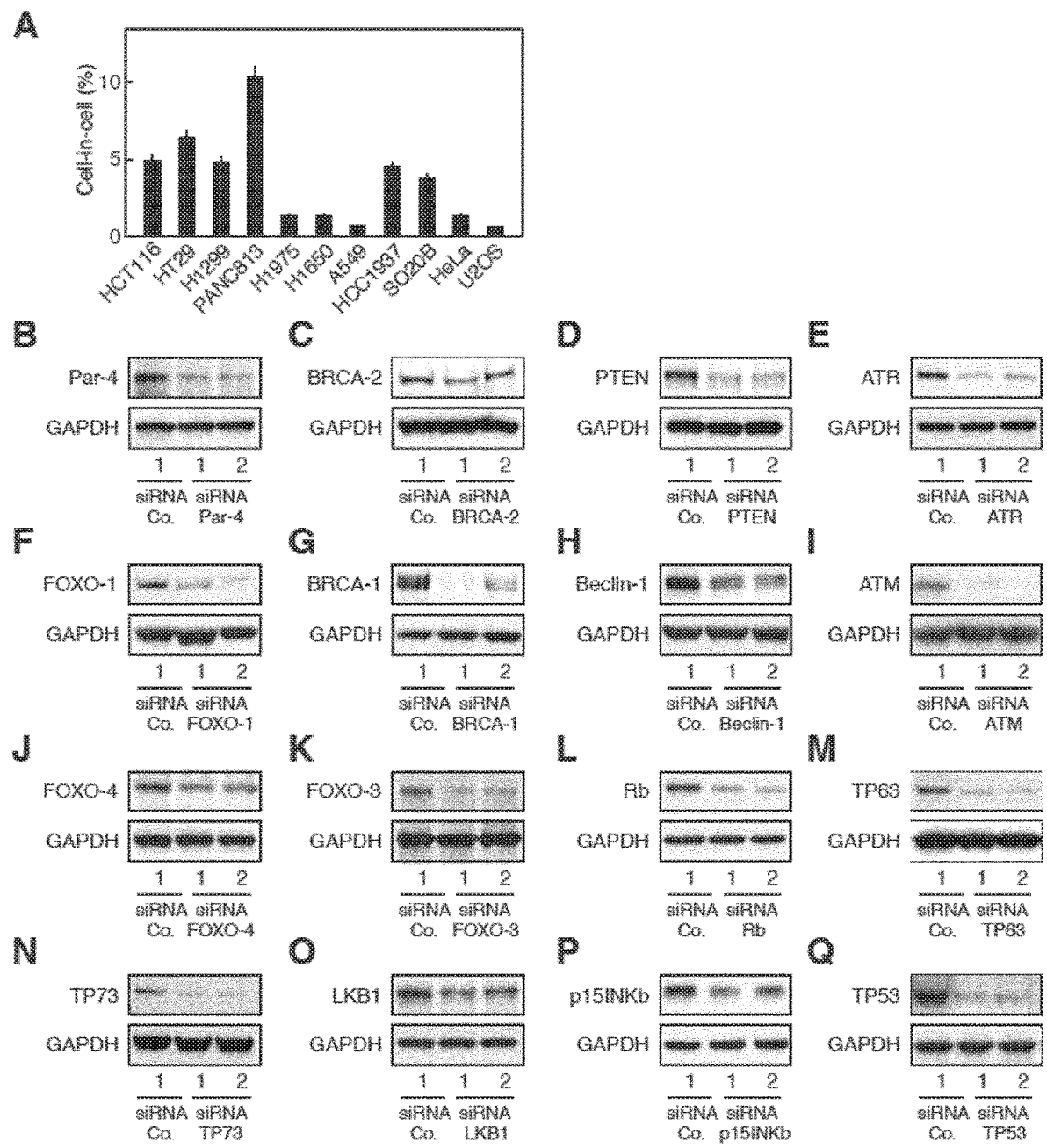

FIG. 6. Detection of cell-in-cell structures during culture of cancer cell lines and validation of tumor suppressor knockdowns, (A) Frequencies of cell-in-cell structures detected during culture of different cell lines as previously described. HCT116, HT29, H1299, PANC813, H1975, H1650, A549, HCC1937, SQ20B, HeLA and U2OS cells ware stained with CMTMR or CMFDA cell trackers, mixed and cultured during 24 hours. Quantification of cell-in-cell structures was realized by confocal microscopy. The frequencies of cell-in-cell structures were determined for at least 300 cells in 3 independent experiments mean+/−s.e.m, p<0.001). (B-Q) Validation of tumor suppressor knockdowns after transfection of two siRNA for Par-4 (B), BRCA-2 (C), PTEN (D), ATR (F), FOXO-1 (F), BRCA-1 (G), Beclin-1 (H), ATM (I), FOXO-4 (J), FOXO-3 (K), Rb (L), TP63 (M), TP73 (N), LKB1 (O), p15$^{INKb}$ (P) and TP53 (Q) was performed. Expression of indicated tumor suppressive proteins was determined by immunoblot. Representative immunoblots of three independent experiments are shown. GAPDH was used as loading control.

Figure 7:
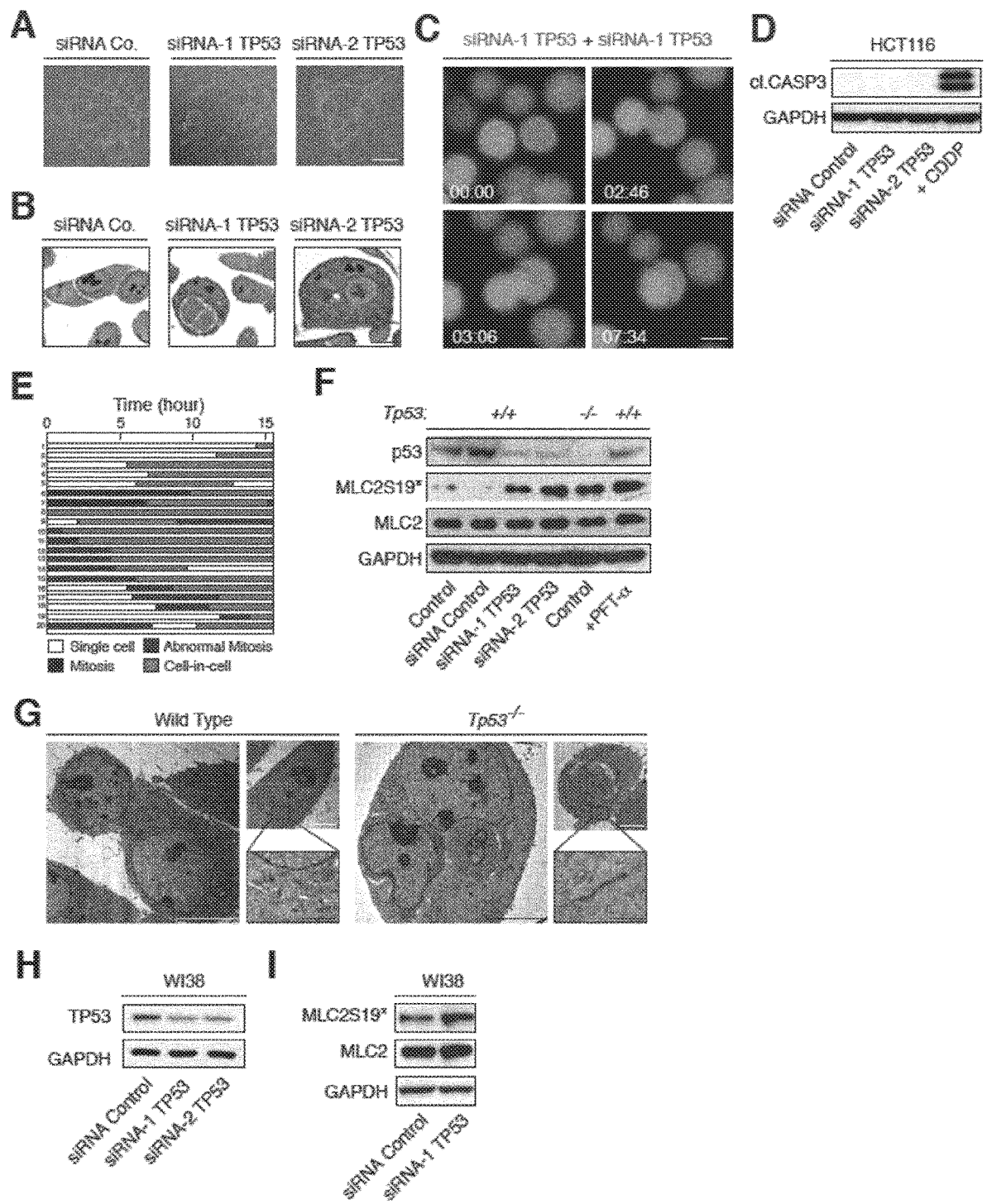

FIG. 7. Effects of TP53 inactivation on cellular cannibalism. (A) Detection of cell-in-cell structures induced by depletion of TP53, as visualized by confocal microscopy. Inserts represent xz and yz optical sections and show that after p53 depletion, red CMTR labeled HCT116 cells are internalized by green CMFDA labeled HCT116 cells. Images are representative of at least four independent experiments. (B) Detection of cell-in-cell structures induced by depletion of TP53 by light microscopy. (C) Time-lapse imaging of cellular cannibalism detected after depletion of TP53 on HCT116 cells. After 48 hours of transfection with siRNA against TP53, cells were stained as previously described with CMFDA and CMTMR cell trackers and cocultured under time-lapse confocal videomicroscopy. Indicated numbers represent hours and minutes. Time-lapse videomicroscopy image sequences shown are representative of at least three independent experiments. (D) Absence of apoptotic cleavage of caspase-3 during depletion of TP53. After 48 hours of TP53 knockdown, cleavage of caspase-3 was analyzed by immunoblot. Note that 100 mM of cisplatin (COOP) used as positive control revealed intense cleavage of caspase-3. GAPDH was used as loading control. Representative immunoblots of three independent experiments were shown. (E) Analyze of 20 independent Time-lapse videomicroscopy image sequences. Mitotic events and cellular cannibalism were detected and recorded during approximately fifteen hours. (F) Impact of TP53 inactivation on ROCK activity. ROCK activity was determined by detecting the phosphorylation of myosin light chain 2 on serine 19 (MLC2S19*). Lysates for 10 µM PFT-α treated—. TP53 knocked down, or TP53 knocked out HCT116 cells were analyzed for MLC2S19*, MLC2 or TP53 by immunoblot. GAPDH was used as loading control. Representative immunoblots of three independent experiments are shown, (G) Electron microscopy micrographies of cannibal cells. After 24 hours of culture. Tp53$^{-/+}$ and Tp53$^{-/-}$ HCT116 cells are fixed and analyzed by electron microscopy. Representative electron microscopy micrographies of three independent experiments are shown. (H,I) Effects of TP53 depletion on TP53 expression and on MLC2S19*. HCT116 cells were transfected with specific siRNAs for TP53 during 48 hours and expression of TP53 (H) or MLCS19* (I) were determined by immunoblots. GAPDH was used as loading control. Representative immunoblots of three independent experiments are shown.

Figure 8:
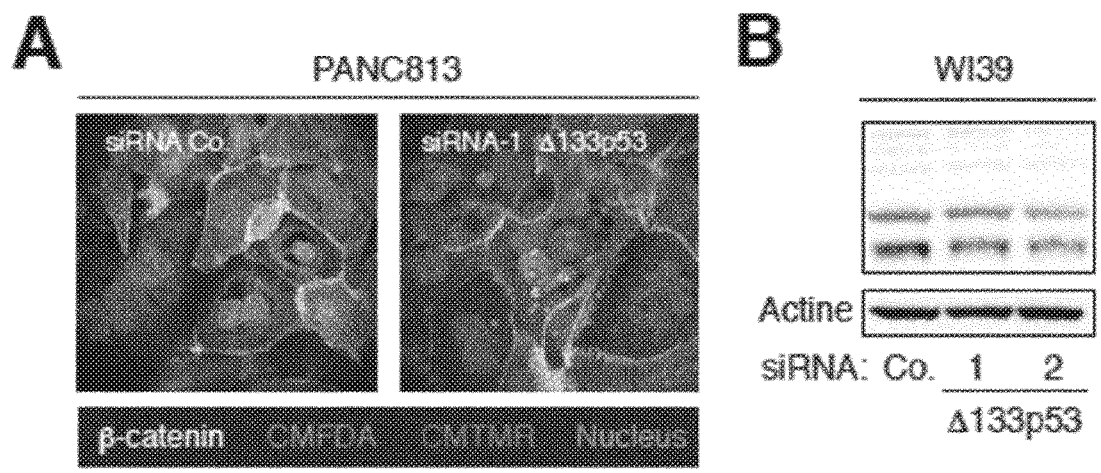

FIG. 8. Depletion of Δ133TP53 triggers cellular cannibalism of PANC813 cells and of human primary fibroblasts. (A) Detection of cell-in-cell structures after depletion of Δ133TP53 in PANC813 cells. After 48 hours of transfection with two specific siRNAs for Δ133TP53, PANC813 cells were stained as previously described, with CMFDA and CMTMR cell trackers and cocultured during 24 hours. Then, cells were fixed and stained for β-catenin (white) and nuclei (blue). Detection of cell-in-cell structures induced by depletion of Δ133TP53, as visualized by confocal microscopy. Representative micrographs are shown. Images are representative of at least four independent experiments (scale bar, 5 µm). (B) Analysis of Δ133TP53 depletion in human diploid fibroblasts. Expression of Δ133TP53 was GAPDH was used as loading control. Representative immunoblots of three independent experiments are shown.

Figure 9:
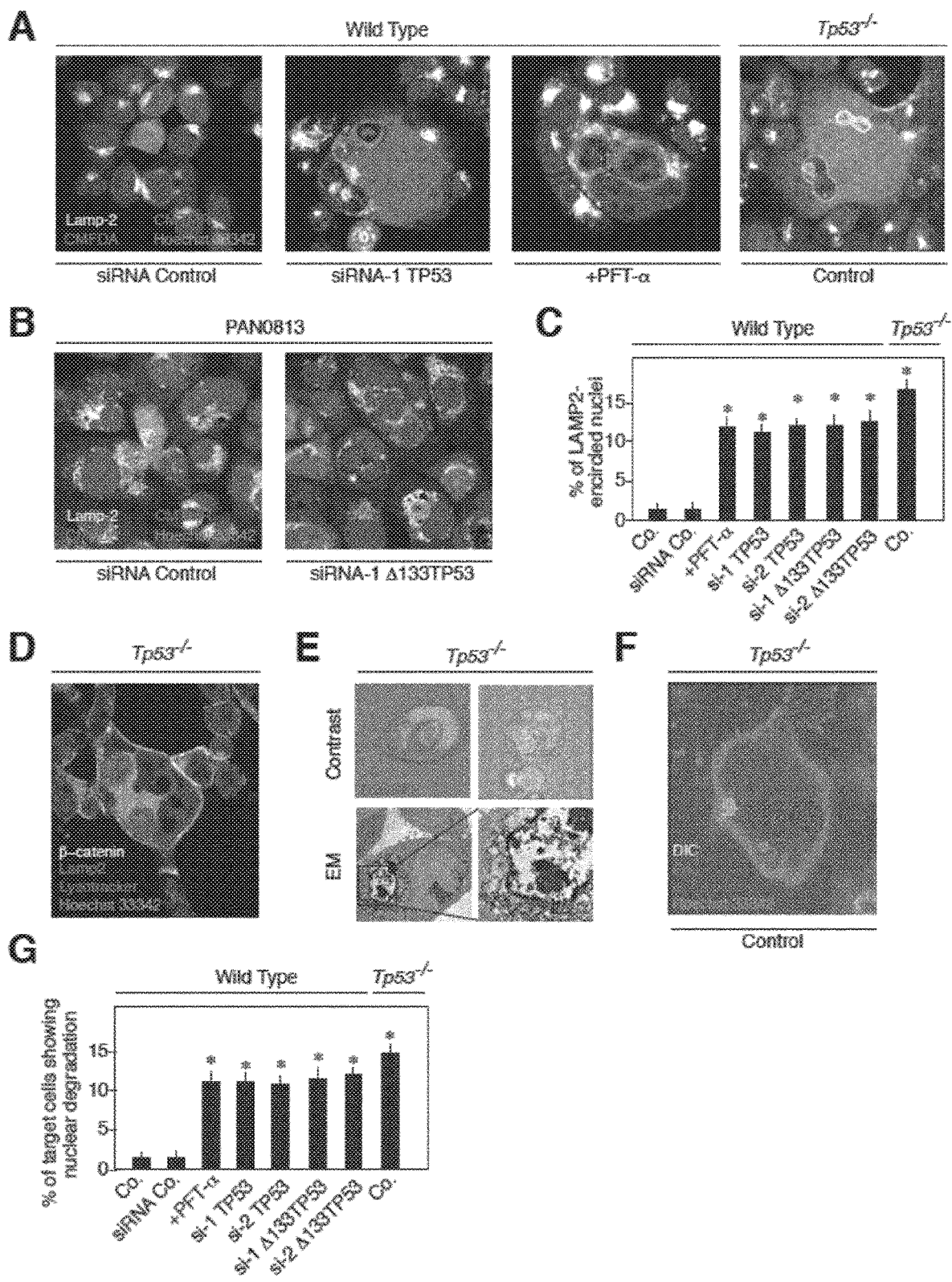
Figure 10:
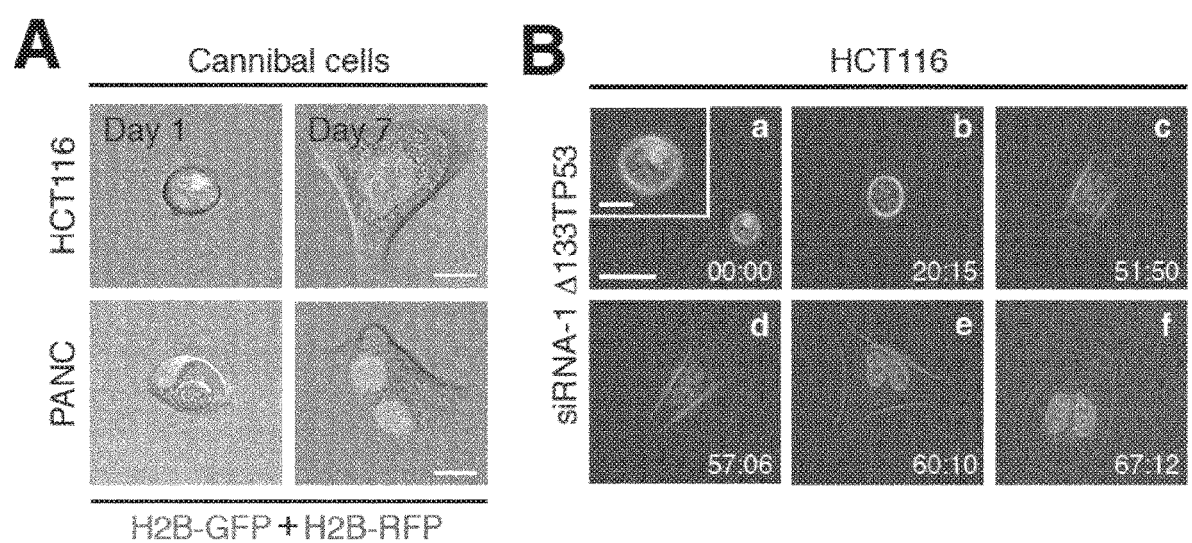
Figure 11:
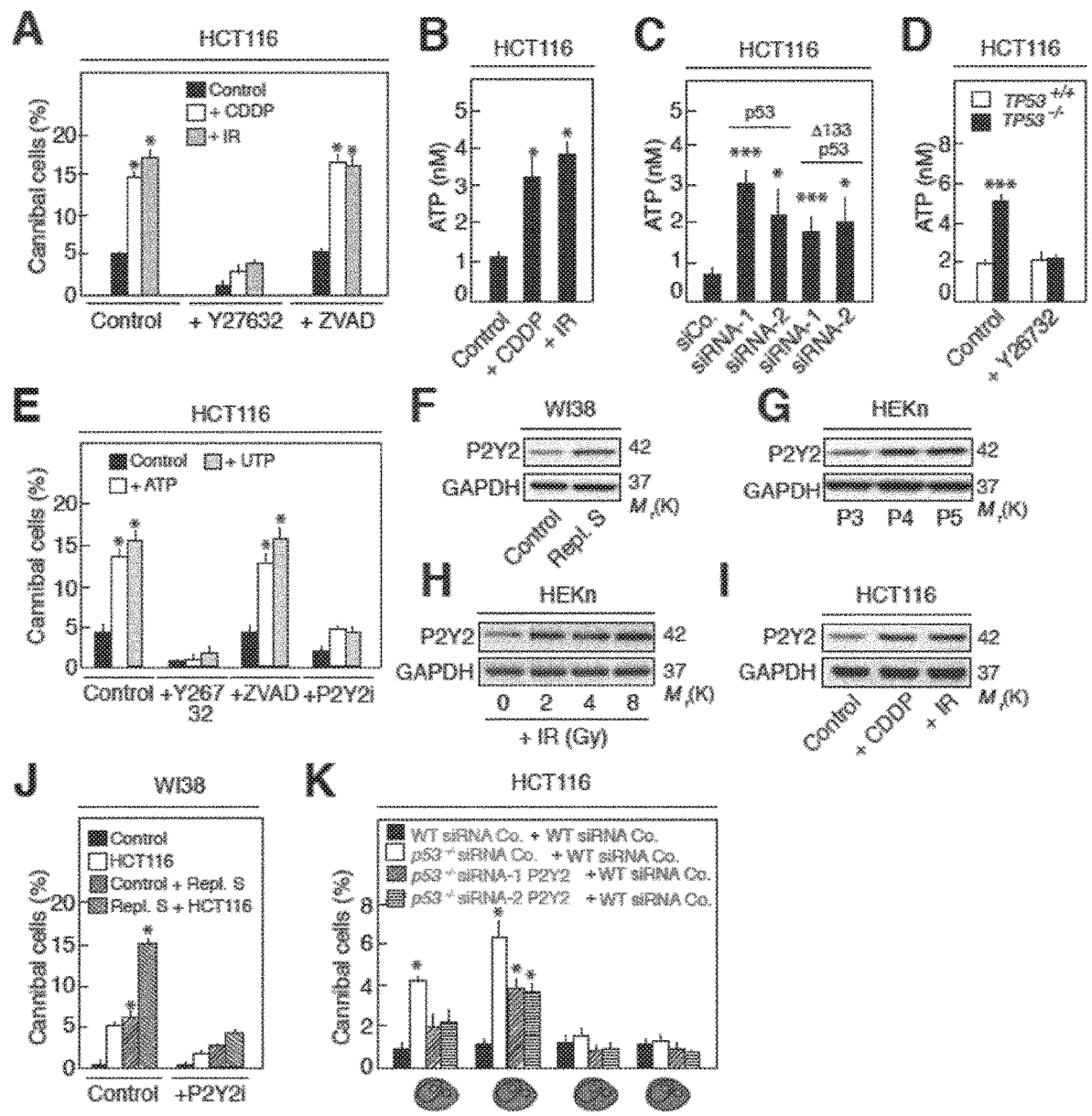

FIG. 9. Internalized cells are degraded by cannibal cells. (A) Detection of subcellular localization of lysosomal marker LAMP2 in cannibal cells obtained after PFT-α treatment, TP53 knockdown, or TP53 knockout. Subcellular localization of LAMP2 on cannibal cells was examined by confocal microscopy by LAMP2 (white), CMFDA (green), CMTMR (red) and Hoechst 33342 (blue) staining of HCT116 (A) or PANC0813 (B) cells. (C) Quantification of LAMP2 recruitment to internalized cells. The frequencies of LAMP2 encircled nuclei were determined for at least 300 cells in 3 independent experiments (mean+/−s.e.m, p<0.001). (D) Detection of lysosomal compartment in cannibal cells obtained after coculture of Tp53$^{-/-}$ HCT116 cells. As in (A), Subcellular localization of lysosomal compartment on cannibal cells was examined by confocal microscopy by β-catenin (white), LAMP2 (green), Lysotracker (red) and Hoechst 33342 (blue) staining of Tp53$^{-/-}$ HCT116 cells. (E) Detection of target cell degradation during cellular cannibalism. Isogenic Tp53$^{-/-}$ HCT116 cells that stably expressed green or red fluorescent proteins in their nuclei (GFP-histone H2B and RFP-histone H2B fusion proteins were mixed and cocultured for 24 hours. After fixation, these cells were analyzed by confocal microscopy or by electron microscopy and revealed that internalized cells are degraded. (F) Detection of nuclear degradation of internalized cells during cellular cannibalism obtained after culture of isogenic Tp53$^{-/-}$ HCT116 cells. Cannibal cells were examined by detecting EdU (green), α-tubulin (red), Hoechst 33342 (blue) stainings and phase contrast (grey) using confocal microscopy. Representative micrographs are shown. Images are representative of at least four independent experiments (scale bar, 5 µm), (G) Quantification of nuclear degradation of internalized cells during cellular cannibalism induced by TP53 and Δ133TP53 inactivation. The frequency nuclear degradation of internalized cells was determined for at least 300 cells in 3 independent experiments (mean+/−s.e.m, p<0.001), FIG. 10. Identification and characterization of cannibal cells after cell sorting. Isogenic pairs of cancer cell lines (HCT116 Tp53$^{+/-}$ PANC813) that stably expressed green or red fluorescent proteins in their nuclei (GFP-histone H2B and RFP-histone H2B fusion proteins) were mixed, cocultured, optionally after depletion of Δ133TP53 to induce entosis, and seeded in microliter plates (with one single structure per well) after cell sorting and analyzed by fluorescent microscopy. (A) Representative micrographs of cannibal cells obtained from HCT116 or PANC (Day 1 and Day 7) are shown. (B) Time-lapse videomicroscopy image sequences shown are representative of at least three independent experiments obtained after Δ133TP53 depletion, FIG. 11. Extracellular ATP and purinergic receptor P2Y2 participate in cellular cannibalism. (A.) Detection of cellular cannibalism after cis-platinium (CDDP) or γ-irradiation (IR) treatment. After 24 hours treatment with 10 µM CDDP or irradiation (IR) with 4 grays, half cell population of colon carcinoma HCT116 cells were stained with green CMFDA cell tracker or with red CMTMR cell tracker and analyzed for cellular cannibalism by confocal microscopy after 24 hours of coculture in presence or in absence of 20 µM of ROCK inhibitor (YI27632) or 100 µM of pan-caspase inhibitor (zVAD). The frequencies of cannibal cells were determined for at least 300 cells in 3 independent experiments (mean+/−s.e.m, *p<0.001). (B-D) Detection of ATP release after stimulation with senescent-induced stresses. Release of ATP on HCT116 cells treated with 10 µM CDDP (B) or 4 gray γ-irradiation (IR) (B) Of depleted for p53 (C) or Δ133p53 (C) was determined 2 hours after the beginning of coculture using ATP-dependent bioluminescence in 3 independent experiments, (D) Effect of ROCK inhibitor on ATP release detected after p53 inactivation. Release of ATP was detected as previously described in presence or in absence of 20 µM of Y27632 (mean+/−s.e.m, *p<0.001). (E) Effects of extracellular ATP and UTP on cellular cannibalism. Detection of cell-in-cell structures induced after the supplementation of ATP or UTP on culture of CMFDA and CMTMR labeled HCT116 cells. Representative micrographs are shown (scale bar, 5 µm). Images are representative of at least 3 independent experiments. Then, frequencies of cell-in-cell structures induced by ATP or UTP supplementations in HCT116 in presence or in absence of 20 µM of ROCK inhibitor (Y27632), of 100 µM pan-caspase inhibitor (zVAD) or 20 µM. of P2Y2 inhibitor Kaempferol. The frequencies of cell-in-cell structures were determined for at least 300 cells in 3 independent experiments (mean+/−s.e.m, *p<0.001). (E-M) Analysis of purinergic receptor P2Y2 expression after senescent-induced stresses. P2Y2 expression was determined by immunoblot on WI38 cells after hypoxia (F), during culture of human primary keratinocytes (HEKn) after 3 passages (P3), 4 passages (P4) or 5 passages (P5) (G), after irradiation with indicated doses of human primary keratinocytes (HEKn) (H), after treatment of HCT116 cells with 10 μM. CDDP or 4 gray γ-irradiation (IR) (I). Representative immunoblots of 3 independent experiments are shown. (J) Effects of pharmacological inhibition of P2Y2 on cellular cannibalism induced by replicative stress. Replicative stressed human primary fibroblasts were stained, mixed and cultured during 24 hours in presence or in absence of the 20 μM of P2Y2 inhibitor Kaempferol. The frequencies of cell-in-cell structures were determined for at least 300 cells in 3 independent experiments (mean+/−s.e.m, p<0.001). (K) Effects of P2Y2 depletion on cellular cannibalism observed after p53 or Δ133p53 depletions or p53 deletion. As previously described, HCT116 cells that are depleted for P2Y2 and/or inactivated for p53 or Δ133p53 were stained, mixed and cultured during 24 hours in presence or in absence of 20 μM of Y27632 or 100 μM of zVAD. The frequencies of cell-in-cell structures were determined for at least 300 cells in 3 independent experiments (mean+/−s.e.m, *p<0.001).

Figure 12:
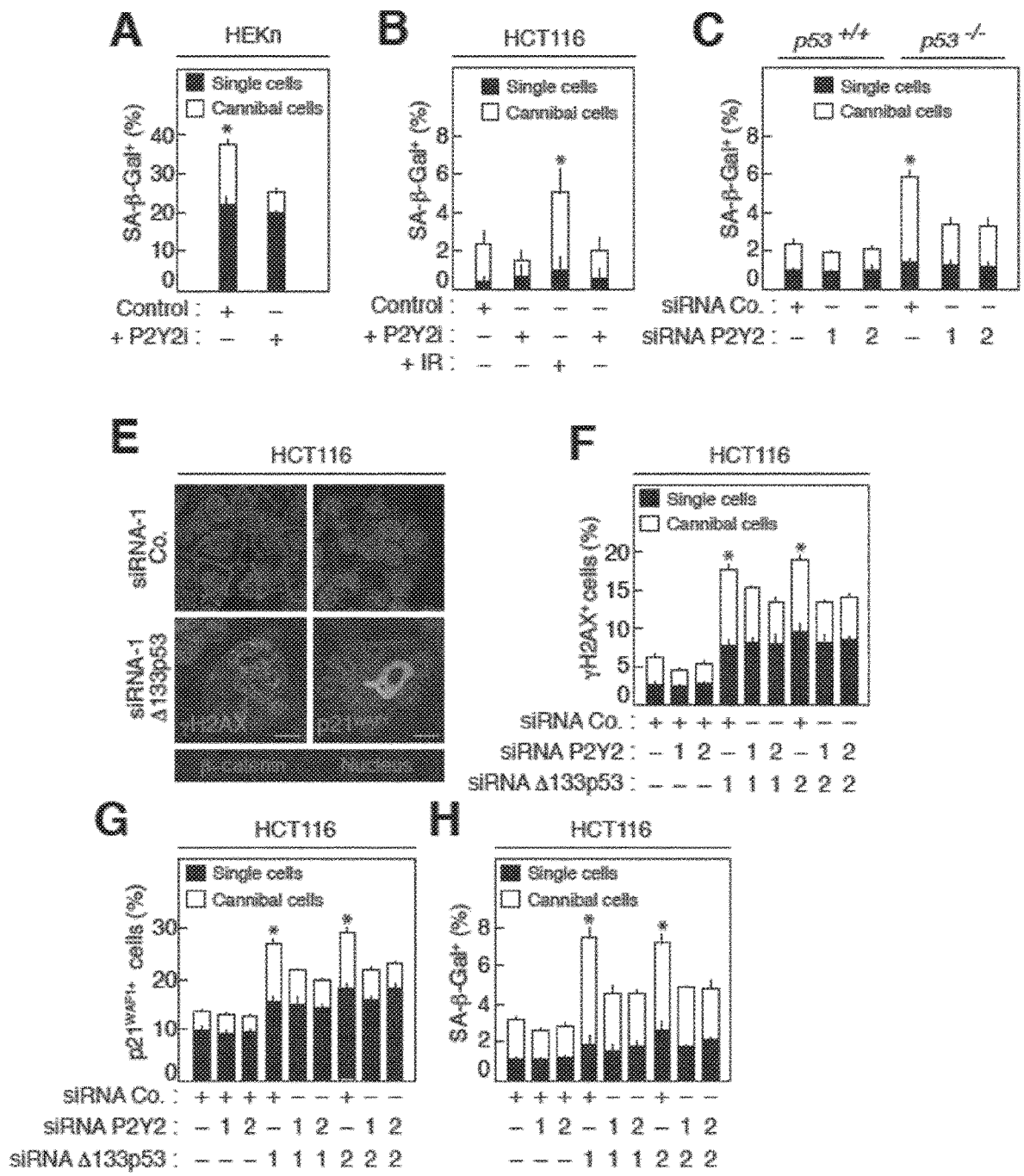

FIG. 12. Identification of entescence as a non-cell autonomous senescence. (A) Effects of P2Y2 inhibition on SA-β Gal activity of human primary keratinocytes. After the fifth passages, human primary keratinocytes were cultured during 24 hours in presence or in absence of 20 μM of P2Y2 inhibitor Kaempferol. The number of SA-β Gal positive single or cannibal cells per total number of cells examined (at least 300 per well) was recorded and frequencies of SA-β Gal positive were determined. Error bars represent means±SEM (n=3; *p <0.01). (B) Effects of P2Y2 inhibition on SA-β Gal activity detected after g-irradiation or mithoxantron treatment. HCT116 cells were treated with 10 μM CDDP or 4 gray γ-irradiation (IR) and incubated during 24 hours in presence or in absence of 20 μM of P2Y2 inhibitor Kaempferol. Then as described above frequencies of SA-β Gal positive were determined (means±SEM; n=3; *p <0.01). (C) Effects of P2Y2 depletion on SAT Gal activity observed after coculture of p53−/− HCT116 cells. As previously described, the number of SA-β Gal positive single or cannibal cells per total number of cells examined (at least 300 per well) was recorded (means±SEM; n=3; *p <0.01). (E) Detection of DNA damage response (DDR) foci and p21$^{WAF1}$ expression in single and cannibal cells after p53 or Δ133p53 inactivation. DNA damage response (DDR) foci were identified by γ-H2AX (green), β-catenin (red) and Hoechst 33342 (blue) staining of internalizing HCT116 cells. P21WAF1 expression was also analyzed using antibody against p21$^{WAF1}$ (green). Images are representative of at least three independent experiments (scale bar: 5 μm). (F-H) Effects of P2Y2 depletion on DNA damage foci formation, p21$^{WAF1}$ expression and SA-β Gal activity detected after Δ133p53. After P2Y2 depletion, the percentage of Δ133p53 depleted cells showing positivity for γ-I-H2AX$^+$ or p21$^{WAF1}$ expression were determined by confocal microscopy (G,H) and analyzed for p Gal activity (Means±SEM; n=3; *P <0.01).

Figure 13:
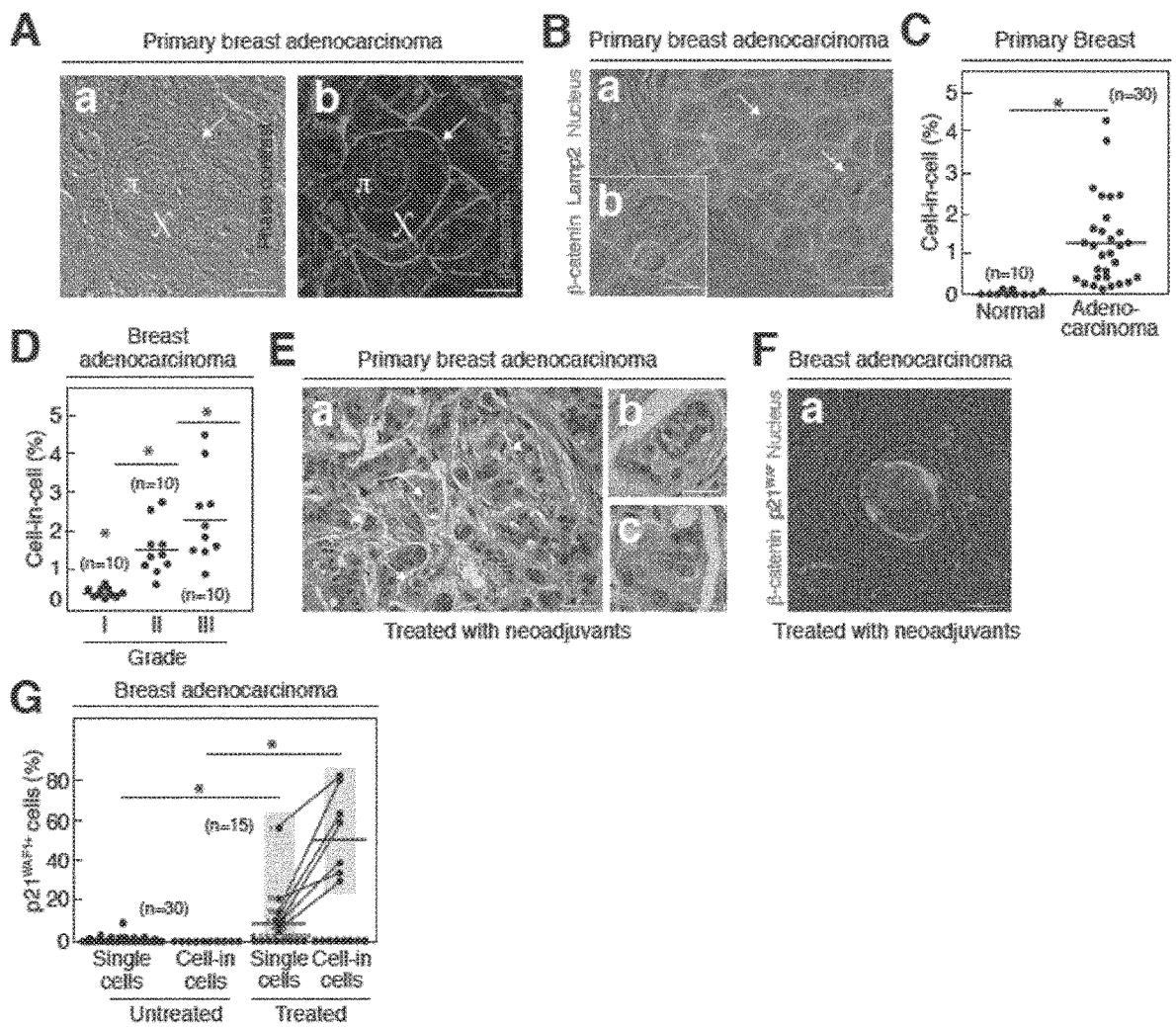

FIG. 13. Detection of Entescence in vivo. (A) Representative image of primary breast adenocarcinoma stained for β-catenin (green) and nuclei (blue) is shown (a). Phase contrast is also shown (b). Arrow marks cannibal cell.π and x respectively internalized nucleus and cannibal cell nucleus. (B) Representative image of primary breast adenocarcinoma stained for β-catenin (green), Lamp2 (red) and nuclei (blue) is shown in (a). Arrows indicate cannibal cells. Magnification of cannibal cell is shown in (b). (C) Quantification of cell-in-cell figures in normal primary breast (n-10) and in primary breast adenocarcinoma (n=30) biopsies (p<0.01). (D) Quantification of cell-in-cell figures in primary breast adenocarcinoma diagnosed for histological grade I (n=10), grade II (n=10) and grade III (n=10). (E) Representative images of primary breast adenocarcinoma obtained from patients treated with neo-adjuvant treatments stained by hematoxylin and eosin (HE). Four arrows mark cell-in-cell figures in (a). Magnifications of two representative images are shown in (b) and (c), (F) Representative image of primary breast adenocarcinoma biopsies obtained from patients treated with neo-adjuvant treatments stained for β-catenin (green), p2$^{WAF1}$ (red) and nuclei (blue) is shown. (G) Quantification of p21$^{WAF1}$ positive (p21$^{WAF1+}$) single cells or cell-in-cell figures detected on neo-adjuvant treated (n=15) or untreated primary breast adenocarcinoma biopsies (n=30) (p<0.001).

Figure 14:
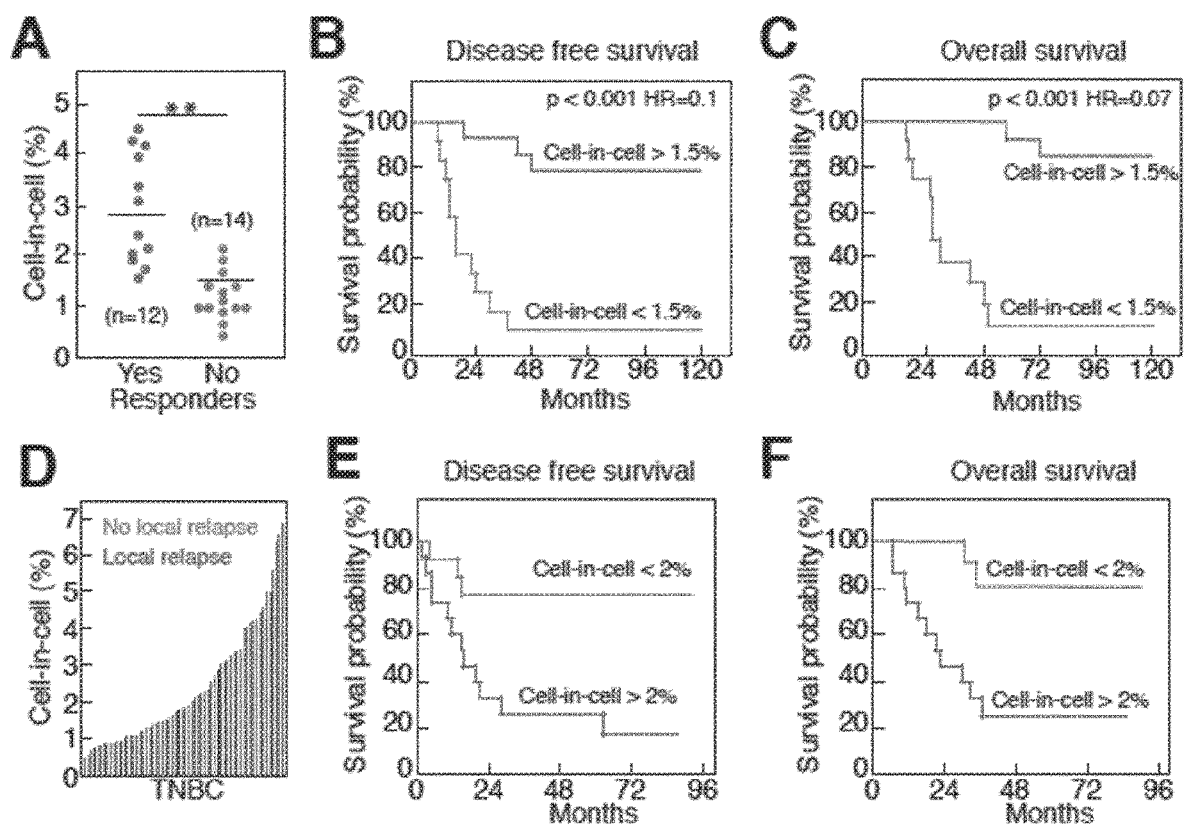

FIG. 14. Levels of cellular cannibalism and entescence could help for the prediction of treatment efficiency in breast cancer, (A) Quantification of cell-in-cell figures in primary breast adenocarcinoma biopsies obtained from patients that are good (n=12) or bad (n=14) responders to neo-adjuvant treatment (p<0.001). (B) Kaplan-Meier disease free survival of neo-adjuvant treated patients. (C) Kaplan-Meier overall survival of neo-adjuvant treated patients. (D) Quantification of cell-in-cell figures in primary triple negative breast adenocarcinoma biopsies obtained from patients that are good or bad responders to neo-adjuvant treatment (p<0.001). (E) Kaplan-Meier disease free survival of neo-adjuvant treated patients. (F) Kaplan-Meier overall survival of neo-adjuvant treated patients.

Figure 15:
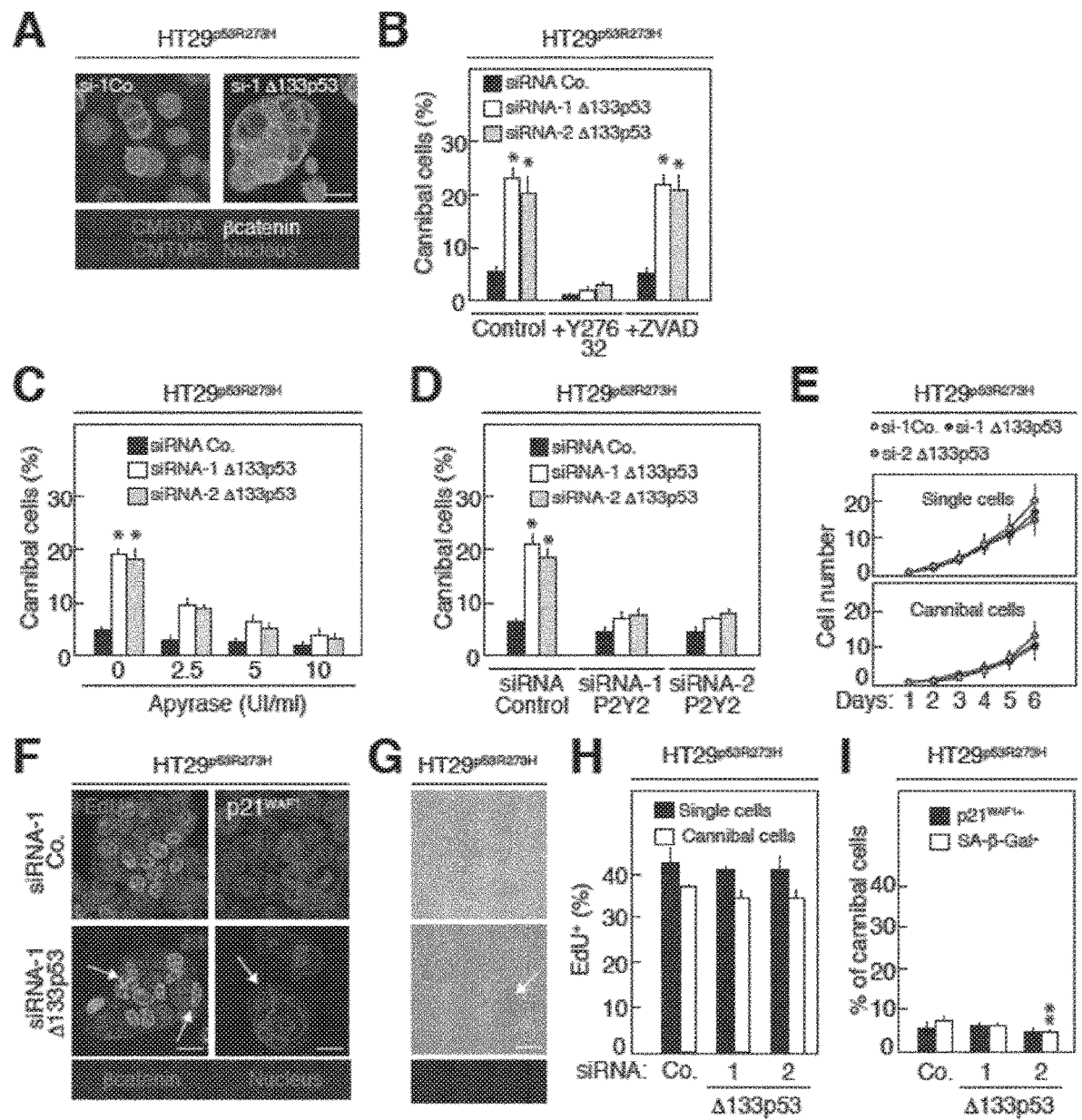

FIG. 15. Depletion of Δ133TP53 isoform induces cellular cannibalism in p53 mutated cells. (A) Detection of cell-in-cell structures induced by depletion of Δ133TP53 in HT29 (p53$^{R273H}$) cells, as visualized by confocal microscopy. Cell-in-cell structures were identified by b-catenin (white), CMFDA (green) and CMTMR (red) staining of internalizing HCT116 cells. Images are representative of at least four independent experiments (scale bar in a, 5 μm and scale bar in b, 1 μm). (B) Frequencies of cell-in-cell structures induced by Δ133TP53 knockdown, in HT29 cells in presence or in absence of 20 μm of ROCK inhibitor (Y27632) or 100 μm of pan-caspase inhibitor (zVAD). The frequencies of cell-in-cell structures were determined for at least 300 cells in 3 independent experiments (mean+/−s.e.m, p<0.001). Images are representative of at least four independent experiments (scale bar, 5 μm). (C) Effect of apyrase on cellular cannibalism. Cocultures of Δ133TP53 depleted HT29 cells in presence of different concentrations of apyrase were performed. Then, detection of cell-in-cell structures was performed by confocal microscopy (mean +/−s.e.m, n=3, p<0.001). (D) Effects of P2Y2 depletion on cellular cannibalism observed after Δ133TP53 depletion. As previously described, HT29 cells that are depleted for P2Y2 and/or inactivated for Δ133TP53 were stained, mixed and cultured during 24 hours. The frequencies of cell-in-cell structures were determined for at least 300 cells in 3 independent experiments mean +/−s.e.m, p<0.001). (E) Effects of cellular cannibalism on cell proliferation. After cell sorting, cell proliferation of Δ133TP53 knocked down single or cannibal HT29 cells were performed during 6 days. (F-I) Effects Δ133TP53 depletion on cellular cannibalism and on senescence induction of HT29 cells. Cannibal cells mediated Δ133TP53 knockdown were examined in EdU incorporation assay (F), in p21 expression assay (F) and in SA-β-Gal assay (G). (F) Determination of EdU incorporation on cannibal cells induced by Δ133TP53 knockdown. Cell-in-cell structures were identified by β-catenin (red) and Hoechst 33342 (blue) staining of internalizing HT29 cells, EdU positive cells are green. Images are representative of at least three independent experiments (scale bar: 5 µm). The detection of p21$^{WAF1}$ expression in single and cannibal HT29 cells after Δ133TP53 inactivation was also shown in (F). P21$^{WAF1}$ expression (white), β-catenin (red) and Hoechst 33342 (blue) staining of internalizing HCT116 cells is shown. Images are representative of at least three independent experiments (scale bar: .5 µm). Arrow show cannibal cells. (G) Representative picture of SA-β Gal staining of single and cannibal cells obtained after Δ133TP53 inactivation is shown. Arrow indicates cannibal cell (H) Determination of EdU incorporation in single and cannibal cells after Δ133TP53 inactivation. The number of EdU positive single or cannibal HT29 cells per total number of cells examined (at least 300 per well) was recorded (n=3). (F) Quantification of p21$^{WAF1}$ positive cells and SA-β Gal positive cells obtained after Δ133TP53 inactivation in cannibal cells after TP53 Δ133TP53 inactivation are shown. The percentage of p21$^{WAF1}$ cells or SA-β Gal cells were determined by confocal microscopy or by light microscopy. Error bars represent means±SEM (n=3; P <0.001).

DETAILED DESCRIPTION OF THE INVENTION

Cancer cells are characterized by several acquired capabilities that allow them to sustain proliferative signaling, to evade grog h suppressors, to resist to cell death, to enable replicative immortality, to reprogram energy metabolism, to induce angiogenesis, to escape immune system and to activate invasion (and metastasis) {Hanahan, Cell 2000; Hanahan, Cell 2011}. Signaling interactions between cancer cells and the tumor microenvironment cells (such as fibroblasts or immune cells) also contribute to cancer pathogenesis {Hanahan, Cell 2011}. Inactivation of tumor suppressor genes (such as p53) that is frequently detected in human tumors {Hanahan, Cell 2000; Hanahan, Cell 2011} contributes to the acquisition of theses cancer cell capabilities, but also impacts tumor pathogenesis by modulating signaling networks in the tumor microenvironment {Hanahan, Cell 2011}.

The tumor suppressor gene p53 (that is mutated in approximately half of human tumors) promotes a variety of cellular responses depending on the type of tissue, the nature of the stress signal and the cellular microenvironment {Vousden, Nature reviews Molecular cell biology 2009}. P53 promotes cell survival activity through the activation of survival signaling pathways {Janieke, Cell Death Differ 2008}, the protection against DNA damage {Bensaad, Cell 2006}, the modulation of energy metabolism {Tolstonog, PNAS 2010; Gottlieb, Cold Spring Harb Perspect Biol 2010} and antioxidant activities {Sablina, The Journal of biological chemistry 2005}. In addition, the signaling pathways operating upstream or downstream p53 can be interrupted in numerous tumors, suggesting that the pathways organized around p53 are critical for oncogenesis and tumor progression {Vogelstein, Nature 2000}. In response to a wide range of cellular stresses (including genotoxic damages, deregulated oncogenes, loss of cell contacts and hypoxia), p53 provides the elimination of cancer cells by stopping their developments (through anti-angiogenic activities {Tasdemir, J Mol Med 2007} or inhibition of their migration and invasion functions {Gadea, EMBO J. 2002; Gadea, J Cell Biol. 2007; Cartier-Michaud, PLoS One 2012}), by inducing cell death {Yonish-Rouach, Nature 1991} or by promoting senescence {Vousden, Cell 2007; Vousden, Nature reviews Cancer 2002}). Recent counterintuitive works reveal that p53 may also exert its activity through non-cell autonomous function by modifying senescent associated secreted profit (SAP) secretion {Coppe, PLoS Biol 2008} and by repressing in some circumstances cellular senescence {Demidenko, PNAS 2010}.

The N-terminal isoforms that lacked the transactivating domain (Δ40TP53 and Δ133TP53) act as dominant-negative regulators of p53 activity, and Δ133TP53 silencing has been associated with replication-induced senescence in normal human fibroblasts through enhanced transcriptional regulation of p53-target genes, such as p21$^{WAF1}$ and mir-34a (Fujita et al., Nat Cell Biol 2009).

Despite the diversity of functions of p53, the role of p53 in cellular cannibalism has never been studied.

In this context, the present inventors show here for the first time that the tumor suppressor TP53 and its Δ133TP53 isoform act as repressors of cellular cannibalism. Indeed, loss of TP53 or Δ133TP53 expression increases extracellular ATP release and the consequent activation of purinergic P2Y2 receptors which signals for engulfment. They further demonstrate that cannibal cells activate a senescence program through p2$^{WAF1}$ induction, unrevealing a new modality of induction of cellular senescence that can occur in the absence of TP53 or Δ133TP53. Senescence induced by oncogenic Ras and by replicative or oxidative stresses also results in cellular cannibalism, unrevealing that cannibalism is a common feature of senescent cells. Accordingly, cannibal cells found in human breast carcinomas exhibited signs of p21$^{WAF1}$ activation. Altogether, these results provide evidence that cellular cannibalism and senescence are tightly linked in human cancer. Moreover, the present inventors reveal that loss of p53 triggers an unsuspected senescent process that requires cell-in-cell internalization and entotic mechanisms to occur. This non-cell autonomous senescent process was called "entescence". It is observed during senescence-induced stresses (such oncogenic stimuli, replicative stresses, chemo- or radiotherapies) and in human tumors. In addition, they also demonstrate that senescence induced in cell autonomous manner also results in cellular cannibalism revealing that cellular cannibalism is a common feature of senescent culls. These results underscore the interplay between cellular cannibalism and senescence.

Definitions

For performing the different steps of the method of the present invention, there may be employed conventional molecular biology, microbiology and recombinant DNA techniques within the skill of the art. Such techniques are explained fully in the literature. See, for example, Sambrook, Fitsch & Maniatis, Molecular Cloning: A Laboratory Manual, Second Edition (1989) Cold Spring Harbor Laboratory Press, Cold Spring Harbor, N.Y. (referred to herein as "Sambrook et al., 1989"); DNA Cloning: A Practical Approach, Volumes I and II (D. N. Glover ed. 1985); Oligonucleotide Synthesis (M. J. Gait ed. 1984); Nucleic Acid Hybridization(B. D. Flames & S. J. Higgins, eds. 1984); Animal Cell Culture (R. I. Freshney, ed. 1986); Immobilized Cells and Enzymes (IRL Press, 1986); B. E. Perbal, A Practical Guide to Molecular Cloning (1984); F. M. Ausubel et al. (eds.), Current Protocols in Molecular Biology, John Wiley & Sons, Inc. (1994).

p53 (hereafter also referred to as TP53) is a protein of apparent molecular weight 53 kDa that functions as a transcription factor that, among other functions, regulates the cell cycle and functions as a tumor suppressor as mentioned above. Other isoforms or variants of p53 have been identified (see Bourdon, *Brit. J. Cancer*, 2007). For example, two other members of p53 family, p63 and p73, which are encoded by distinct genes, have been identified (Kaghad et al, *Cell* 1997; and Yang et al. *Mol. Cell* 1998). Human p53 isoforms may also arise due to alternative promoter usage and alternative Alternative promoter usage, for example, can give rise to the expression of an N-terminally truncated p53 protein initiated at codon 133 (Δ133p53 or Δ133TP53). Adding to the complexity of p53 isoforms is the alternative splicing of intron 9 of the p53 gene to provide the isoforms p53β and p53γ. Combined with alternative promoter usage, this gives rise to the p53 isoforms: p53, p53β (p53beta), p53γ (p53gamma), Δ133p53 (delta133p53), Δ133p5313 (delta133p53beta), and Δ133p53γ (delta33p53gamma). The use of an alternative promoter in intron 2 gives rise to the additional isoforms, Δ40p53 (delta40p53), Δ40p53β (delta40p53beta), and Δ40p53γ (delta40p53gamma). While the presence of these multiple p53 isoforms has been established, the biological function of these isoforms remains obscure. The present invention is based in part on an elucidation of the role for p53 and three of these isoforms, Δ133p53, p53β and p53γ, in the functions of cell senescence and cell cannibalism.

As used herein, the term "p53" refers generally to a protein of apparent molecular weight of 53 kDa on SDS PAGE that functions as the tumor suppressor described above. The protein and nucleic sequences of the p53 protein from a variety of organisms from humans to Drosophila are known and are available in public databases, such as in accession numbers, NM_000546 (SEQ ID NO:1), NP_000537 (SEQ ID NO:11, NM$_{011640}$ (SEQ ID NO:2) and NP_035770 (SEQ ID NO:12, for the human and mouse sequences respectively. It is also referred to as "p53α" or "p53alpha". It contains an entire transactivation domain (including TAD1, and TAD2), the PXXP domain, a DNA binding domain, the NLS and an entire oligomerisation domain in C-terminal.

The term "Δ133p53" or "delta133p53" or "Δ133TP53" or "delta133TP53" refers generally to the isoform of p53 that arises from initiation of transcription of the p53 gene from codon 133, which results in an N-terminally truncated p53 protein. This isoform comprises the following p53 protein domains: the majority of the DNA binding domain, the NLS, and the C-terminal sequence DQTSFQKENC see Bourdon, *Brit. J. Cancer*, 2007). It has for example SEQ ID NO:14. It is encoded for example by SEQ ID NO: 3.

The term "p53β" or "p53beta" refers generally to the isoform of p53 that arises from alternative splicing of intron 9 to provide a p53 isoform comprising the following p53 protein domains: TAD1, TAD2, prD, the DNA binding domain, the NLS, and the C-terminal sequence DQTSFQKENC (see Bourdon, *Brit. J, Cancer*, 2007). It has for example the sequence SEQ ID NO:15. It is encoded for example by SEQ ID NO: 4.

The term "p53γ" or "p53gamma" refers generally to the isoform of p53 that arises from alternative splicing of intron 9 to provide a p53 isoform comprising the following p53 protein domains: TAD1, TAD2, prD, the DNA binding domain, the NLS, and the C-terminal sequence MLLD-LRWCYFLINSS. It has for example the sequence SEQ ID NO:16. It is encoded for example by SEQ ID NO: 5.

The term "Δ40p53" or "Δ40TP53" or "delta40p53" or "delta40TP53" refers generally to the isoform of p53 that arises from whole splicing of intron 9, no splicing of intron 2 and normal splicing of exons 1,3 and 11 to provide a p53 isoform comprising the following p53 protein domains: TAD2, PXXP, the DNA binding domain, the NLS, and the entire oligomerisation domain in C-terminal. It has for example the sequence SEQ ID NO:13. It is encoded for example by SEQ ID NO: 6.

The term "promoting" as used, for example in the context of "promoting cannibalism," refers generally to conditions or agents which increase, induce, open, activate, facilitate, enhance activation, sensitize, agonize, or up regulate cell cannibalism.

"Inhibitors," "activators," and "modulators" of cellular cannibalism are used to refer to activating, inhibitory, or modulating molecules identified using the in vitro of the invention. Inhibitors are compounds that, decrease, prevent, or down regulate the expression of p53 isoforms. "Activators" are compounds that increase, facilitate, or up regulate activity of p53 isoforms. Inhibitors, activators, or modulators include naturally occurring and synthetic ligands, antagonists, agonists, antibodies, peptides, cyclic peptides, nucleic acids, antisense molecules, ribozymes, RNAi molecules, small organic molecules and the like. Such assays the inhibitors and activators include, e.g., expressing p53 isoforms in vitro, in cells, or cell extracts, applying putative modulator compounds, and then determining the functional effects on p53 expression, as described below. The term "test compound" or "drug candidate" or "modulator" or grammatical equivalents as used herein describes any molecule, either naturally occurring or synthetic, e.g., protein, oligopeptide (e.g., from about 5 to about 25 amino acids in length, preferably from about 10 to 20 or 12 to 18 amino acids in length, preferably 12, 15, or 18 amino acids in length), small organic molecule, polysaccharide, peptide, circular peptide, lipid, fatty acid, siRNA, polynucleotide, oligonucleotide, etc., to be tested for the capacity to directly or indirectly modulate p53 isoforms. The test compound can be in the form of a library of test compounds, such as a combinatorial or randomized library that provides a sufficient range of diversity. Test compounds are optionally linked to a fusion partner, e.g., targeting compounds, rescue compounds, dimerization compounds, stabilizing compounds, addressable compounds, and other functional moieties. Conventionally, new chemical entities with useful properties are generated by identifying a test compound (called a "lead compound") with some desirable property or activity, e.g., inhibiting activity, creating variants of the lead compound, and evaluating the property and activity of those variant compounds. Often, high throughput screening (HTS) methods are employed for such an analysis.

A "small organic molecule" refers to an organic molecule, either naturally occurring or synthetic, that has a molecular weight of more than about 50 daltons and less than about 2500 daltons, preferably less than about 2000 daltons, preferably between about 100 to about 1000 daltons, more preferably between about 200 to about 500 daltons.

Most of the methods of the invention are performed in vitro. As disclosed herein, the terms "in vitro" and "ex vivo" are equivalent and refer to studies or experiments that are conducted using biological components (e.g. cells or population of cells) that have been isolated from their usual host organisms (e.g. animals or humans). Such isolated cells can be further purified, cultured or directly analyzed to assess the presence of the mutant proteins. These experiments can be for example reduced to practice in laboratory materials such as tubes, flasks, webs, eppendorfs, etc. In contrast, the term "in vivo" refers to studies that are conducted on whole living organisms.

The screening methods of the invention are preferably performed on cell samples expressing p53 isoforms. In the context of the invention, these cell samples contain for example cell lines that are known to express one or the other isoforms. In a preferred embodiment, these cell lines are primary human diploid WI38 fibroblasts or cancer cell lines such as colorectal HCT116 carcinoma or pancreatic PANC813 cells.

The prognosis methods of the invention are preferably performed on a biological sample obtained from a patient in need thereof. As used in the context of these methods, the term "biological sample" advantageously refers to a serum sample, a plasma sample, a blood sample, a lymph sample, or to a tumor tissue sample obtained by biopsy. Preferably, the said biological sample is a blood sample or a tumor tissue sample obtained from a tumor biopsy. Said tissue sample is for example a tumor sample obtained from a primary breast adenocarcinoma, a primary cervical adenocarcinoma, a primary pancreatic adenocarcinoma, a primary melanoma, primary spitz tumors, a primary stomach or liver carcinoma.

The prognosis method of the invention can include the steps consisting of obtaining a biological sample from said subject and extracting the nucleic acid from said biological sample. The DNA can be extracted using any known method in the state of the art. The RNA can also be isolated, for example from tissues obtained during a biopsy, using standard methods well known to those skilled in the art, such as extraction by guanidium-thiophenate-phenol-chloro form.

The expression level of a protein in a biological sample is determined by:

a method including a PCR, qPCR, a RT-PCR method, in situ hybridization, a Northern method or microarrays when the expression level of RNA transcripts encoding a defined protein is to be determined; or Enzyme linked immunosorbent assays (ELISAs), Western blots, immunoprecipitations, immunofluorescence method, electron method or Enzyme-linked staining method for microscopic detection immunohistochemistry assay), or flow cytometry, when the expression level of the protein itself is to be determined.

Such methods are well known from the skilled person (see e.g., Current Protocols in Molecular Biology, John Wiley & Sons, Inc. (1994).

In a preferred embodiment, quantitative RT-PCR (qPCR) analysis can be used to measure the mRNA expression levels in a biological sample. Gene expression analysis by real-time quantitative PCR (RT-qPCR) is well known from the skilled person. For example, p53 mRNA expression analysis by RT-qPCR can be assessed after standard tissue sample RNA extraction (for example, the samples can be lysed in a tris-chloride, EDTA, sodium dodecyl sulphate and proteinase K containing buffer; RNA can be then extracted with phenol-chloroform-isoamyl alcohol followed by precipitation with isopropanol in the presence of glycogen and sodium acetate; RNA can be resuspended in diethyl pyrocarbonate water (Ambion Inc., Austin, Tex.) and treated with DNAse 1 (Ambion Inc., Austin, Tex.) to avoid DNA contamination; complementary DNA can be synthesized using for example Maloney Murine Leukemia Virus retrotranscriptase enzyme; template cDNA can be added to Taqman Universal Master Mix (AB, Applied Biosystems, Foster City, Calif.) with specific primers and probe for each p53 isoforms.

The primer and probe sets can be designed using Primer Express 2.0 Software (AB) and the reference sequences (which can be obtained on the web site http://www.ncbi.nlm.nih.gov/entrez/query. fcg,i?db=gene). Nucleic acid probes and primers for hybridizing specifically the mRNA or cDNA of p53 isoforms are well-known in the art. They are typically of at least 10, 15 or 20 nucleotides in length that is sufficient to specifically hybridize under stringent conditions to the mRNA or cDNA of p53 isoforms, or complementary sequence thereof (preferred are oligonucleotide primers or probe having at least 90%, 95%, 99% and 101) % identity with the mRNA sequence fragment of the p53 isoforms or the complementary sequence thereof).

Protein expression levels can be for example detected using antibodies specifically directed against different specific regions or epitope of the p53 protein and isoforms thereof. The term "antibody" as used herein refers to immunoglobulin molecules and immunologically active portions of immunoglobulin molecules, i.e., molecules that contain an antigen binding site which specifically binds (or immunorcacts with) the p53 protein or isoforms thereof. The term "antibody" comprises monoclonal or polyclonal antibodies but also chimeric or humanized antibodies. These antibodies preferably differently bind the different isoforms of p53. These antibodies are for example the commercial mouse monoclonal DO-1 and DO-7 (recognizing specifically the p53β and p53γ isoforms), the commercial mouse monoclonal 1801 (recognizing all p53 isoforms except Δ133p53, the commercial mouse monoclonal antibodies BP53.10, 421, and ICA-9 (that are specific for the α isoforms of p53 (p53, Δ40p53, and Δ133p53), because their epitopes are localized in the basic region (BR) of the p53 protein), and the rabbit polyclonal antibodies KJC8 (recognizing specifically p53β) and MAP4.9 (recognizing specifically $\Delta 133p^5$ see Khoury M. P. and Bourdon J. C. Cold Spring Perspect Biol. 2010).

Preferably, the antibodies and probes used in the methods of the invention are labeled so as to be detected.

The term "labeled" with regard to a probe or an antibody, is intended to encompass direct labeling of the probe or antibody by coupling (i.e., physically linking) a detectable substance to the probe or antibody, as well as indirect labeling of the probe or antibody by reactivity with another reagent that is directly labeled. Examples of indirect labeling include detection of a primary antibody using a fluorescently labeled secondary antibody and end-labeling of a DNA probe with biotin such that it can be detected with fluorescently labeled streptavidin.

In the screening methods of the invention, cells expressing various p53 isoforms are treated with potential activators, inhibitors, or modulators so as to examine the extent of p53 isoform expression level modulation. In this case, "control levels" correspond to p53 isoform expression levels and/or ATP release and/or P2Y2R expression or activity levels measured in control cells, said control cells preferably being the same cells that have not been treated with said activators, inhibitors, or modulators. Therefore, control levels correspond to p53 isoform and/or ATP and /or P2Y2R expression levels measured in non treated cells.

In a particular embodiment, control samples (untreated) can be assigned a relative protein expression value of 100%. In this case, decrease (or repression) of the expression (or expression level) of a target protein would be achieved when the expression level of said protein is of about 80%, preferably 50%, more preferably 25-0% relative to the control level. Conversely, increase (or promotion) of the expression (or expression level) of a target protein would be achieved when the expression level of said protein is at least of about 110%, more preferably at least of about 150%, and is more preferably of 200-500% (i.e., two to five fold superior to the control), more preferably of 1000-3000% relative to the control level.

Also, as used in the present application, a "low" expression of a target protein is achieved when the expression level of said protein is less than about 80%, preferably less than about 50%, more preferably less than about 25% relative to the control level. Conversely, a "high" expression of a target protein is achieved when the expression level of said protein is at least of about 110%, more preferably at least of about 150%, and is more preferably of 200-500% relative to the control level, i.e., from two to five folds superior to the control level.

In the prognosis methods of the invention, the p53 isoform or P2Y2R expression levels measured in the tumor cells of the patients are compared with "control level(s)". These control levels are preferably measured in normal cells or in non-treated tumor cells of the same patient, more preferably in normal cells of at least one another subject, preferably of an healthy subject.

Adenosine-5'-triphosphate (ATP) is a nucleoside triphosphate used in all living cells for intracellular energy transfer. It is one of the end products of photophosphorylation, cellular respiration, and fermentation and used by enzymes and structural proteins in many cellular processes, including biosynthetic reactions, motility, and cell division. One molecule of ATP contains three phosphate groups. The structure of this molecule consists of a purine base (adenine) attached to the carbon atom of a pentose sugar (ribose). Three phosphate groups are attached at the 5' carbon atom of the pentose sugar. It is produced by a wide variety of enzymes, including ATP synthase, from adenosine diphosphate (ADP) or adenosine monophosphate (AMP) and various phosphate group donors.

ATP has the formula I

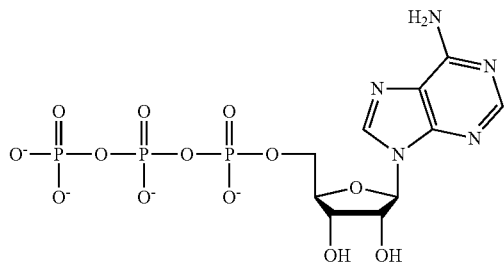

ATP is typically quantified by measuring the light produced through its reaction with the naturally occurring firefly enzyme luciferase using a luminormeter. The amount of light produced is directly proportional to the amount of ATP present in the sample.

Extracellular ATP can be measured easily by a number of commercial kits (e.g., the Enliten ATP assay system of Promega). High-Performance liquid chromatography (HPLC) may also be used to measure extracellular levels of ATP.

The P2Y2 purinergic receptor, also known as "P2Y purinoceptor 2" or "P2Y2R" is a protein that in humans is encoded by the P2RY2 gene located on the chromosome 11 (Parr C E. et al, 1994, *PNAS* 1991), This receptor belongs to the family of G-protein coupled receptors. It favors the production of both the adenosine and uridine nucleotides. It may participate in control of the cell cycle of several cancer cells. In human, three transcript variants encoding the same protein have been identified for this gene. These transcripts have the sequence SEQ ID NO:7 (variant 1) SEQ ID NO:8 (variant 2) and SEQ ID NO:9 (variant 3). The human P2Y2 purinergic receptor has the polypeptide sequence SEQ ID NO:10.

siRNAs are described for example in WO 02/44 321 (MIT/MAX PLANCK INSTITUTE). This application describes a double strand RNA (or oligonucleotides of same type, chemically synthesized) of which each strand has a length of 19 to 25 nucleotides and is capable of specifically inhibiting the post-transcriptional expression of a target gene via an RNA interference process in order to determine the function of a gene and to modulate this function in a cell or body. Also, WO 00/44895 (BIOPHARMA) concerns a method fir inhibiting the expression of a given target gene in a eukaryote cell in vitro, in which a dsRNA formed of two separate single strand RNAs is inserted into the cell, one strand of the dsRNA having a region complementary to the target gene, characterized in that the complementary region has at least 25 successive pairs of nucleotides. Persons skilled in the art may refer to the teaching contained in these documents to prepare the siRNAs of the invention.

MicroRNAs (hereafter referred to as miRNAs) are small non-coding RNA molecule (ca. 22 nucleotides) found in plants and animals, which functions in transcriptional and post-transcriptional regulation of gene expression, miRNAs function via base-pairing with complementary sequences within mRNA molecules, usually resulting in gene silencing via translational repression or target degradation, miRNAs have been proposed in therapeutic strategies for treating cancer and acute ischemic diseases (Li C. et al, *AAPSJ*, 2009; .Fasanaro et al, *Pharmacol. Ther.* 2010).

By "pharmaceutically acceptable vehicle", it is herein designated any and all solvents, buffers, salt solutions, dispersion media, coatings, antibacterial and antifungal agents, isotonic and absorption delaying agents, and the like that are physiologically compatible. The type of carrier can be selected based upon the intended route of administration. In various embodiments, the carrier is suitable for intravenous, intraperitoneal, subcutaneous, intramuscular, topical, transdermal or oral administration. Pharmaceutically acceptable carriers include sterile aqueous solutions or dispersions and sterile powders for the extemporaneous preparation of sterile injectable solutions or dispersion. The use of media and agents for pharmaceutically active substances is well known in the art.

An "effective amount" herein refers to an amount that is effective, at dosages and for periods of time necessary, to achieve the desired result, i.e., to treat effectively the patient. An effective amount as meant herein should also not have any toxic or detrimental severe effects.

Screening Methods for Identifying Modulators of Cellular Cannibalism and Senescence In a first aspect, the present invention provides methods for identifying compounds that modulate cell cannibalism via its effect on p53 or Δ133p53, In general, the method includes these steps: (a) contacting a candidate compound with a sample that comprises p53 or Δ133p53, and (b) determining the functional effect of the candidate compound on the expression level of p53 or Δ133p53, based on which one may determine whether the said compound is an activator or an inhibitor of cellular cannibalism.

In one embodiment, the present invention relates to a method of identifying a compound that modulates cellular cannibalism, comprising the steps of:

(a) adding a compound to a cell culture in vitro,
(b) measuring in said culture the expression level of a protein selected from the group consisting of p53 and N-terminal isoforms of p53 that lack the N-terminal transactivating domain, such as Δ40TP53 and Δ133TP53;
wherein a compound that represses cellular cannibalism is identified by a normal expression or an increase in the expression levels of p53 or said isoforms, as compared to control levels.

Preferably, the said compound increases cellular cannibalism if the expression level of p53 or said isoforms decreases, as compared to control levels.

By "normal expression", it is herein meant that the expression of p53 or of its N-terminal isoforms lacking the N-terminal transactivating domain is almost identical 5%) to the control levels.

More preferably, in this embodiment, said cell culture contains or consists of primary human diploid WI38 fibroblasts, or cancer cell lines such as colorectal HCT116 carcinoma or pancreatic ductal PANC813 adenocarcinoma.

Even more preferably, in this method, p53 is the polypeptide of SEQ ID NO11, Δ40TP53 is the polypeptide of SEQ ID NO:13, and Δ133TP53 is the polypeptide of SEQ ID NO:14.

In another embodiment, the present invention relates to a method of identifying a compound that modulates cellular cannibalism, comprising the steps of:
(a) adding a compound to a cell culture in vitro,
(b) measuring in said culture the expression level of a protein selected from the group consisting of p53β and p53γ,
wherein a compound that represses cellular cannibalism is identified by a decrease in the expression levels of p53β and/or p53γ, as compared to control levels.

Preferably, the said compound increases cellular cannibalism if the expression levels of p53β and p53γ are increased as compared to control levels.

More preferably, s in this embodiment, said cell culture contains or consists of primary human diploid WI38 fibroblasts or cancer cell lines such as colorectal HCT116 carcinoma or pancreatic ductal PANC813 adenocarcinoma.

Even more preferably, in this method, p53β is the polypeptide of SEQ ID NO:15 and is the polypeptide of SEQ ID NO:16.

In another embodiment, the present invention relates to a method of identifying a compound that modulates cellular cannibalism, comprising the steps of:
(a) adding a compound to a cell culture in vita
(b) measuring in said culture the extracellular amount of ATP,
wherein a compound that represses cellular cannibalism is identified by a decrease in the extracellular amount of ATP, as compared to control levels.

Preferably, said compound increases cellular cannibalism if the extracellular amount of ATP, is increased as compared to control levels.

More preferably, in this embodiment said cell culture contains or consists of primary human diploid WI38 fibroblasts or cancer cell lines such as colorectal HCT116 carcinoma or pancreatic ductal PANC813 adenocarcinoma.

In another embodiment, the present invention relates to a method of identifying a compound that modulates cellular cannibalism, comprising the steps of:
(a) adding a compound to a cell culture in vitro,
(b) measuring in said culture the expression level or the activity of the purinergic P2Y2 receptor,
wherein a compound that represses cellular cannibalism is identified by a decrease in the expression level car in the activity of the puringergic P2Y2 receptor, as compared to control levels.

Preferably, said compound increases cellular cannibalism if the expression level or the activity of the purinergic P2Y2 receptor increases, as compared to control levels.

In this method, the expression level of purinergic P2Y2 receptor may be measured as defined above, that is, by measuring the mRNA level or the protein level of the said receptor in the cells.

Alternatively, this method may involve the measurement of the activity of the purinergic P2Y2 receptor. By "activity", it is herein mean the "biological activity" of the said receptor. P2Y2 receptor biological activity is triggered by the binding of extracellular nucleotides (such as ATP and UTP) and is coupled to intracellular signaling pathways through heterotrimeric G proteins activation and formation of a polyprotein complex that activates kinases (such as the proline-rich tyrosine kinase 2 (Pyk2)) involved in numerous cellular functions like plasma membrane permeabilization, $Ca^+$ influx and cytoskeleton reorganization. It can be detected for example by determining the phosphorylation of Pyk2 on tyrosine 402, one cellular consequence of P2Y2 biological activity (Séror et al., *The Journal of e medicine* 2011).

More preferably, in this embodiment, said cell culture contains or consists of primary human diploid WI38 fibroblasts or cancer cell lines such as colorectal HCT116 carcinoma or pancreatic ductal PANC813 adenocarcinoma.

Even more preferably, in this method, the purinergic P2Y2 receptor is the polypeptide of SEQ ID NO:10.

Of course, a combination of the above-mentioned steps can be used to identify compounds that modulate cellular cannibalism.

Consequently, the present invention also relates to a screening method comprising the step of a cell culture:
the expression level of protein selected from the group consisting of p53 and N-terminal isoforms of p53 that lack the N-terminal transactivating domain, such as Δ40TP53 and ΔA133TP53, and
the expression level or the activity of the purinergic P2Y2 receptor,
wherein the tested compound represses cellular cannibalism if the expression levels of p53 or said isoforms increase, as compared to control levels, and if the expression level or the activity of the purinergic P2Y2 receptor decreases, as compared to control levels.

In a preferred embodiment, the tested compound increases cellular cannibalism if the expression levels of p53 or said isoforms decrease, as compared to control levels, and if the expression level of the purinergic P2Y2 receptor or the activity increases, as compared to control levels.

More preferably, in this embodiment, said cell culture contains or consists of primary human diploid WI38 fibroblasts or cancer cell lines such as colorectal HCT116 carcinoma or pancreatic ductal PANC813 adenocarcinoma.

The present invention also relates to a method of identifying a compound that modulates cellular cannibalism, comprising the step of measuring cell culture:
the expression level of a protein selected from the group consisting of p53 and N-terminal isoforms of p53 that lack the N-terminal transactivating domain, such as Δ40TP53 and Δ133TP53, and the extracellular amount of ATP,
wherein a compound that represses cellular cannibalism is identified by an increase in the expression levels of p53 or said isoforms, as compared to control levels, and a decrease in the extracellular amount of ATP, as compared to control levels.

In a preferred embodiment, the tested compound increases cellular cannibalism if the expression levels of p53 or said isoforms decrease, as compared to control levels, and if the extracellular amount of ATP increases, as compared to control levels.

More preferably, in this embodiment, said cell culture contains or consists of primary human diploid WI38 fibroblasts or cancer cell lines such as colorectal HCT116 carcinoma or pancreatic ductal PANC813 adenocarcinoma.

The present invention also relates to a method of identifying a compound that modulates cellular cannibalism, comprising the step of measuring in a cell culture:

the expression level of a protein selected from the group consisting of p53 and N-terminal isoforms of p53 that lack the N-terminal transactivating domain, such as Δ40TP53 and Δ133TP53, the expression level or the activity of the purinergic P2Y2 receptor and the extracellular amount of ATP, wherein a compound that represses cellular cannibalism is identified by an increase in the expression levels of p53 or said isoforms, as compared to control levels, and a decrease in both the extracellular amount of ATP, and in the expression level or the activity of the purinergic P2Y2 receptor, as compared to control levels.

In a preferred embodiment, the tested compound increases cellular cannibalism if the expression levels of p53 or said isoforms decrease, as compared to control levels, and if the extracellular amount of ATP increases as compared to control levels, and if the expression level or the activity of the purinergic P2Y2 receptor increases, as compared to control levels.

More preferably, in this embodiment, said cell culture contains or consists of primary Truman diploid WI38 fibroblasts or cancer cell lines such as colorectal HCT116 carcinoma or pancreatic ductal PANC813 adenocarcinoma.

In a preferred embodiment, measuring expression levels of the p53 isoforms protein or of the P2Y2 receptor comprises measuring the mRNA levels of these proteins. In a more preferred embodiment, measuring expression levels of the p53 isoform protein or of the P2Y2 receptor comprises using a transcriptional fusion between said p53 isoform or receptor and a reporter molecule.

In Vitro Methods for Detecting Cannibalism Behavior of a Cell

So far, this activity was commonly assessed by studying the cells under the microscope (by immunofluorescence or immunohistochemistry) and by visually detecting cell engulfment events or cell-in-cell systems.

The present inventors have shown in the experimental part of the present application that it is possible to detect early events of a cannibalism behavior of a cell, by measuring, in said cell, the expression level of a protein selected from the group consisting of: p53, p53β, p53γ, and N-terminal isoforms of p53 that lack the N-terminal transactivating domain, such as Δ40TP53 and Δ133TP53, or by measuring the expression level or the activity of the purinergic P2Y2 receptor, and/or by measuring the extracellular ATP secreted by said cells.

Study of these molecular pathways therefore results in a fine analysis of the ea mechanisms resulting in cannibalistic activity, before the morphologic events usually attributed to engulfing activity can be observed.

Thus, in another aspect, the present invention relates to an in vitro method for detecting cannibalism behavior of a cell, comprising the step of measuring in said cell:

the expression level of a protein selected from the group consisting of p53 and N-terminal isoforms of p53 that lack the N-terminal transactivating domain, such as Δ40TP53 and Δ133TP53, and/or the expression level or the activity of the purinergic P2Y2 receptor, and/or secreted extracellular ATP, and/or the expression level of a protein selected from the croup consisting of p53β and p53γ, wherein the said cell has cannibalism activity if the expression levels of p53 or said Δ40TP53 and Δ133TP53 isoforms is low, and/or if secretion of extracellular ATP is high, and/or if the expression level or the activity of the purinergic P2Y2 receptor is high, and/or if the expression level of p53β or p53γ is high, as compared to control levels.

Preferably, the said cell has no cannibalism activity if the expression levels of p53 or said Δ40TP53 and Δ133TP53 isoforms is high, and/or if secretion of extracellular ATP by said cell is low, and/or if the expression level or the activity of the purinergic P2Y2 receptor is low, and/or if the expression level of p53β or p53γ is low, as compared to control levels.

In a preferred embodiment, the method of the invention further comprises the step of measuring at least one senescence marker, for example selected from the group consisting of: $p21^{WAF1}$, Ki67, p16, Rb, and SA-β-Gal. It is also possible to detect the senescent morphology of the cells by microscopic analysis, for example the increase of cell and nuclear sizes, the detection of senescent associated heterochromatin foci or cell autophagy or the markers of growth arrest (for example an increase in p16), or the secretion of senescent associated secreted proteases (SASP), or markers of DNA damage responses (g-H12AX, ATMS1981P, p53BP1, etc.).

Thus, in a more preferred embodiment, the present invention relates to an in vitro method for detecting simultaneously cannibal and senescent behavior of a cell, comprising the step of detecting cellular cannibalism markers as mentioned in the present application and senescent markers disclosed above. More precisely, said method comprises the step of measuring, in said cell:

the expression level of a protein selected from the group consisting of p53 and N-terminal isoforms of p53 that lack the N-terminal transactivating domain, such as Δ40TP53 and Δ133TP53, and/or the expression level or the activity of the purinergic P2Y2 receptor, and/or secreted extracellular APT, and/or the expression level of a protein selected from the group consisting of p53β and p53γ, and the expression level of at least one senescence marker such as $p21^{WAF1}$, Ki67, p16, Rb, or SA-β-Gal, wherein the said cell has cannibal activity and undergo senescence if the expression levels of p53 or said Δ40TP53 and Δ133TP53 isoforms are low, and/or if secretion of extracellular ATP is high, and/or if the expression level or the activity of the purinergic P2Y2 receptor is high, and/or if the expression level of p53β or p53γ is high, and if the expression level of the senescence markers $p21^{WAF1}$, p16, and/or SA-β-Gal is high or if the expression level of the senescence markers Ki67 and/or Rb is low compared to control levels.

In another aspect, the present invention relates to an in vitro method of determining an increase in the propensity of a cell to be a target of cellular cannibalism.

The present inventors have indeed observed that any of the following events: (a) increased extracellular release of ATP, (b) decreased p53 expression, (c) decreased Δ133TP53 expression, (d) increased expression of p53β or p53γ, (e) increased expression of P2Y2 purigenic receptors, induces an increase in the propensity of a cell to be a target of cellular cannibalism.

As used herein, the expression "increase in the propensity of a cell to be a target of cellular cannibalism" means that there is an increase in the "eat-me" signals emitted by the cells. These signals are for example extracellular nucleotides such as ATP or UTP, that are known signals for cell engulfment.

In a preferred embodiment, measuring the expression levels of the said proteins comprises measuring their mRNA levels, for example by qPCR or by in situ hybridization. Also, secreted ATP is preferably measured by HPLC or luciferase assays. In addition, biological activity of P2Y2R is preferably measured by determining the phosphorylation of Pyk2 on tyrosine 402 (Séror et al. *The Journal of experimental medicine* 2011).

In Vitro Methods for Inducing Cellular Cannibalism in a Cell

The present inventors identified for the first time that low levels of p53, of Δ133TP53 or of Δ40TP53 promotes cellular cannibalism.

In another aspect, the present invention furthermore relates to a method of inducing cellular cannibalism in a cell in vitro, comprising inhibiting in said cell the expression of p53 or of an N-terminal isoform of TP53 selected from Δ133TP53 and Δ40TP53.

This inhibition may be obtained by inhibiting the formation of the said proteins (e.g., by inhibiting the transcription of DNA to mRNA or the translation of mRNA to a protein), or by promoting the degradation of these proteins by any conventional means.

In particular, said expression inhibition may be mediated by inhibiting the translation of mRNA to a protein by means of a miRNA or a siRNA.

More specifically, the invention relates to double strand siRNAs of approximately 15 to 30 nucleotides, preferably 19 to 25 nucleotides, or preferably around 19 nucleotides in length that are complementary (strand 1) and identical (strand 2) to nucleotide regions of the p53 isoforms implicated in the methods of the invention. These siRNAs of the invention also comprise a dinucleotide TT or UU at the 3' end. Numerous computer programmes are available for the design of the siRNAs of the invention.

In one particular embodiment, the siRNAs of the invention are tested and selected for their capability of reducing, even specifically blocking the expression of one particular p53 isoform, affecting as little as possible the expression of the other isoforms. For example, the invention concerns siRNAs allowing a reduction of more than 80%, 90%, 95% or 99% of the expression of one p53 isoform, and no reduction or a reduction of less than 50%, 25%, 15%, 10% or 5% or even 1% of the other isoforms of p53.

In a preferred embodiment, said p53 expression inhibition is achieved by using the siRNA of SEQ ID:17 (siRNA-: 5'GACUCCAGUGGUAAUCUAC 3') or SEQ ID NO:18 (siRNA-2: 5'GCAUGAACCGGAGGCCCAU3').

In another preferred embodiment, said Al 33T1³53 expression inhibition is achieved by using the siRNA of SEQ IL) NO:19 (siRNA-1: 5'UGUUCACUUGUGCC-CUGACUUUCAA3') or SEQ IL) NO:20 (siRNA-2: 5'CUUGUGCCCUGACUUUCA3').

These various siRNAs and miRNAs can be used for inducing simultaneously cell cannibalism and senescence in cancer cells. Consequently, they can be used for enhancing the survival of a patient suffering from cancer and, eventually, for treating cancer.

The present invention therefore also relates to the use of these siRNAs and miRNAs for the preparation of a pharmaceutical composition which is intended to treat cancer. Said pharmaceutical composition contains for example the said siRNAs or miRNAs and a pharmaceutically acceptable vehicle as defined above.

In other words, the present invention relates to a method for treating cancer, comprising the step of administering, in a patient suffering from cancer, an effective amount of any of the above-mentioned siRNAs or miRNAs.

These siRNAs can be injected into the cells or tissues by lipofection, transduction or electroporation.

In a related aspect, the present invention relates to a method of inhibiting cellular cannibalism in a cell in vitro, comprising inhibiting in said cell the expression of p53β or p53γ, or inhibiting the expression or the activity of the purinergic P2Y2 receptor, or inhibiting the secretion of extracellular ATP.

In a preferred embodiment, the expression of the isoforms p53β or p53γ, or of the purinergic P2Y2 receptor is inhibited by using a miRNA or a siRNA. P2Y2R expression inhibitors are for example disclosed in Seror C. et al., *The Journal of experimental medicine* 2011.

Again, these siRNAs can be double strand RNAs of approximately 15 to 30 nucleotides, preferably 19 to 25 nucleotides, or preferably around 19 nucleotides in length that are complementary (strand 1) and identical (strand 2) to nucleotide regions of the p53 isoforms p53β or p53γ or of the purinergic P2Y2 receptor. siRNAs inhibiting the expression of the P2Y2 receptor are for example those of SEQ ID NO:53 or of SEQ ID NO.54.

In one particular embodiment, the siRNAs of the invention are tested and selected for their capability of reducing, even specifically blocking the expression of p53β or p53γ, affecting as little as possible the expression of the other p53 isoforms. For example, the invention concerns siRNAs allowing a reduction of more than 80%, 90%, 95% or 99% of the expression of p53β or of p53γ, and no reduction or a reduction of less than 50%, 25%, 15%, 10% or 5% or even 1% of the other isoforms of p53.

Inhibition of P2Y2R biological activity can be obtained by using blocking agents such as low molecular weight antagonist (such as a small organic P2Y2R inhibitor kaempferol or other purinergic receptor antagonists including but not limited to reactive red 2, suramin, oxidized ATP, 8,8'-(carbonylbis(imino-3,1-phenylene carbonylimino)bis (1,3,5-naphthalenetrisulfonic acid) (also called NF023), 8,8'-(carbonylbis(imino-4,1-phenylenecarbonylimino-4,1-phenylenecarbonylimino))bis(1,3,5-naphthalenetrisulfonic acid) (also called NF279), Evans blue, trypan blue, reactive blue 2, pyridoxalphosphate-6-azophenyl-29,49-disulfonic acid (PPADS), isoquinoline sulfonamide, 1-[N,O-bis(5-isoquinoline-sulfonyl)-N-methyl-L-tyrosyl]-4-phenylpiperazine (also called KN-62), trinitrophenyl-substituted nucleotides (e.g., TNP-ATP), diinosine pentaphosphate (IP51), cicacron blue 3GA, 2'3'-O-(2,4,6-trinitrophenyl)-ATP, substance P (SP), basilen blue, and 4,4'-diisothiocyanostilbene-2,2'-disulfonic acid, or combinations, derivatives, or pharmaceutically acceptable salts thereof), blocking antibodies or aptamers or siRNAs.

In another preferred embodiment, the secretion of ATP is inhibited by blocking the membrane channels known to be involved in ATP transport (such as pannexin-1 and connexin-43) or by impairing biological mechanisms that are involved in same (such as autophagy or exocytosis) by means of conventional tools.

The present invention also concerns a therapeutic composition comprising a pharmaceutically acceptable vehicle and at least one of these compounds for its use for treating cancer.

Prognosis Methods Based on Detection of Cannibalism and Senescence

Cellular cannibalism and cell senescence were both shown to be involved in tumorigenesis. However, their precise role with this respect remains controversial.

On a one hand, cellular cannibalism was shown to promote tumor development. Tumor cell cannibalism has been therefore linked with poor tumor prognosis, what can be due to genomic instability induced in the polyploid cells (Krajcovic et al., 2011; Krajcovic and Overholtzer, 2012.

On another hand, cell senescence was shown to impair tumorigenesis (Canon C E, et EMBO Mol Med. 2012) or to promote same (Krajcovic et al., Nat Cell Idol 2011; Krajcovic and Overholtzer, Cancer Res 2012), so that the measure of senescence markers alone is of poor pronostic value.

The present inventors herein show for the first time that cellular cannibalism and senescence are tightly linked in human cancer and that the detection of both processes in cancer cells positively correlates with good patient's response to treatment. Importantly, their results provide the first evidence that detection of cellular cannibalism and senescence simultaneously in tumors helps for the diagnosis of disease outcomes and for the prediction of treatment efficiency against cancer diseases.

In another aspect, the present invention therefore relates to an in vitro method of determining the prognosis of cancer in a patient, comprising the step of simultaneously detecting the cannibal and senescent behavior of the tumor cells of this patient. As a matter of fact, if the said tumor cells have simultaneously high cannibal and senescent activities, then the said tumor cells will be of good prognosis and the patient survival is likely to be long. In contrast thereto, if the said tumor cells have low (or no) cannibal and senescent activities, then the said tumor cells will be of bad prognosis and the patient survival is likely to be short.

In this aspect, the said method preferably comprises the step of measuring the expression levels of p53 or of one of its isoforms Δ133TP53, TP53β, TP53γ, or Δ40TP53, or the expression level or the activity of the purinergic P2Y2 receptor, and the expression level of a senescence marker such as $p21^{WAF1}$, Ki67, p16, Rb, or SA-β-Gal, or of any other senescence marker as described above, in tumor cells isolated from the patient.

In fact, if the expression levels of p53 or said Δ40TP53 and Δ133TP53 isoforms in said tumor cells are low, or if the expression level or the activity of the purinergic P2Y2 receptor in said tumor cells is high, or if the expression level of p53β or p53γ in said tumor cells is high compared to control levels, and, simultaneously, if the expression level of the senescence markers $p21^{WAF1}$, and/or SA-β-Gal is high or if the expression level of the senescence markers Ki67 and/or Rb is low, then said tumor cell has high cannibal activity and undergo senescence, what is of good prognosis value for the patient.

In a preferred embodiment, the said method comprises the step of measuring the expression levels of p53 or of Δ133TP53, or the expression level or the activity of the purinergic P2Y2 receptor, and the expression level of a senescence marker such as $p21^{WAF1}$, Ki67 p16, Rb, or SA-β-Gal, or of any other senescence marker as described above, in tumor cells isolated from the patient.

In a more preferred embodiment, the said method comprises the step of measuring:
the expression levels of p53 or of Δ133TP53, and
the expression level or the activity of the purinergic P2Y2 receptor, and
the expression level of a senescence marker such as $p21^{WAF1}$, Ki67, p16, Rb, or SA-β-Gal, or of any other senescence marker as described above, in tumor cells isolated from the patient.

In another aspect, the present invention also relates to an in vitro method of determining the susceptibility of tumor cells to an anti-cancer treatment, comprising the step of detecting concomitantly the cannibal and senescent behavior of the said cells by means of the method of the invention, as defined above. As a matter of fact, if the said tumor cells exhibit simultaneously high cannibal and senescent activities after treatment, then the said tumor cells will be sensitive to the said anti-cancer treatment. In contrast thereto, if the said tumor cells have high cannibal activity but low or no senescent activity after treatment, then the said tumor cells will be resistant to the said anti-cancer treatment.

By "concomitantly" or "simultaneously", it is herein meant that the target processes occur in the cells from the same tumor. In particular, by using these terms, it is herein meant that the detection is performed in cells issued from the same tumor or patient, for example, from two tumor samples obtained from the same patient. As used herein, these terms do not mean that the measuring steps should be performed at the very same time, but rather on cell samples obtained from the same patient, preferably from the same tumor.

Said anti-cancer treatment is preferably a radiotherapeutic treatment, a chemotherapeutic treatment, an immunotherapeutic treatment, or a combination of same.

In these prognosis methods, the said tumor cells express normal levels or high levels of non-imitated p53.

In these prognosis methods, the said cancer is preferably selected in the group consisting of: melanoma, spitz tumors, prostate cancer, colon carcinoma, and liver carcinoma, breast cancer, lung cancer, cervical cancer, and bone cancer.

In another aspect, the present invention relates to treating methods comprising the steps of:
Determining the susceptibility of tumor cells to a defined anti-cancer treatment, by means of the prognosis method of the invention, and, if said tumor cells exhibit simultaneously high cannibal and senescent activities after treatment, then maintaining the said anti-cancer treatment.
Whereas, if said tumor cells have high cannibal activity but low or no senescent activity after treatment, then another anti-cancer treatment is to be administered.

For example, if the patient is treated with a defined chemotherapeutic treatment, determining the susceptibility of tumor cells to said treatment by means of the method of the invention will enable the skilled person to decide if the said chemotherapy is required or if it would be advantageous to replace—or to combine—it with radiotherapy or with another chemotherapeutic treatment.

In a particular aspect, the present invention relates to an in vitro method of determining the resistance of tumor cells to an anti-cancer treatment, comprising the step of detecting the cannibal and senescent behavior of the said cells by means of the method of the invention, as defined above. As a matter of fact, if the said tumor cells have high cannibal and senescent activities after treatment, then the said tumor cells will be sensitive to the said treatment. In contrast thereto, if the said cells have high cannibal activity but low or no senescent activity, then the said tumor cells will be resistant to the said anti-cancer treatment.

Said anti-cancer treatment is preferably a radiotherapeutic treatment, a chemotherapeutic treatment, an immunotherapeutic treatment, or a combination of same.

In this particular aspect, the said tumor cells preferably express mutated p53. These tumor cells are more preferably Triple Negative Breast Cancer (TNBC).

For this particular aspect, the present invention finally relates to treating methods comprising the steps of:
Determining the susceptibility of tumor cells to a defined anti-cancer e by means of the prognosis method of the invention, and, if said tumor cells exhibit simultaneously high cannibal and senescent activities after treatment, then maintaining the said anti-cancer treatment.
Whereas, if said tumor cells have high cannibal activity but low or no senescent activity after treatment, then another anti-cancer treatment is to be administered.

For example, if the patient is treated with a defined chemotherapeutic treatment determining the susceptibility of tumor cells to said treatment by means of the method of the invention will enable the skilled person to decide if the said chemotherapy required or if it would be advantageous to replace—or to combine—it with radiotherapy or with another chemotherapeutic treatment.

In a preferred embodiment, all the prognosis methods of the invention comprises a step of detecting the cannibalism and/or senescence behavior of the tumor cells on paraffin-embedded tumor tissue samples by immunohistochemistry.

EXAMPLES

Cells, Antibodies and Reagents.

Colorectal carcinoma. (Tp53$^{-/-}$ and Tp53$^{-/-}$) HCT116 cells were cultured in McCoy's 5A medium, Non small cell lung carcinoma H1299 (p53$^{-/-}$), H1975, H1650, cervix adenocarcinoma HeLa cells, ostocarcinoma U20S cells and human fibroblasts WI38 were cultured in Dulbecco's modified Eagle's medium (DMEM). Colorectal adenocarcinoma H1975 and H1650 cells and primary ductal carcinoma HCC1937 (p53$^{-/-}$) cells were in RPMI-1640 Medium. All medium were supplemented 10% FCS, 2 mM L-glutamine and 100 UI/ml penicillin/streptomycin (invitrogen). Head and neck squamous cell carcinoma SQ20B (p53$^{R273H}$) cells and pancreatic PANC813 cells were cultured as previously described. All medium were supplemented 10% FCS, 2 mM L-glutamine and 100 UI/ml penicillin/streptomycin (Invitrogen). Human primary keratinocytes were cultured using KGM-Gold™ BulletKit™ Kit (Lonza, 00192060). Antibodies for detection of ATM, ATR, BRCA-1, BRCA-2, β-catenin, cleaved caspase-3 (Asp175), FOXO-1, FOXO-3, FOXO-4 LKB1, p15INKb, p21$^{WAF1}$, 53BP1, MLC2, MLC2S19*, PAR-4, PTEN, Rb, TP73 were obtained from Cell Signaling Technology. Beclin-1, LAMP2, and TP53 (clone DO1) were from Santa Cruz. Antibodies against γ-H2AX and GAPDH were purchased from Millipore. Antibody against P2Y2 and TP53 (clone CM1) were respectively from Alomone laboratories and Leica. Constructs containing TP53$^{WT}$, TP53$^{NES-}$, TP53$^{NLS-}$, TP53$^{R175H}$, TP53$^{R273H}$ or EGFP and control were previously published (Tasdemir et al. 2008). Plasmids containing TP53β, TP53γ, Δ40TP53 and Δ133TP53 were obtained from Jean-Christophe Bourdon (University of Dundee UK).

RNA Interference.

Small interfering RNAs (siRNAs) specific for ATM (siRNA-1: 5'UGAAGUCCAUUGCUAAUCA3' and siRNA-2: 5'AACAUACUACUCAAAGACA3'), ATR (siRNA-1: 5'CCUCCGUGAUGUUGCUUGA3' and siRNA-2: 5' GCCAAGACAAAUUCUGUGU3'), BRCA1 (siRNA-1: 5' GCAACCUGUCUCCACAAAG3' and siRNA-2: 5'UGCCAAAGUAGCUAAUGUA3'), BRCA2 siRNA-1: 5'CUGAGCAAGCCUCAGUCAA3' and siRNA-2: 5'caacaauuacgaaccaaac3'), LKB1 (siRNA-1: 5'GGACUGACGUGUAGAACAA3' and siRNA-2: 5' GUCCUUACGGCAAGGUGAA 3'), p15INK4b (siRNA-1: 5CUCAGUGCAAACGCCUAGA3' and siRNA-2: 5'AACUCAGUGCAAACGCCUAGA3'), TP53 (siRNA-1: 5'GACUCCAGUGGUAAUCUAC3' and siRNA-2: 5'GCAUGAACCGGAGGCCCAU3'), TP63 siRNA-1: 5'CCAUGAGGUGAGCCgUGAAu3' and siRNA-2: 5'AGCAGCAAGUUUCGGACAG3'), TP73 (siRNA-1: 5'CCACGAGCUCGGGAGGGAC3' and siRNA-2: 5'ACGUCCAUGCUGGAAUCCG3'), Par-4 (siRNA-1: 5'GUGGGUUCCCUAGAUAUAA3' and siRNA2: 5'CAGCCGUUUGAAUAUAUUU3'), PTEN (siRNA-1: 5'GUCAGAGGCGCUAUGUGUA3' and siRNA-2: 5'CAC-CACAGUCUAGAACUUAU3'), Rb (siRNA-1: 5'GAAAGGACAUGUGAACUUA3' and siRNA-2: 5'CGAAAUCAGUGUCCAUAAA3'), p21WAF1 (siRNA-1: 5'CUUCGACUUUGUCACCGAG3' and siRNA-2: 5'CAGUUUGUGUGUCUUAAUUAU3'), Beclin-1 (siRNA-1:5'GAUUGAAGACACAGGAGGC3' and siRNA-2: 5'CCACUCUGUGAGGAAUGCACAGAUA3'), FOXO-1 (siRNA-1: 5'GCCCUGGCUCUCACAGCAA3' and siRNA-2: 5'CCGCGCAAGAGCAGCUCGU3'), FOXO-3 (siRNA-1: 5' GGGCGACAGCAACAGCUCU3' and siRNA-2: GGAUGACGUCCAGGAUGAU3'), FOXO-4 (siRNA-1: 5'CCCGACCAGAGAUCGCUAA3' and siRNA-2: 5'GGACAAGGGUGACAGCAAC3'), Δ133TP53 (siRNA-1: 5'UGUUCACUUGUGCCCUGAC-UUUCAA3' and siRNA-2: 5'CUUGUGCCCUGACUUU-CAA3'), P2Y2 (siRNA-1: 5' GGAUAGAAGAUGU-GUUGGG3' and siRNA-2: 5'GGCUGUAACUUAUACUAAA3') and control siRNA (5'-GCCGGUAUGCCGGUUAAGU3') were transfected 48 hours before coculture using Oligofectamine (invitrogen), according to manufacturer's instructions.

Pharmacological Inhibitions.

After inactivation of TP53 or Δ133TP53, primary human fibroblasts, primary human keratinocytes, colorectal carcinoma Tp53$^{+/+}$ HCT116 cells and pancreatic PANC813 cells were incubated during 24 hours in presence or in absence of indicated concentrations of the pharmacological inhibitor of purinergic P2Y2 receptor Kaempferol (Sigma), the pharmacological inhibitor of ROCK Y27632 (Sigma) or the pan-caspase inhibitor zVAD-fmk (100 uM, BD Biosciences), ATP, UTP and soluble apyrase used in indicated experiments were obtained from Sigma.

Immunoblots and Immunofluorescence.

Total cellular proteins were extracted in 250 mM NaCl-containing lysis buffer (250 mM NaCl, 0.1% NP40, 5 mM EDTA 10 mM Na$_3$VO$_4$, 10 mM NaF, 5 mM DTT, 3 mM Na$_4$P$_2$O$_7$ and the protease inhibitor cocktail (EDTA-free protease inhibitor tablets, Roche). Protein extracts (50 μg) were run on 4-12% SDS-PAGE and transferred at 4° C. onto a nitrocellulose membrane. After blocking, membranes were incubated with primary antibody at room temperature overnight. Horse radish peroxidase-conjugated goat anti-mouse or anti-rabbit (Southern Biotechnology) antibodies were then incubated during 1 h and revealed with the enhanced ECL detection system. After 48 hours of transfection with specific indicated siRNA, cells were stained with 10 μM of 5-chloromethylfluorescein diacetate (Cell Tracker Green CMFDA, Invitrogen) or with 10 μM of 5-(and-6)-(((4-Chloromethyl)Benzoyl)Amino)Tetramethylrhodamine (CMTMR, Invitrogen) and cocultured for indicated time. Time-lapse microscopy was performed on 35 mm on cover glass bottom dishes coated with poly-hema. Fluorescence and differential interference contrast (DIC) or phase contrast images were obtained every 5 min. For specific subcellular stainings of cannibal cells, cells were fixed in 4% paraformaldehyde/phosphate-buffered saline (PBS) for 30 minutes, permeabilized in 0.1% SDS in PBS and incubated with PCS for 20 minutes, as previously described (Seror et al., 2011). Antisera were used for immunodetection in PBS containing 1 mg/ml BSA and revealed with goat anti-rabbit IgG conjugated to Alexa 546 fluorochromes and with rabbit anti-mouse IgG conjugated to Alexa 647 fluorochromes from Invitrogen. Cells were counterstained with Hoechst 33342 (Invitrogen) and analyzed by fluorescent confocal microscopy on a Zeiss LSM510 using a 63×objective.

Electron Microscopy.

After co-culturing of cell for 24 h, cells were fixed in 1.6% glutaraldehyde in 0.1 M Sorensen phosphate buffer (pH, 7.3) for 1 h at 4° C. cells were washed one time with PBS and were refixed in aqueous 2% osmium tetroxide and finally embedded in Epon® epoxy resin, until imaging. Examination is performed at 80 kV under a transmission electron microscopy, on ultrathin sections (80 nm) stained with 0.1% lead citrate and 10% uranyl acetate.

Measurement of Extracellular ATP.

ATP release was determined using the Enliten ATP assay system (Promega) as described by the manufacturer. The luminescence was measured by integration over a 3-s time interval using the luminometer Fluostar OPTIMA (BMG Labtech).

Cell Proliferation Assay.

Cancer cell lines (HCT116 WT, HCT116 Tp $53^{-/-}$, $_{PANC}813$) that stably expressed green or red fluorescent proteins in their nuclei (GFP-histone H2B and RFP-histone H2B fusion proteins) were generated and were cocultured during 24 hours, optionally after depletion of Δ133TP53 to induce cell-in-cell internalization. Cell-in-cell structures were seeded in microtiter plates (with one single structure per well) by cell sorting using BD Influx™ cell sorter (Becton Dickinson). Sorted populations (single cell and cannibal cell) were validated under fluorescent microscope. Then, single cells and cannibal cells were cultured for seven days. During seven days, number of structure (single cell or cannibal cell) were quantified daily.

Detection of Senescence Associated β Galactosidase.

After co-culturing of 48 h, cells were fixed and stained using the senescence β-galactosidase staining kit (Cell signaling technologies) to detect senescence associated β galactosidase (SA-βGal) activity as previously described (Matsuura et al., 2007).

Cell Cycle Analysis.

To analyze cannibal cell proliferation, depleted cells were co-cultured for 24 h and then incubated with 10 μM 5-ethynyl-2'-deoxyuridine (EdU) for 1 h and stained using the Click-iT™ Edu Imaging Kit from Invitrogen. The cells were also counterstained with an antibody against β catenin and with Hoechst 33342 to identify cannibal cells and the nuclei were counterstained with Hoechst 33342 (Invitrogen).

Senescence Induction.

Oncogene-induced senescence (OIS) was performed by retroviral-mediated infection of primary human diploid fibroblasts (HDF) strain WI38 (population doubling 13) using pBABE-RAS$^{V12}$ and Phoenix packaging cells. Twenty four hours post-infection, cells were pharmacologically selected with 4 μg/ml puromycin (pBABE) for 2 days. Day 0 is considered when all non-infected cells were dead after pharmacological selection. Replicative senescent cells were produced by serial passaging of HDFs at normoxic oxygen conditions of 3% until replicative exhaustion. Cell populations were considered senescent when less than one population-doubling was completed per two weeks, EdU positivity was less than 1% and SA-b Gal positivity was greater than 70-80%.

Senescence Analysis.

Senescence was assessed using several assays. For growth curves, cells were plated in triplicates at 2.0×10$^4$ per well in 12-well plates. Relative cell numbers were estimated at various time-points using a crystal violet incorporation assay and population doublings (PD) were calculated using the following equation: n=(log10$^F$ log10$^I$)×3.32 (with n=PD, F=number of cells at the end of one passage, 1=number of cells that were seeded at the beginning of one passage). For life-span studies, cells were sub-cultured when 70-80% confluent at 2×104/cm2. Proliferative capacity was assessed by labeling cells for 24 hours EdU. These cells were also co-stained for SA-β Gal.

Tumor patient selection. Breast cancer patients were treated with 3 cycles of anthracycline and 3 cycles of docetaxel followed by surgery. As previously published (Chevallier et al, 1990), "Responders" exhibited a complete pathological response with only few residual cancer cells (Chevallier score ≤1). "Non Reponders" (Chevallier score ≥2) exhibited invasive primary tumors or lymph node metastases.

Histology and immunochemistry. Samples from recovered tumors, mammary gland tissues and human breast adenocarcinoma were fixed with 4% PFA for 4 h and then embedded into paraffin. Sections of 10 μm were fixed and stained with haematoxylin and eosin (HE) according to standard protocols. For b-catenin Lamp2 and p21$^{WAF1}$ immunochemistry antibodies used are described in "Cells, antibodies and reagents" section.

Statistical analysis. To determine statistical significance, Student's t-test was used for calculation of P values.

Results

Identification of tumor suppressive protein p53 as a repressor of cellular cannibalism. To identify the molecular basis of cancer-related cellular cannibalism, we determined the impact of the inactivation of 16 tumor suppressor proteins on cell internalization, the first step of cellular cannibalism. Among several cancer cell lines that spontaneously manifest cellular cannibalism (FIG. 6A), we chose the colon carcinoma HCT116 cell line to determine cell internalization after inactivation of tumor suppressor proteins involved in cell cycle regulation (LKB1, PTEN, Rb and p15INK4b), DNA repair (BRCA-1 and BRCA-2), DNA damage responses (ATM and ATR) and cell death regulation (FOXO-1, FOXO-2, FOXO-3, Beclin-1, Par-4, TP53, TP63 and TP73). After tumor suppressor knockdown, half of the cells were labeled with 5-chloromethylfluorescein diacetate (CMFDA, green fluorescence) and the other half with 5-(and-6)-(((4-Chloromethyl)Benzoyl)Amino)Tetramethylrhodarnine (CMTMR, red fluorescence), mixed together, and cultured for 24 hours (FIG. 1A and FIGS. 6B-Q). Subsequent, confocal microscopy revealed that depletion of TP53 resulted in a significantly enhanced frequency of cell-in-cell structures (FIGS. 1B and 1C). Cell internalization was confirmed by immunostaining of membrane-bound catenin revealing that one engulfing cell ("cannibal") can internalize more than one—up to six—cells ("targets") (FIG. 1D and FIG. 7A), Neither CMFDA nor CMTMR did affect the frequency of cell-in-cell structures (not shown) or the propensity of cells to act as cannibals or targets (FIG. 1E), although they provided a better resolution for the detection of cellular cannibalism than classical immunohistochemistry staining (FIG. 7B). Time-lapse microscopy of CMFDA/CMTMR-labelled, TP53-depleted cells demonstrated that cellular internalization occurred without morphological signs of apoptosis (such as membrane blebbing and formation of apoptotic bodies) (FIG. 7C), in line with an absent activation of caspase-3 (FIG. 7D). The internalization step was not related in its timing to symmetric or asymmetric mitoses of p53 depleted cells (FIG. 7E). Pharmacological inactivation of TP53 with cyclic by pifithrin-α (FIG. 1F,G), siRNA-mediated depletion of TP53 (FIGS. 1F-I), or knockout of the Tp53 gene by homologous recombination (FIG. 1F,G) induced cell-in-cell structures in HCT116 cells (FIG. 1F,G), as well as in human primary fibroblasts (FIG. 1H,I). Irrespective of the method of TP53 inactivation, inhibition of the serine threonine kinase ROCK by Y26732 (Overholtzer et al., 2007), prevented the generation of cell-in-cell structures (FIGS. 1F-I and FIGS. 2F-I), which however were not affected by the pan-caspase inhibitor Z-VAD-fmk (FIGS. 1F-I). Overall, our results identified a novel role for TP53 as a repressor of cellular cannibalism.

Δ133p53 is required for cellular cannibalism repression. Next, we used a battery of p53 mutants and isoforms to explore the mechanisms that govern the TP53-mediated regulation of cellular cannibalism. Wild type, full-length TP53, as well as a purely nuclear TP53 mutant (which lacks the nuclear export sequence, NES) were able to repress the formation of cell-in-cell structures, while a purely cytoplasmic TP53 mutant (which lacks a nuclear localization sequence, NLS) or two mutants that lack the transactivation activity of TP53 (due to frequent, cancer-associated mutations: R175H or R273H were unable to repress the cannibalistic activity (FIG. 2A-D). All TP53 splice variants that differ in the start codon and hence in their N-terminus (TP53β, TP53γ, Δ40TP53 and Δ133TP53), including the shortest version (Δ133TP53), which lacks the amino-terminal trans ovation and prolin-rich domains, were able to inhibit cannibalism (FIG. 2E,F). More importantly, selective depletion of Δ133TP53 with two distinct siRNAs that do not affect any other isoforms (FIG. 2G, (Fujita et al., 2009)) could induce cannibalism in several distinct cancer cell lines (HCT116, PANC) and primary human fibroblasts (FIG. 2H-L, FIG. 8A,B), Knockdown of all TP53 isoforms or that of Δ133TP53 alone similarly induced cannibalism.

In order to determine cellular consequences of Δ133p53 depletion, siRNA mediated knock down of Δ133p53 isoform from human colon HCT116 cells (FIG. 2G-I), human pancreatic PANC813 cells (FIG. 2J) or from human normal WI39 fibroblasts (FIG. 2K,L) was performed during 48 hours. Then, control and depleted cells were labeled with either CMFDA or CMTMR, mixed together and cultured during 24 hours. Confocal microscopy analysis of these experiments revealed that reduction of Δ133TP53 expression induced ROCK-dependent and caspase-independent cannibalism in cancer cells (HCT116 and PANC) (FIG. 2I,J), but also in normal human fibroblasts (WI39) (FIG. 2L). Next, we examined whether TP53 and Δ133TP53 act on cannibal cells or target cells. CMFDA-labeled (green) WT HCT116 cells (which express TP53) were co-cultured with CMTMR-labeled (red) cells that were manipulated for p53 expression: either WT cells transfected with s control siRNA, WT cells depleted from TP53 or Δ133IP53 only, or Tp53$^{-/-}$ cells. In this system, the absence of TP53 or Δ133TP53 alone enhanced the frequency of green-in-red cell structures, but not that of red-in-green figures (FIG. 2M). Hence, TP53 and Δ133TP53 act on the side of cannibal cells, not that of target cells, meaning that they increase the activity of cellular internalization on the side of the engulfing (not the engulfed) cell.

Extracellular ATP and P2Y2 purinergic receptors contribute to cannibalism. Stressed and dying cells can expose 'come get me' and 'eat me' signals or lose 'don't eat me' signals, thus facilitating their engulfment by neighboring cells (Grimsley and Ravichandran, 2003). The nucleotide ATP is released by stressed or dying cells and constitutes a potent chemotactic signal (Ravichandran, 2011) that can contribute to cell-to-cell contacts and fusions (Seror et al., 2011; Trautmann, 2009). Accordingly, tp53$^{-/-}$ cells (FIG. 3A), as well as irradiated or CDDP treated cells (FIG. 11B) and TP53 or Δ133TP53 depleted cells (FIG. 11C) released ATP shortly after treatments (FIG. 11B) or during coculture (FIG. 3C and FIG. 11C). These processes require ROCK signaling pathway (FIG. 11B-D). Importantly, addition of recombinant apyrase, an enzyme that degrades ATP and ADP to AMP, reduced cellular internalization induced by the depletion of TP53 or Δ133TP53 in HCT116 (FIG. 3B). Conversely, supplementation with ATP or UTP strongly enhanced the ROCK-dependent generation of cell-in-cell structures (FIG. 3C,D), confirming that these nucleotides can stimulate cellular cannibalism. Accordingly, the deletion or depletion of TP53 or Δ133TP53, respectively, enhanced the expression of the P2Y2 purinergic receptors (FIG. 3E,F), which are known to mediate ATP-dependent engulfment signals (Chekeni et al., 2010). In addition, 3% oxygen treated HDFs (FIG. 11F), senescent (FIG. 11G) and IR treated HEKns (FIG. 11H) and CDDP or IR treated cells (FIG. 11I) enhanced the expression of the P2Y2 purinergic receptors. Knockdown of this particular purinergic receptor by two non-overlapping siRNAs reduced cellular cannibalism resulting from TP53 inhibition or depletion in HCT116 cells (FIG. 3G), as well as in PANC813 cells (FIG. 3H). Pharmacological inhibition of the upregulated purinergic P2Y2 receptor also reduced the cannibalism of human primary fibroblasts depleted from TP53 or ΔA133TP53 (FIG. 3I-K) or stressed after replication (FIG. 11J). Considering that p53 acts on host cells to repress cellular cannibalism (FIG. 2M), we decided to determine whether p53 inactivation controls P2Y2 activity on target cell side or/and host cell side. We revealed that the depletion of P2Y2 receptors on host cells reduced the ROCK-mediated phosphorylation of light chain 2 of myosine (data not shown) and cellular cannibalism (FIG. 11K) demonstrating that the ATP-driven activation of P2Y2 receptors on host cells favors cellular cannibalism.

Cellular invasion triggers senescence of cannibal cells. Confirming prior reports on entosis that describe the fatal destiny of engulfed cells (Overholtzer et al., *Cell* 2007), internalized cells were targeted to LAMP2$^H$ lysosomal compartments for destruction, irrespective of the cell type that was analyzed (HCT116 or PANC813) after TP53 deletion or Δ133TP53 depletion (FIG. 9A-D), and cellular internalization was followed by nuclear degradation in an acidic compartment (FIG. 9E-G). In contrast cannibal cells conserved their viability. To investigate their long-term fate, we generated isogenic pairs of cancer cell lines HCT116WT, HCT116 Tp53$^{-/-}$, PANC813) that stably expressed green or red fluorescent proteins in their nuclei (GFP-histone H2B and RFP-histone H12B fusion proteins). Mixtures of such cells were cocultured, optionally after depletion of Δ133TP53 to induce entosis, and cell-in-cell structures were seeded in microtiter plates (with one single structure per well) and cultured for several days (FIG. 4A and FIG. 10A,B). In contrast to single control cells, cell-in-cell structured formed from CT116 WT or HCT116 Tp53$^{-/-}$ cells that were depleted from Δ133TP53 were unable to proliferate (and hence to increase their cell number), and demonstrated an increase in cell size and nuclear size, corresponding to an increase in ploidy (FIG. 4B,C). This correlated with reduced incorporation of the DNA precursor 5-ethynyl-2'-deoxyuridine (EdU), a thymidine analogue (FIG. 4C,D), increased staining of the nuclei from cannibal (but not target) cells with antibody recognizing phosphorylated histone H2AX (γH2AX DNA damage foci) (FIG. 4E,F) or p53BP1 (which also labels DNA damage foci (Lukas et al., 2011)) (FIG. 4E,F), and cytoplasmic senescence associated β-galactosidase (SA-β-Gal) activity (FIG. 4G,H), as well as expression of the cycline-dependent kinase inhibitory protein p21$^{WAF1}$ (FIG. 4I-K), siRNA-mediated depletion of p21$^{WAF1}$ reduced sings of senescence including SA-β-Gal staining (FIG. 4L-N) and allowed the cells to resume EdU incorporation (data not shown). According to the word entosis that defined a non-apoptotic cell death mechanism occuring after cell internalization, we termed this new modality of senescence induction, entescence.

Altogether, these results provide evidence for a link between Δ133p53 or p53 depletion, senescence and cellular cannibalism.

Senescence favors cannibalism. Oncogenic stress-induced senescence triggered by transducing primary human WI38 fibroblasts with Ras$^{V12}$ (FIG. 5A-C) led to an increase in P2Y2 expression (FIG. 5A), paralleling an increase in p16 and a loss of Rb expression, two phenomena that are known to be associated with senescence (Lowe et al., Nature 2004). In addition, Ras$^{V12}$ mediated retroviral transduction resulted in an increase in the frequency of cannibalistic events, allowing the Ras$^{V12}$-expressing fibroblasts to engulf HCT116 cells or normal non-senescent fibroblasts (FIG. 5B,C), through a process that depended on ROCK but not on caspases (FIG. 5C), Replicative stress induced by replicative exhaustion of HDFs at 3% normoxic oxygen conditions of upregulated P2Y2 (FIG. 5D) and stimulated cannibalism (FIG. 5E). Inhibition of P2Y2 receptors reduced the frequency of cannibalistic events induced by Ras$^{V12}$ (FIG. 5F). In addition, replicative senescence of human primary epidermal keratinocyte (HEKn) (Rivetti di Val Cervo et al., PNAS 2012) led to the induction of P2Y2 protein (FIG. 5G) and elevated cannibalism (FIG. 5H) requiring ROCK and P2Y2 (FIG. 5I). Prevention of cannibalism with inhibitors of ROCK or P2Y2 also reduced the frequency of senescent, SA-β-Gal-positive cells accumulating in aging cultures (FIG. 5J), These results support the ability of senescent cells to manifest a cannibalistic behavior and to engulf neighboring cells.

Entescence Contributes to Cellular Senescence Through P2Y2 Activation.

To further characterize the role of cellular cannibalism during senescence induction, we evaluated the impact of purinergic P2Y2 receptor activity on entescence and on cell autonomous senescence and observed that the pharmacological inhibition of purinergic P2Y2 receptor with kaempferol strongly reduced senescence observed during replicative stress of HEKns (FIG. 12A) or after treatment of HCT116 cells with IR or with MTX (FIG. 12B) as revealed by the reduction of the frequency of senescent, SA-β-Gal-positive cannibal cells (FIGS. 12A,B). Then, we evaluated the contribution of P2Y2 signaling pathways on p53 depletion induced entescence and revealed that P2Y2 depletion reduced significantly entescence detected after p53 deletion or depletion (FIG. 12C). These results were also confirmed after the depletion of the senescence regulator Δ133p53. As we previously described the depletion of Δ133p53 isoform from human colon HCT116 cells triggers cellular cannibalism (FIGS. 3I,J). Time lapse imaging of Δ133p53 depleted HCT116 cells that stably expressed GFP-histone H2B and RFP-histone H2B fusion proteins highlighted that once internalized target cells are degraded within less than one hour and then, cannibal cells increased their size and nuclear size (FIG. 12D). This process is associated with an increased staining of the nuclei from cannibal cells with antibodies recognizing γH2AX DNA damage foci (FIGS. 12E,G) or p21 (FIGS. 12E,H), and the induction of SA-β-Gal activity (FIGS. 12F,J) demonstrating that Δ133p53 depleted HCT116 cells undergo entescence. Depletion of p21 by two siRNA revealed reduced entescence (FIG. 4N), but also entescence associated cannibalism (FIG. 4O) highlighting that senescent cells and entescent cells are both able to internalize neighboring cells. We also demonstrated that P2Y2 depletion reduced specifically the frequency of cannibal cells showing for γH2AX positive nuclear foci (FIG. 5G), p21 expression (FIG. 5H) and SA-β-Gal activity (FIG. 5I) revealing that the purinergic P2Y2 receptor modulate cellular senescence by controlling the engulfment of neighboring cells. Taken together, these data demonstrated that entescence contributes to the establishment of cellular senescence.

Detection of Entescence In Vivo

Despite cell-in-cell cytological feature of cellular cannibalism has been detected in numerous human cancer, role of cellular cannibalism during oncogenesis was only recently studied (Overholtzer et al., Nature reviews Molecular cell biology 2008; Cano et al., EMBO Mol. Med. 2012) and depending on tumor microenvironment, could either contribute to tumor suppression through entosis induction {Overholtzer et al., Cell 2007; Cano et al., EMBO Mol. Med. 2012), but could also increase genomic instability of cannibal cells by modulating cytokinesis (Krajcovic et al., Nat Cell Biol. 2011), To validate our vitro based hypothesis demonstrating that cellular cannibalism is associated with senescence, we decided to determine whether human Spitz tumors that contain many senescent cells also show presence of cannibal cells. We analyzed human Spitz tumors and human aggressive melanomas using HE and immunofluorescence stainings and detected an increase of cannibal cells in Spitz tumor biopsies, as compared to aggressive melanoma (data not shown). In comparison to malignant melanomas which are known to be deleted or mutated for p16$^{INK4a}$ (Kamb et al, Nat Genet 1994), the majority of these begnin tumors contain senescent cells highlighting that cellular cannibalism is also associated with senescence in vivo. In addition, these results also suggest that induction of cellular cannibalism would determine the long-term survival of patients and animals to chemotherapy Schmitt et al. Nature reviews Cancer, 2003; Lowe et al., Nature 2004). To confirm this hypothesis, we determined whether cannibal cells detected on human breast adenocarcinoma could undergo senescence after neo-adjuvant treatment. First, we analyzed normal human breast and primary breast carcinoma biopsies using the previous experimental strategy and found that all biopsies revealed feature of cellular cannibalism (FIG. 13A and FIG. 13B), The frequency of cell engulfment was 10 fold higher in primary breast carcinomas (mean+/−SD=, n=30) than in normal tissues (mean+/−SD=, n=10) (FIG. 13C). To determine whether cellular cannibalism correlates with disease progression, we analyzed 10 biopsies of patients diagnosed with a grade 1, with a grade 2 or a grade 3 of breast carcinomas and observed that the frequency of cannibal cells significantly increased with the histological tumor grade (FIG. 13D). To precise the impact of cellular cannibalism on breast cancer progression, we wondered to know whether of neo-adjuvant treatments could increase cellular cannibalism and senescence of cannibal cells. We examined 30 biopsies of untreated breast carcinomas and 15 neo-adjuvant treated breast carcinomas for cell engulfment and we found no changes in the frequency of cannibal cells, but we observed cannibal cells with an increase in cell and nuclear sizes in neo-adjuvant treated tumor biopsies as compared to untreated (FIG. 13E a-c). Then, we stained sections from 30 untreated tumors and 15 treated tumors with for β-catenin and $p21^{WAF1}$ antibodies (FIG. 13F) and observed in half of neo-adjuvant treated tumors that single and cannibal cells are positive for $p21^{WAF1+}$ (FIG. 13G), confirming our previous results on Spitz tumors that cellular cannibalism and senescence are two interlinked processes that can also be detected in patients after neo-adjuvant treatments in vivo. Considering that breast carcinomas represent a heterogeneous group of tumors with different morphological and biological features, behavior and response to therapy, we compared the impact of cellular cannibalism and senescence on tumor and disease progressions between to distinct types of breast tumor that were treated with neo-adjuvant treatment. First, we determined the frequency of cellular cannibalism on breast tumor biopsies obtained from 26 patients with locally advanced breast cancers and observed that the efficiency of neo-adjuvant chemotherapy is associated with induction of cellular cannibalism (FIG. 14H). Cannibal cells detected in responder patients revealed evidences of cellular senescence (such as increase of their cellular and nuclear sizes, expression of $p21^{WAF1}$ and absence of Ki67 staining). In contrast, biopsies from non-responder patients revealed a strong reduction of cellular cannibalism and did not present signs of entescence or cellular cannibalism associated to senescence. More important, we found that the detection of cellular cannibalism is associated with an increase of disease free and overall survivals of treated patients (FIG. 14B and FIG. 14C) suggesting that the detection of cellular cannibalism (and more precisely senescence of cannibal cells) on biopsies obtained from breast tumors strongly predict response to nee-adjuvant treatment. Then, we determined whether the detection of cellular cannibalism in triple negative breast cancer tumors (TNBC) that are more aggressive tumors could also predict the efficiency of neo-adjuvant treatment. We evaluated the frequency of cannibal cells on 71 TNBC biopsies obtained after neo-adjuvant treatment and revealed that the detection of cellular cannibalism also predict the efficiency of neo-adjuvant treatment on TNBC patients, but with great interest in these tumors that harbor p53 mutation and don't undergo senescence, the accumulation of cellular cannibalism is associated with the absence of response to neo-adjuvant treatment (FIG. 14D) and a strong reduction of disease free survival and overall survival of treated patients (FIG. 14E and FIG. 14F). These results confirmed those obtained in FIG. 15 demonstrating that p53 mutations repress entescence and lead to the accumulation of cannibal polyploidy cells that are able to divide and restart proliferation.

Overall, these data obtained in vivo confirm that entescence or/and senescence associated to cellular cannibalism also occur in patients and their detections could help for the determination of disease outcomes and for the prediction of chemo- and radiotherapy efficiency.

Discussion

Here, we show that pharmacological and genetic inhibitions of TP53 or Δ133TP53 initiate cellular cannibalism by inducing ATP release and P2Y2 activation. After internalizing target cells, cannibal cells become senescent through $p21^{WAF1}$ induction. Once senescent, cannibal cells can also internalize other lived neighboring cells. These findings provide the first demonstration that cellular cannibalism may modulate tumor growth despite TP53 or Δ133TP53 expression is reduced.

Although sig ling pathways elicited by TP53 inactivation were extensively investigated, we show that ATP is released into the extracellular milieu during cell interactions between TP53 deficient cells or between Δ133TP53 depleted cells (FIG. 3A and data not shown) and that this extracellular ATP is required for cell internalization (FIG. 3B-D). Release of ATP by cells occurs through multiple mechanisms that may activate membrane channels eluding connexin and pannexin hemichannels) or induce exocytic or autophagic mechanisms Corriden and Inset, 2010). Autophagy also known as "self-eating" is a cellular response to multiple stresses that TP53 was recently identified as regulator of autophagy. Deletion, depletion and inhibition of TP53 can induce autophagy in human, mouse and nematode cells (Tasdemir et al., 2008), but autophagy is also required for ATP release from dying tumor cells during chemotherapy cells and contributes to immunogenicity. In this context, we postulated that release of ATP that we detected during culture of TP53 cells (FIG. 3A) or Δ133TP53 depleted cells (data not shown) could be initiated by autophagy. Further characterization of mechanisms that are required for ATP release will determine the role of autophagy in cellular cannibalism. During entosis, autophagy machinery was involved in the degradation of internalized cell (Florey et al., *Nat Cell Biol.* 2011; Florey and Overholtzer, *Trends Cell Biol.* 2012), but impact of autophagy on cell-in-cell structure formation remains to be investigated.

Once release, extracellular ATP can exert a wide range of cellular effects by activating plasma membrane bound receptors such as ionotropic purinergic P2X receptors and metabolotropic PINT receptors (Burnstock, *Cell Mol Life Sci.* 2007). In this study, we revealed that TP53 or Δ33TP3 knockdowns increase expression of heterotrimeric guanine nucleotide binding pro (protein G) coupled P2Y2 receptors in normal and in cancer (FIG. 3). More important, P2Y2 depletion impairs cell engulfment and reduces drastically educes frequencies of cell-in-cell structures detected after TP53 or Δ133TP53 inactivation, demonstrating that P2Y2 participates in the engulfment of neighboring cells by cannibal cells. Purinergic P2Y2 receptor contributes to actine cytoskeleton rearrangement that is required for cell interactions and cell fusion (Paoletti et al., *PNAS* 2012; Seror et al., 2011) and increases mobility of cells through activation of Rho and formation of Rho dependent stress fibers (Bagchi et al., 2005; Chen et al., 2006; Liao et al., 2007; Liu et al., 2004). Indeed, depletion of TP53 changes the morphology and the polarity of cells (Gadea et al., 2007; Gadea et al., 2002; WO et al., 2003), but also increases mobility in numerous cell types (including keratinocytes and colon cancer HCT116 cells) (Lefort et al., 2007; Sablina et al., 2003). Evidences that signaling pathways modulating cell migration and chemotaxis are influenced by TP53 have been also produced (Gadea et al., 2007; Gadea et al., 2002; Guo and Zheng, 2004; Lefort et al., 2007; Roger et al., 2006; Xia and Land, 2007), demonstrating that TP53 loss drives increased activity of Rho/ROCK axis to promote cell mobility and invasion during tumor progression. Additional experiments have to be developed to determine the link between extracellular ATP and purinergic P2Y2 activation, and Rho/ROCK dependent signaling pathways during cellular cannibalism. Our results suggest that after TP53 or Δ133TP53 depletion, extracellular ATP and purinergic P2Y2 receptors activation may enhance mobility of cannibal cells and favor engulfment of neighboring cells.

Cellular cannibalism was initially described as non apoptotic cell death that is provoked by loss of attachment to extracellular matrix and led to destruction of internalized cells through lysosomal degradation. This atypical cell death modality was defined as mitosis and was proposed as a new tumor suppressor mechanism to control tumor growth and metastatic dissemination (Overholtzer et al., 2007). More recently, studies on cellular cannibalism demonstrated that internalizing cells (that we previously defined as cannibal cells) cause a cytokinesis failure of cannibal cells by disrupting the formation of the contractile ring during cannibal cell division. Hence, cellular cannibalism initiates a non-genetic mechanism of cytokinesis failure and increase genomic instability by generating aneuploidy cells (Krajcovic et al., 2011; Krajcovic and Overholtzer, 2012). Here we demonstrated that cell engulfment induces hyperploidy and senescence of cannibal cells when TP53 or Δ133TP3 is reduced. Senescence is a stable cell cycle arrest that is induced at the end of the cellular lifespan or in response to different stresses (such as replicative or oxidative stresses, DNA damage, chemotherapeutic drugs). No specific markers for senescence have been identified, but senescent status of cells is determined by detecting an irreversible growth arrest, the expression of the cytoplasmic senescence associated β-galactosidase (SA-βGal), the re-expression of cell cycle inhibitors (such as $p16^{INK4a}$ or $p21^{WAF1}$), the secretion of numerous growth factors, cytokines and proteases; and by the presence of nuclear foci that contain DNA damage response (DDR) proteins or heterochromatin. We found that cannibal cells showed an irreversible growth arrest, expressed cytoplasmic senescence associated β-galactosidase (SA-β-Gal) activity and the cycline-dependent kinase inhibitory protein $p21^{WAF1}$. We also detected DDR foci in the nuclei of cannibal cells demonstrating, that in absence of TP53 or Δ133TP53, cancer cells become senescent after cell engulfment. Although transcriptional activity of TP53 is frequently required for the induction of senescence, we unrevealed that senescence induction occurs in absence of TP53 or its Δ133TP53. Our results were in accord with previously published reports demonstrating that cellular senescence may be induced in melanoma in absence of TP53 (Ha et al., 2007; Ha et al., 2008) or by ARF independent TP53 signaling pathways (Lin et al., 2010). Recently, decrease of Δ133TP53 and overexpression of TP53l3 participate to replicative senescence, but not oncogene induced senescence (Fujita et al., 2009), In addition, we also detected on cannibal cells, DNA damage responses (as revealed by nuclear foci containing γ-H2AX and 53BP1) and $p21^{WAF1}$ over-expression two cellular processes that are required for replicative or oncogenic senescence. Inhibition of p21 expression reduced senescence of cannibal cells depleted for TP53 or for Δ133TP53, suggesting that $p21^{WAF1}$ overexpression is induced through TP53-dependent or independent mechanisms. Cellular senescence is a crucial barrier to tumor progression in vivo (Kuilman et al., 2010), Understanding molecular and cellular basis of senescence represent a crucial step to fight cancer and develop therapeutic strategies (such as pro-senescent therapy (Nardella et al., 2011)) to reduce tumor growth and metastatic dissemination, Here, we highlighted a new mechanism for tumor suppression that could be enhanced for therapeutic benefits when TP signaling pathways are impaired.

BIBLIOGRAPHIC REFERENCES

Bagchi S, Liao Z, Gonzalez F A, Chorna N E, Seye C T, Weisman G A, Erb L. The P2Y2 nucleotide receptor interacts with alphav integrins to activate Go and induce cell migration. Biol Chem. 2005 Nov. 25; 280(47):39050-7.

Bensaad K, Tsuruta A, Selak M A, Vidal M N, Nakano K, Bartrons R, Gottlieb E, Vousden K. H. TIGAR, a p53-inducible regulator of glycolysis and apoptosis. Cell, 2006 Jul. 14; 126(1):107-20.

Bourdon J C. p53 and its isoforms in cancer. Br J Cancer. 2007 Aug. 6; 97(31:277-82.

Burnstock G. Purine and pyrimidine receptors. Cell Mol Life Sci. 2007 June; 64(121:1471-83.

Cano C E, Sandi M J, T, Calvo E L, Turrini O, Bartholin L. Loncle C, Secq V, Garcia S, Lomberk G, Kroemer G, Urrutia R, Toyama J L. Homotypic cell cannibalism, a cell-death process regulated by the nuclear protein 1, opposes to metastasis in pancreatic cancer. EMBO Mol Med. 2012 September; 4(9):964-79

Cartier-Michaud A, Malo M, Charrièrc-Bertrand C, Gadea G, Anguille C, Supiramaniam A, Leslie A, Delaplace F, Hutzler C I, Roux P, Lawrence D A. Barlovatz-Meimon G. Matrix-bound PAI-1 supports cell Webbing via RhoA/ROCK1 signaling. PLoS One, 2012; 7(2):e32204.

Faraaz B. Chekeni, Michael R. Elliott, Joanna K. Sandilos, Scott F. Walk, Jason M. Kinchen, Eduardo R. Lazarowski, Allison J. Armstrong, Silvia. Penuela, Dale W, Laird, Guy S. Salvesen, Brant E. Isakson, Douglas A. Bayliss, Kodi S. Ravichandran Pannexin 1 channels mediate 'find-me' signal release and membrane permeability during apoptosis. Nature. 2010 October 14; 467(7317): 863-867

Chen Y, Corriden R, Inoue Y, Yip L, Hashiguchi N, Zinkernagel A, Nizet V, Inset P A, Junger W G. ATP release guides neutrophil chemotaxis via P2Y2 and A3 receptors. Science. 2006 Dec. 15; 314(5806):1792-5.

B. Chevallier, V. Mosseri, J. P. Dance, P. Basin, J. P. Julien, B. Assault' A prognostic score in histological node negative breast cancer. *Br J Cancer.* 1990 March; 61(3): 436-440.

Jean-Philippe Coppe, Christopher K Patil, Francis Rodier, Yu Sun, Denise P Muñoz, Joshua Goldstein, Peter S Nelson, Pierre-Yves Desprez, Judith Campisi Senescence-Associated Secretory Phenotypes Reveal Cell-Nonautonomous Functions of Oncogenic RAS and the p53 Tumor Suppressor PLoS Biol. 2008 December; 6(12): e301.

Ross Corriden, Paul A. Insel.Basal Release of ATP: An Autocrine-Paracrine Mechanism for Cell Regulation. Sci Signal. 2010 January 12; 3(104): rel.

Demidenko, Z. N. et al. *Proceedings of the National Academy of Sciences of the United States of America* 107, 9660-9664 (2010).

Zoya N. Demidenko, Lioubov G. Korotchkina, Andrei V. Gudkov, Mikhail V. Blagosklonny. Paradoxical suppression of cellular senescence by p53. Proc Natl Acad Sci USA. 2010 May 25; 107(21): 9660---9664.

Fasanaro et al, Pharmacol. Then 2010; 125(1):92-104

Oliver Florey, Sung Eun Kim, Cynthia P. Sandoval, Cole M. Haynes, Michael Overholtzer. Autophagy machinery mediates macroendocytic processing and entotic cell death by targeting single membranes. Nat Cell Biol. 2011 October 16; 13(11): 1335-1343.

Oliver Florey, Michael Overholtzer. Autophagy proteins in macroendocytic engulfment Trends Cell Biol.2012 July; 22(7): 374-380.

Kaori Fujita, Abdul M. Mondal, Izumi Horikawa, Giang H. Nguyen, Kensuke Kumamoto, Jane J. Sohn, Elise D. Bowman, Ewy A. Mathe, Aaron J. Schetter, Sharon R. Pine, Helen Ji, Borivoj Vojtesek, Jean-Christophe Bourdon, David P. Lane, Curtis C. Harris. p53 isoforms, Δ133p53 and p53β, are endogenous regulators of replicative cellular senescence. Nat Cell Biol. 2009 September; 11(9): 1135-1142.

Gilles Gadea, Marion de Toledo, Christelle Anguilla Pierre Roux. Loss of p53 promotes RhoA-ROCK-dependent cell migration and invasion in 3D matrices. J Cell Biol. 2007 July 2; 178(1): 23-30.

Gadéa G, Lapasset L, Gauthier-Rouvière C, Roux P. Regulation of Cdc42-mediated morphological effects: a novel function for p53. EMBO J. 2002 May 15; 21(10):2373-82.

Gonzalez-Pastor J E, Hobbs E C, Losick R. Cannibalism by sporulating bacteria. Science. 2003 Jul. 25; 301(5632): 510-3.

Gottlieb E, Vousden K H. p53 regulation of metabolic pathways. Cold Spring Barb Perspect Biol. 2010 April; 2(4):a001040.

Grimsley C, Ravichandran KS. Cues for apoptotic cell engulfment: eat-me, don't eat-me and come-get-Inc signals. Trends Cell Biol. 2003 December; 13(12):648-56.

Guiral S, Mitchell T J, Martin B, Claverys W. Competence-programmed predation of noncompetent cells in the human pathogen *Streptococcus pneumoniae*: genetic requirements. Proc Natl Acad Sci USA. 2005 Jun. 14; 102(24):8710-5.

Guo F, Ciao Y, Wang L, Zheng Y.p19Arf-p53 tumor suppressor pathway regulates cell motility by suppression of phosphoinositide 3-kinase and Rac1 GTPase activities. Biol Chem. 2003 Apr. 18; 278(16):14414-9.

Ha L, Ichikawa T, Anver M, Dickins R, Lowe S. Sharpless N E, Krimpenfort P, Depinho R A, Bennett D C, Sviderskaya E V, Merlino G. ARF functions as a melanoma tumor suppressor by inducing p53-independent senescence. Proc Natl Acad Sci S A. 2007 Jun. 26; 104(26): 10968-73.

Ha L, Merlino G, Sviderskaya E V. Melanomagenesis: overcoming barrier of melanocyte senescence, Cell Cycle. 2008 Jul. 1; 7(13):1944-8.

Hanahan D, Weinberg R A, The hallmarks of cancer, Cell. 2000 Jan. 7; 100(1):57-70.

Hanahan D, Weinberg R A. Hallmarks of cancer: the next generation Cell, 2011 Mar. 4; 144(5) 46-74.

Jänicke R U, Sohn D, Schulze-Osthoff K. The dark side of a tumor suppressor: anti-apoptotic p53. Cell Death Differ. 2008 June; 15(6):959-76.

Kaghad M, Bonnet H, Yang A, Creancier L, Biscan J C, Valent A. Minty A, Chalon P, Lelias J M, Dumont X, Ferrara P, McKeon F, Caput D. Monoallelically expressed gene related to p53 at 1p36, a region frequently deleted in neuroblastoma and other human cancers. Cell. 1997 Aug. 22; 90(4):809-19.

Kamb A, Shattuck-Eiders D, Eeles R, Liu Q, Gruis N A, Ding W, Hussey C, Tran T, Miki Y, Weaver-Feldhaus J, et al, Analysis of the p16 gene (CDKN2) as a candidate for the chromosome 9p melanoma susceptibility locus, Nat Genet, 1994 September; 8(1):23-6.

Krajcovic M, Johnson N B, Sun Q, Normand G, Hoover N, Yao E, Richardson A L, King R W, Cibas E S, Schnitt S J, Brugge J S, Overholtzer M. A non-genetic route to aneuploidy in human cancers. Nat Cell Biol. 2011 March; 13(3):324-30.

Krajcovic M, Overholtzer M. Mechanisms of ploidy increase in human cancers: a new role for cell cannibalism. Cancer Res, 2012 Apr. 1; 72(7):1596-601.

Khoury M P, Bourdon J C. The isoforms of the p53 protein. Cold Spring Harb Perspect Biol. 2010 March; 2(3): a000927

Kuilman T, Michaloglou o 1/V J, Peeper D S. The essence of senescence. Genes Dev. 2010 Nov. 15; 24(22):2463-79.

Lefort K, Mandinova A, Ostano P, Kolev V, Calpini V, Kolfschoten I, Devgan V, Lieb J, Raffoul W, Hohl D, Neel V, Garlick J, Chiorino G, Dotto G P. Notch1 is a p53 target gene involved in human keratinocyte tumor suppression through negative regulation of ROCK1/2 and MRCKalpha kinases, Genes Dev. 2007 Mar. 1; 21(5):562-77, Li W, Baker N E. Engulfment is required for cell competition. Cell. 2007 Jun. 15:129(6):1215-25.

Li C. et al, *AAPSJ,* 2009; 11(4); 747-757

Liao Z, Seye C I, Weisman G A, Erb L. The P2Y2 nucleotide receptor requires interaction with alpha v integrins to access and activate G12. J Cell Sci. 2007 May 1; 120(Pt 9):1654-62.

Lin H K, Chen Z, Wang G, Nardella C, Lee S W, Chan C H, Yang W L, Wang J, Egia A, Nakayama K I, Cordon-Carlo C, Teruya-Feldstein J, Pandolfi P P. Skp2 targeting suppresses tumorigenesis by Arf-p53-independent cellular senescence. Nature. 2010 Mar. 18; 464(7287):374-9.

Liu J, Liao Z, Camden J, Griffin K D, Garrad R C, Santiago-Perez L I, Gonzalez F A, Seye C I, Weisman G A, Erb L. Src homology 3 binding sites in the P2Y2 nucleotide receptor interact with Src and regulate activities of Src, proline-rich tyrosine kinase 2, and growth factor receptors. J Biol Chem. 2004 Feb. 27; 279(9):8212-8.

Lowe, S. W., Cepero, E. and Evan, G. Intrinsic tumour suppression. Nature 432, 307-315 (2004).

Lukas C, Savic V, Bekker-Jensen 5, Foil C, Neumann B, Pedersen R S, Grofte N T, Chan K L, Hickson I D, Bartek J, Lukas J. 53BP1 nuclear bodies form around DNA lesions generated by mitotic transmission of chromosomes under replication stress. Nat Cell Biol, 2011 March; 13(3):243-53. doi:

Matsuura F, Hirano K, Ikegami C, Sandoval J C, Oku H, Yuasa-Kawase M, Tsubakio-Yamamoto K, Koseki M, Masuda D, Tsujii. K, Ishigami M, Nishida N I, Shimomura I, Hori M, Yamashita S. Senescent phenotypes of skin fibroblasts from patients with Tangier disease. Biochem Biophys Res Commun. 2007 Jun. 1; 357(2): 493-8. Epub 2007 Apr. 9.

Overholtzer, M., and Brugge, J. S. The cell biology of cell-in-cell structures, Nature reviews Molecular cell biology 9, 796-809. (2008)

Overholtzer, M., Maillcux, A. A., Mouncimne, G., Normand, G., Schnitt, S. J., King, R. W Cibas, E. S., and Brugge, J. S. (2007). A nonapoptotic cell death process, entosis, that occurs by cell-in-cell invasion. Cell 131, 966-979.

Paoletti, A., Raza, S. Q., Voisin, L., Law, F., Pipoli de Fonseca, J., Caillet, M., Kroemer, G., and Rivetti di Val Cervo, P., Lena, A. M., Nicoloso, M., Rossi, S., Mancini, M., Zhou, H., Saintigny, Dellambra, E., Odorisio, T., Mahe, C., et al. (2012). p63-microRNA feedback in keratinocyte senescence. Proceedings of the National Academy of Sciences of the United States of America 109, 1133-1138.

Parr CE. et al, 1994, PNAS 91(8):3275-9

Rivetti di Vat Cervo et al., Proc Natl Acad Sci USA. 2012 Jan. 24; 109(4):1133-8

Roger, L., Gadea, G., and Roux, P. (2000). Control of cell migration: a tumour suppressor function for p53 Biology of the cell/under the auspices of the European Cell Biology Organization 98, 141-152.

Sablina, A. A., Budanov, A. V., Ilyinskaya, Agapova, L. S., Kravchenko, J. E., and Chumakov, P. M. (2005). The antioxidant function of the p53 tumor suppressor. Nature medicine 11, 1306-1313.

Sablina, A. A., Chumakov, P. M and Karlin, B. P. 2003). Tumor suppressor p53 and its homologue p73alpha affect cell migration. The Journal of biological chemistry 278, 27362-27371.

Schmitt, C. A. (2003). Senescence, apoptosis and therapy-cuffing the lifelines of ca c-r. Nature reviews Cancer 3, 286-295.

Seror, C., Melki, M. T Subra, Raza, S. Q Bras, M Saidi, H., Nardacci, R., Voisin, L., Paolettim A., Law, F., et al. (2011). Extracellular ATP acts on P2Y2 purinergic receptors o facilitate HIV-1 infection. The Journal of experimental medicine 208, 1823-1834.

Tasdemir, E., Maiuri, Galluzzi, L., Vitale, I., Djavaheri-Mergny, M., D'Amelio, M., Criollo, A., Teodoro, J. G., Evans, S. K., and Green, M. R. (2007). Inhibition of tumor angiogenesis by p53: a new role for the guardian of the genome. J Mol Med (Berl) 85, 1175-1186.

Tolstonog, G. V., and Deppert, W. (2010). Metabolic sensing by p53: keeping the balance between life and death. Proceedings of the National Academy of Sciences of the United States of America 107, 13193-13194.

Vogelst B., Lane, D., and Levine, A. J. (2000). Surfing the p53 network. Nature 408, 307-310.

Vousden, K. H., and Lane, D. P. (2007) 53 in health and disease. Nature reviews Molecular cell biology 8, 275-283.

Vousden, K. H., and Lu, X. (2002). Live or let die: the cell's response to p53. Nature reviews Cancer 2, 594-604.

Vousden, K. H., and Prives, C. (2009). Blinded by the Light: The Growing Complexity of p53. Cell 137, 413-431.

Waddell, D, R., and Duffy, K. T. (1986), Breakdown of self/nonself recognition in cannibalistic strains of the predatory slime mold, Dictyostelium caveatum. The Journal of cell biology 102, 298-305

Xia, M., and Land, H. (2007). Tumor suppressor p53 restricts Ras stimulation of RhoA and cancer cell motility, Nature structural & molecular biology 14, 215-223.

Yang A, Kaghad M, Wang Y, Gillett E, Fleming M D, Dötsch V, Andrews N C, Caput D, McKeon F. p63, a p53 homolog at 3(127-29, encodes multiple products with transactivating, death-inducing, and dominant-negative activities. Mol Cell. 1998 September; 2(3):30546.

Yonish-Rouach, E., Resnitzky, D., Lotem, J., Sachs, L., Kimchi, A., and Oren, M. (1991). Wild-type p53 induces apoptosis of myeloid leukaemic cells that is inhibited by interleukin-6. Nature 352, 345-347.

The invention claimed is:

1. An in vitro method for detecting cannibalism behavior of a cell, comprising:
   measuring expression level of p53, expression level of a N-terminal isoform of p53 that lacks N-terminal transactivating domain, expression level of p53β, or expression level of p53γ in said cell, wherein measuring expression level comprises measuring mRNA level; and
   measuring activity of purinergic P2Y2 receptor (P2Y2R) in said cell by determining the phosphorylation of Pyk2.

2. The method according to claim 1, wherein the N-terminal isoform of p53 that lacks N-terminal transactivating domain is Δ40TP53 or Δ133TP53.

3. The method according to claim 1, further comprising measuring at least one senescence marker.

4. The method according to claim 3, wherein the senescence marker is p21WAF1, Ki67, p16, Rb, or SA-β-Gal.

5. The method according to claim 1, wherein said cell is a cancer cell.

6. The method of claim 5, wherein said cell is a melanoma, spitz tumor, prostate cancer, colon carcinoma, liver carcinoma, breast cancer, lung cancer, cervical cancer, or a bone cancer cell.

7. The method of claim 6, wherein said cell is a Triple Negative Breast Cancer cell.

8. The method of claim 1, wherein the measuring steps are performed on a paraffin-embedded tumor tissue sample comprising the cell.

9. The method according to claim 1, wherein measuring activity of P2Y2R in said cell comprises determining the phosphorylation of Pyk2 on tyrosine 402.

10. An in vitro method for detecting cannibalism behavior of a cell, comprising:
    measuring expression level of p53, expression level of a N-terminal isoform of p53 that lacks N-terminal transactivating domain, expression level of p53β, or expression level of p53γ in said cell; and
    measuring activity of purinergic P2Y2 receptor (P2Y2R) in said cell by determining the phosphorylation of Pyk2,
    wherein said cell is a cancer cell.

11. The method of claim 10, wherein said cell is a melanoma, spitz tumor, prostate cancer, colon carcinoma, liver carcinoma, breast cancer, lung cancer, cervical cancer, or a bone cancer cell.

12. The method of claim 11, wherein said cell is a Triple Negative Breast Cancer cell.

13. The method of claim 10, wherein the measuring steps are performed on a paraffin-embedded tumor tissue sample comprising the cell.

14. The method according to claim 10, wherein measuring activity of P2Y2R in said cell comprises determining the phosphorylation of Pyk2 on tyrosine 402.

15. The method according to claim 14, wherein measuring expression level comprises measuring mRNA level.

* * * * *

SEQUENCE LISTING

```
<160> NUMBER OF SEQ ID NOS: 55

<210> SEQ ID NO 1
<211> LENGTH: 1181
<212> TYPE: DNA
<213> ORGANISM: homo sapiens
<220> FEATURE:
<221> NAME/KEY: misc_feature
<223> OTHER INFORMATION: human p53 DNA  (NM_000546)

<400> SEQUENCE: 1
atggaggagc cgcagtcaga tcctagcgtc gagcccctc tgagtcagga aacattttca      60
gacctatgga aactacttcc tgaaaacaac gttctgtccc ccttgccgtc ccaagcaatg     120
gatgatttga tgctgtcccc ggacgatatt gaacaatggt tcactgaaga cccaggtcca     180
gatgaagctc ccagaatgcc agaggctgct cccccgtgg ccctgcacc agcagctcct      240 acaccggcgg ccctgcacc agcccctcc tggccctgt catcttctgt cccttcccag       300
aaaacctacc agggcagcta cggtttccgt ctgggcttct gcattctgg gacagccaag     360 tctgtgactt gcacgtactc ccctgccctc aacaagatgt tttgccaact ggccaagacc    420
tgccctgtgc agctgtgggt tgattccaca ccccgcccg gcacccgcgt ccgcgccatg     480
gccatctaca agcagtcaca gcacatgacg gaggttgtga ggcgctgccc ccaccatgag    540
cgctgctcag atagcgatgg tctggcccct cctcagcatc ttatccgagt ggaaggaaat    600
ttgcgtgtgg agtatttgga tgacagaaac acttttcgac atagtgtggt ggtgccctat    660
gagccgcctg aggttggctc tgactgtacc accatccact acaactacat gtgtaacagt    720
tcctgcatgg gcggcatgaa ccggaggccc atcctcacca tcatcacact ggaagactcc    780
agtggtaatc tactgggacg gaacagcttt gaggtgcgtg tttgtgcctg tcctgggaga    840
```

```
gaccggcgca cagaggaaga gaatctccgc aagaaagggg agctcaccac gagctgcccc      900
cagggagcac taagcgagca ctgcccaaca acaccagctc ctctcccag ccaaagaaga       960 aaccactgga tggagaatat ttcacccttc agatccgtgg gcgtgagcgc ttcgagatgt     1020
tccgagagct gaatgaggcc ttggaactca aggatgccca ggctgggaag gagccagggg    1080
ggagcagggc tcactccagc cacctgaagt ccaaaaggg tcagtctacc tcccgccata     1140
aaaaactcat gttcaagaca gaagggcctg actcagactg a                        1181
```

<210> SEQ ID NO 2
<211> LENGTH: 1781
<212> TYPE: DNA
<213> ORGANISM: mus musculus
<220> FEATURE:
<221> NAME/KEY: misc_feature
<223> OTHER INFORMATION: MURINE P53 NM_011640

<400> SEQUENCE: 2

```
tttcccctcc cacgtgctca ccctggctaa agttctgtag cttcagttca ttgggaccat       60
cctggctgta ggtagcgact acagttaggg ggcacctagc attcaggccc tcatcctcct      120
ccttcccagc agggtgtcac gcttctccga agactggatg actgccatgg aggagtcaca      180
gtcggatatc agcctcgagc tccctctgag ccaggagaca ttttcaggct tatggaaact      240
acttcctcca gaagatatcc tgccatcacc tcactgcatg gacgatctgt tgctgcccca      300
ggatgttgag gagtttttg aaggcccaag tgaagccctc cgagtgtcag gagctcctgc       360
agcacaggac cctgtcaccg agaccctgg gccagtggcc cctgccccag ccactccatg       420
gcccctgtca tcttttgtcc cttctcaaaa aacttaccag ggcaactatg cttccacct      480 gggcttcctg cagtctggga cagccaagtc tgttatgtgc acgtactctc ctcccctcaa      540
taagctattc tgccagctgg cgaagacgtg ccctgtgcag ttgtgggtca cgccacacc       600 tccagctggg agccgtgtcc gcgccatggc catctacaag aagtcacagc acatgacgga     660
ggtcgtgaga cgctgccccc accatgagcg ctgctccgat ggtgatggcc tggctcctcc      720
ccagcatctt atccgggtgg aaggaaattt gtatcccgag tatctggaag acaggcagac     780
ttttcgccac agcgtggtgg taccttatga gccacccgag gccggctctg agtataccac      840
catccactac aagtacatgt gtaatagctc ctgcatgggg ggcatgaacc gccgacctat      900
ccttaccatc atcacactgg aagactccag tgggaacctt ctgggacggg acagctttga    960
ggttcgtgtt tgtgcctgcc ctgggagaga ccgccgtaca gaagaagaaa atttccgcaa    1020
aaaggaagtc ctttgccctg aactgccccc agggagcgca agagagcgc tgcccacctg     1080 cacaagcgcc tctcccccgc aaaagaaaaa accacttgat ggagagtatt tcaccctcaa    1140
gatccgcggg cgtaaacgct tcgagatgtt ccgggagctg aatgaggcct tagagttaaa    1200
ggatgcccat gctacagagg agtctggaga cagcagggct cactccagct acctgaagac    1260
caagaagggc cagtctactt cccgccataa aaaacaatg gtcaagaaag tggggcctga    1320
ctcagactga ctgcctctgc atcccgtccc catcaccagc ctccctctct ccttgctgtc    1380
ttatgacttc agggctgaga cacaatcctc ccggtccctt ctgctgcctt tttaccttg     1440 tagctagggc tcagccccct ctctgagtag tggttcctgg cccaagttgg ggaataggtt    1500
gatagttgtc aggtctctgc tgggccagcg aaattctatc cagccagttg ttggaccctg    1560
gcacctacaa tgaaatctca ccctacccca caccctgtaa gattctatct tgggccctca    1620
tagggtccat atcctccagg gcctactttc cttccattct gcaaagcctg tctgcattta    1680
```

```
tccaccccccc accctgtctc cctcttttt ttttttttac cccttttat atatcaattt    1740 cctatttttac aataaaattt tgttatcact taaaaaaaaa a                      1781

<210> SEQ ID NO 3
<211> LENGTH: 783
<212> TYPE: DNA
<213> ORGANISM: homo sapiens
<220> FEATURE:
<221> NAME/KEY: misc_feature
<223> OTHER INFORMATION: DNA P53 Delta 133

<400> SEQUENCE: 3
atgttttgcc aactggccaa gacctgccct gtgcagctgt gggttgattc cacaccccg      60 cccggcaccc gcgtccgcgc catggccatc tacaagcagt cacagcacat gacggaggtt   120
gtgaggcgct gcccccacca tgagcgctgc tcagatagcg atggtctggc ccctcctcag   180
catcttatcc gagtggaagg aaatttgcgt gtggagtatt tggatgacag aaacactttt   240
cgacatagtg tggtggtgcc ctatgagccg cctgaggttg gctctgactg taccaccatc   300
cactacaact acatgtgtaa cagttcctgc atgggcggca tgaaccggag gcccatcctc   360
accatcatca cactggaaga ctccagtggt aatctactgg gacggaacag ctttgaggtg   420
cgtgtttgtg cctgtcctgg gagagaccgg cgcacagagg aagagaatct ccgcaagaaa   480
ggggagcctc accacgagct gcccccaggg agcactaagc gagcactgcc caacaacacc   540
agctcctctc cccagccaaa gaagaaacca ctggatggag aatatttcac ccttcagatc   600
cgtgggcgtg agcgcttcga gatgttccga gagctgaatg aggccttgga actcaaggat   660
gcccaggctg gaaggagcc aggggggagc agggctcact ccagccacct gaagtccaaa   720
aagggtcagt ctacctcccg ccataaaaaa ctcatgttca agacagaagg gcctgactca   780
gac                                                                 783

<210> SEQ ID NO 4
<211> LENGTH: 1023
<212> TYPE: DNA
<213> ORGANISM: homo sapiens
<220> FEATURE:
<221> NAME/KEY: misc_feature
<223> OTHER INFORMATION: DNA P53 BETA

<400> SEQUENCE: 4
atggaggagc cgcagtcaga tcctagcgtc gagccccctc tgagtcagga aacattttca    60
gacctatgga aactacttcc tgaaaacaac gttctgtccc ccttgccgtc caagcaatg   120 gatgatttga tgctgtcccc ggacgatatt gaacaatggt tcactgaaga cccaggtcca   180
gatgaagctc ccagaatgcc agaggctgct ccccgcgtgg ccctgcacc agcagctcct   240 acaccggcgg cccctgcacc agccccctcc tggcccctgt catcttctgt cccttcccag   300
aaaacctacc agggcagcta cggtttccgt ctgggcttct tgcattctgg gacagccaag   360
tctgtgactt gcacgtactc ccctgccctc aacaagatgt ttgccaact ggccaagacc   420 tgccctgtgc agctgtgggt tgattccaca ccccgcccg caccgcgt ccgcgccatg   480 gccatctaca agcagtcaca gcacatgacg gaggttgtga ggcgctgccc caccatgag   540 cgctgctcag atagcgatgg tctggcccct cctcagcacc ttatccgagt ggaaggaaat   600
ttgcgtgtgg agtatttgga tgacagaaac acttttcgac atagtgtggt ggtgccctat   660
gagccgcctg aggttggctc tgactgtacc accatccact acaactacat gtgtaacagt   720
```

| | |
|---|---|
| tcctgcatgg gcggcatgaa ccggaggccc atcctcacca tcatcacact ggaagactcc | 780 |
| agtggtaatc tactgggacg gaacagcttt gaggtgcgtg tttgtgcctg tcctgggaga | 840 |
| gaccggcgca cagaggaaga gaatctccgc aagaaagggg agcctcacca cgagctgccc | 900 |
| ccagggagca ctaagcgagc actgcccaac aacaccagct cctctcccca gccaaagaag | 960 |
| aaaccactgg atggagaata tttcaccctt caggaccaga ccagctttca aaagaaaat | 1020 |
| tgt | 1023 |

```
<210> SEQ ID NO 5
<211> LENGTH: 1038
<212> TYPE: DNA
<213> ORGANISM: homo sapiens
<220> FEATURE:
<221> NAME/KEY: misc_feature
<223> OTHER INFORMATION: DNA P53 GAMA

<400> SEQUENCE: 5
```

| | |
|---|---|
| atggaggagc cgcagtcaga tcctagcgtc gagcccctc tgagtcagga aacattttca | 60 |
| gacctatgga aactacttcc tgaaaacaac gttctgtccc ccttgccgtc ccaagcaatg | 120 |
| gatgatttga tgctgtcccc ggacgatatt gaacaatggt tcactgaaga cccaggtcca | 180 |
| gatgaagctc ccagaatgcc agaggctgct ccccccgtgg cccctgcacc agcagctcct | 240 |
| acaccggcgg cccctgcacc agccccctcc tggcccctgt catcttctgt cccttcccag | 300 |
| aaaacctacc agggcagcta cggtttccgt ctgggcttct tgcattctgg gacagccaag | 360 |
| tctgtgactt gcacgtactc ccctgccctc aacaagatgt tttgccaact ggccaagacc | 420 |
| tgccctgtgc agctgtgggt tgattccaca ccccccgccg gcacccgcgt ccgcgccatg | 480 |
| gccatctaca gcagtcaca gcacatgacg gaggttgtga ggcgctgccc ccaccatgag | 540 |
| cgctgctcag atagcgatgg tctggcccct cctcagcatc ttatccgagt ggaaggaaat | 600 |
| ttgcgtgtgg agtatttgga tgacagaaac acttttcgac atagtgtggt ggtgccctat | 660 |
| gagccgcctg aggttggctc tgactgtacc accatccact acaactacat gtgtaacagt | 720 |
| tcctgcatgg gcggcatgaa ccggaggccc atcctcacca tcatcacact ggaagactcc | 780 |
| agtggtaatc tactgggacg gaacagcttt gaggtgcgtg tttgtgcctg tcctgggaga | 840 |
| gaccggcgca cagaggaaga gaatctccgc aagaaagggg agcctcacca cgagctgccc | 900 |
| ccagggagca ctaagcgagc actgcccaac aacaccagct cctctcccca gccaaagaag | 960 |
| aaaccactgg atggagaata tttcaccctt cagatgctac ttgacttacg atggtgttac | 1020 |
| ttcctgataa actcgtcg | 1038 |

```
<210> SEQ ID NO 6
<211> LENGTH: 1062
<212> TYPE: DNA
<213> ORGANISM: homo sapiens
<220> FEATURE:
<221> NAME/KEY: misc_feature
<223> OTHER INFORMATION: DNA P53 Delta 40

<400> SEQUENCE: 6
```

| | |
|---|---|
| atggatgatt tgatgctgtc cccggacgat attgaacaat ggttcactga agacccaggt | 60 |
| ccagatgaag ctcccagaat gccagaggct gctccccccg tggcccctgc accagcagct | 120 |
| cctacaccgg cggcccctgc accagccccc tcctggcccc tgtcatcttc tgtcccttcc | 180 |
| cagaaaacct accagggcag ctacggtttc cgtctgggct tcttgcattc tgggacagcc | 240 |
| aagtctgtga cttgcacgta ctcccctgcc ctcaacaaga tgttttgcca actggccaag | 300 |

```
acctgccctg tgcagctgtg ggttgattcc acacccccgc ccggcacccg cgtccgcgcc      360
atggccatct acaagcagtc acagcacatg acggaggttg tgaggcgctg cccccaccat      420
gagcgctgct cagatagcga tggtctggcc cctcctcagc atcttatccg agtggaagga      480
aatttgcgtg tggagtattt ggatgacaga aacactttc gacatagtgt ggtggtgccc       540
tatgagccgc tgaggttgg ctctgactgt accaccatcc actacaacta catgtgtaac       600
agttcctgca tgggcggcat gaaccggagg cccatcctca ccatcatcac actgaagac       660 tccagtggta atctactggg acggaacagc tttgaggtgc gtgtttgtgc ctgtcctggg      720
agagaccggc gcacagagga agagaatctc cgcaagaaag gggagcctca ccacgagctg      780
cccccaggga gcactaagcg agcactgccc aacaacacca gctcctctcc ccagccaaag      840
aagaaaccac tggatggaga atatttcacc cttcagatcc gtgggcgtga gcgcttcgag      900
atgttccgag agctgaatga ggccttggaa ctcaaggatg cccaggctgg aaggagcca       960 gggggagca gggctcactc cagccacctg aagtccaaaa agggtcagtc tacctcccgc      1020 cataaaaac tcatgttcaa gacagaaggg cctgactcag ac                         1062

<210> SEQ ID NO 7
<211> LENGTH: 345
<212> TYPE: DNA
<213> ORGANISM: homo sapiens
<220> FEATURE:
<221> NAME/KEY: misc_feature
<223> OTHER INFORMATION: DNA P2RY2 variant 1

<400> SEQUENCE: 7
atgcgtccac cacatatatg ttccacctgg ctgtgtctga tgcactgtat gcggcctccc       60
tgccgctgct ggtctattac tacgcccgcg gcgaccactg gccttcagc acggtgctct      120 gcaagctggt gcgcttcctc ttctacacca acctttactg cagcatcctc ttcctcacct      180
gcatcagcgt gcaccggtgt ctgggcgtct tacgacctct cgctccctg cgctggggcc      240 gggcccgcta cgctcgccgg gtggccgggg ccgtgtgggt gttggtgctg gcctgccagg      300
cccccgtgct ctactttgtc accaccagcg cgcgcggggg ccgcg                     345

<210> SEQ ID NO 8
<211> LENGTH: 2547
<212> TYPE: DNA
<213> ORGANISM: homo sapiens
<220> FEATURE:
<221> NAME/KEY: misc_feature
<223> OTHER INFORMATION: DNA P2RY2 variant 2

<400> SEQUENCE: 8
gaacagcgca gggaggtggg tagccgggct cccaggcacg tgggtctctg cggctgcggc       60
gggacccggg cactggcacc cgggagcggc ggcgacggca ccctgagagg agaagcgcag      120
cgcagtggcg agaggagccc cttgtggcag cagcactacc tgcccagaaa atgctggag      180 gctgggcgtg gccccaggcc tggggacctg tttttcctgt ttcccgcaga gttccctgca      240
gcccggtcca gtccaggcg tgtgcattca tgagtgagga acccgtgcag gcgctgagca      300
tcctgacctg gagagcaggg gctggtcagg gcgatggcag cagacctggg ccctggaat      360 gacaccatca atggcacctg ggatgggat gagctggct acaggtgccg cttcaacgag       420
gacttcaagt acgtgctgct gcctgtgtcc tacggcgtgg tgtgcgtgcc tgggctgtgt      480
ctgaacgccg tggcgctcta catcttcttg tgccgcctca agacctggaa tgcgtccacc       540
```

```
acatatatgt tccacctggc tgtgtctgat gcactgtatg cggcctccct gccgctgctg    600
gtctattact acgcccgcgg cgaccactgg cccttcagca cggtgctctg caagctggtg    660
cgcttcctct tctacaccaa ccttactgc agcatcctct tcctcacctg catcagcgtg     720
caccggtgtc tgggcgtctt acgacctctg cgctccctgc gctggggccg ggcccgctac    780
gctcgccggg tggccggggc cgtgtgggtg ttggtgctgg cctgccaggc ccccgtgctc    840
tactttgtca ccaccagcgc gcgcgggggc cgcgtaacct gccacgacac ctcggcaccc    900
gagctcttca gccgcttcgt ggcctacagc tcagtcatgc tgggcctgct cttcgcggtg    960
cccttttgccg tcatccttgt ctgttacgtg ctcatggctc ggcgactgct aaagccagcc   1020
tacgggacct cgggcggcct gcctagggcc aagcgcaagt ccgtgcgcac catcgccgtg   1080
gtgctggctg tcttcgccct ctgcttcctg ccattccacg tcacccgcac cctctactac   1140
tccttccgct cgctggacct cagctgccac accctcaacg ccatcaacat ggcctacaag   1200
gttacccggc cgctggccag tgctaacagt tgccttgacc ccgtgctcta cttcctggct   1260
gggcagaggc tcgtacgctt tgcccgagat gccaagccac ccactggccc cagccctgcc   1320
accccggctc gccgcaggct gggcctgcgc agatccgaca gaactgacat gcagaggata   1380
gaagatgtgt tgggcagcag tgaggactct aggcggacag agtccacgcc ggctggtagc   1440
gagaacacta aggacattcg gctgtaggag cagaacactt cagcctgtgc aggtttatat   1500
tgggaagctg tagaggacca ggacttgtgc agacgccaca gtctccccag atatggacca   1560
tcagtgactc atgctggatg accccatgct ccgtcatttg acaggggctc aggatattca   1620
ctctgtggtc cagagtcaac tgttcccata acccctagtc atcgtttgtg tgtataagtt   1680
ggggggaatta agtttcaaga aaggcaagag ctcaaggtca atgacacccc tggcctgact   1740
cccatgcaag tagctggctg tactgccaag gtacctaggt tggagtccag cctaatcaag   1800
tcaaatggag aaacaggccc agagaggaag gtggcttacc aagatcacat accagagtct   1860
ggagctgagc tacctggggt gggggccaag tcacaggttg ccagaaaaac cctggtaagt   1920
aatgagggct gagtttgcac agtggtctgg aatggactgg gtgccacggt ggacttagct   1980
ctgaggagta cccccagccc aagagatgaa catctgggga ctaatatcat agacccatct   2040
ggaggctccc atgggctagg agccagtgtg aggctgtaac ttatactaaa ggttgtgttg   2100
cctgctgagc tgtgccctat tgtgtggtcg gggatgagg atatggcagg aagctttca    2160
ccagccacac aagggtcctt tctccaatcc gttcccttct gccacctgcc ttctcactag   2220
ctgtctcagg agtagtctca tatcagggat ccctctctcca ggcccaggt catccccac    2280
tgtaaagcca gttggcttct gtgcctgact ctgtgctgag cacagagaaa agtcaggtgc   2340
agtcccagtc cttgagattt cccagtttag gtgatggcca gtcatgtgct ggtaaatgtt   2400
aagccattta actggagctc cgatttaact gggaaccct tctttgtaga actgcccatt    2460
tccatggtgc aaaactctt atggccaaat tcaaactata aacatgatgt caacttcctt    2520
gtaaaaaaaa aaaaaaaaa aaaaaaa                                         2547
```

<210> SEQ ID NO 9
<211> LENGTH: 8667
<212> TYPE: DNA
<213> ORGANISM: homo sapiens
<220> FEATURE:
<221> NAME/KEY: misc_feature
<223> OTHER INFORMATION: DNA P2Y2 variant 3

<400> SEQUENCE: 9

```
caaggcgctg ggagaggccc ggggaagcgg cgggccagac tggcgcaggt gcggactggg      60
cgcggggcag gggagggcgc tgtggagcgg ctgtcgcccc ggggcacagt tgcgagccgg     120
cgtgtagcgc ataactggac ggcttgaacg cgcctgtggg tccgtggttg aactttgtct     180
ccacgggagc gtcggtctcg gagcccttg tggcagcagc actacctgcc cagaaaatg      240 ctggaggctg ggcgtggccc caggcctggg gacctgtttt tcctgtttcc cgcagagttc     300
cctgcagccc ggtccaggtc caggcgtgtg cattcatgag tgaggaaccc gtgcaggcgc     360
tgagcatcct gacctggaga gcaggggctg gtcagggcga tggcagcaga cctgggcccc     420
tggaatgaca ccatcaatgg cacctgggat ggggatgagc tgggctacag gtgccgcttc     480
aacgaggact tcaagtacgt gctgctgcct gtgtcctacg gcgtggtgtg cgtgcttggg     540
ctgtgtctga cgccgtggc gctctacatc ttcttgtgcc gcctcaagac ctggaatgcg     600
tccaccacat atatgttcca cctggctgtg tctgatgcac tgtatgcggc ctccctgccg     660
ctgctggtct attactacgc ccgcggcgac cactggccct tcagcacggt gctctgcaag     720
ctggtgcgct tcctcttcta caccaacctt tactgcagca cctcttcct cacctgcatc      780 agcgtgcacc ggtgtctggg cgtcttacga cctctgcgct ccctgcgctg gggccgggcc     840
cgctacgctc gccgggtggc cggggccgtg tgggtgttgg tgctggcctg ccaggccccc     900
gtgctctact ttgtcaccac cagcgcgcgc ggggccgcg taacctgcca cgacacctcg      960
gcacccgagc tcttcagccg cttcgtggcc tacagctcag tcatgctggg cctgctcttc    1020
gcggtgccct ttgccgtcat ccttgtctgt tacgtgctca tggctcggcg actgctaaag    1080
ccagcctacg ggacctcggg cggcctgcct agggccaagc gcaagtccgt gcgcaccatc    1140
gccgtggtgc tggctgtctt cgccctctgc ttcctgccat tccacgtcac ccgcacccte    1200 tactactcct tccgctcgct ggacctcagc tgccacaccc tcaacgccat caacatggcc    1260
tacaaggtta cccggccgct ggccagtgct aacagttgcc ttgaccccgt gctctacttc    1320
ctggctgggg agaggctcgt acgctttgcc cgagatgcca agccaccac tggccccagc     1380 cctgccaccc cggctcgccg caggctgggc ctgcgcagat ccgacagaac tgacatgcag    1440
aggatagaag atgtgttggg cagcagtgag gactctaggc ggacagagtc cacgccggct    1500
ggtagcgaga acactaagga cattcggctg taggagcaga acacttcagc ctgtgcaggt    1560
ttatattggg aagctgtaga ggaccaggac ttgtgcagac gccacagtct ccccagatat    1620
ggaccatcag tgactcatgc tggatgaccc catgctccgt catttgacag gggctcagga    1680
tattcactct gtggtccaga gtcaactgtt cccataaccc ctagtcatcg tttgtgtgta    1740
taagttgggg gaattaagtt tcaagaaagg caagagctca aggtcaatga caccctggc     1800 ctgactccca tgcaagtagc tggctgtact gccaaggtac ctaggttgga gtccagccta    1860
atcaagtcaa atggagaaac aggcccagag aggaaggtgg cttaccaaga tcacatacca    1920
gagtctggag ctgagctacc tggggtgggg gccaagtcac aggttggcca gaaaaccctg    1980
gtaagtaatg agggctgagt ttgcacagtg gtctggaatg gactgggtgc cacggtggac    2040
ttagctctga ggagtacccc cagcccaaga gatgaacatc tggggactaa tatcatagac    2100
ccatctggag gctcccatgg gctaggagcc agtgtgaggc tgtaacttat actaaaggtt    2160
gtgttgcctg ctgagctgtg ccctattgtg tggtcggggg atgaggatat ggcagggaag    2220 cttttcaccag ccacacaagg gtcctttctc caatccgttc ccttctgcca cctgccttct   2280
cactagctgt ctcaggagta gtctcatatc agggatcctc tctccaggcc ccaggtcatc    2340
ccccactgta aagccagttg gcttctgtgc ctgactctgt gctgagcaca gagaaaagtc    2400
```

-continued

```
aggtgcagtc ccagtccttg agatttccca gtttaggtga tggccagtca tgtgctggta    2460
aatgttaagc catttaactg gagctccgat ttaactggga acccottott tgtagaactg    2520 cccatttcca tggtgcaaaa actcttatgg ccaaattcaa actataaaca tgatgtcaac    2580
ttccttgtaa aattcctgaa aatttaacaa ttggttcttg caagcaggta caagtcactc    2640
tagcacacca ctggataatg ccgagtggct ggggctgtga gccagggggt cagggaaggg    2700
ttcctggagt gggagactcc tgagctgtag cttctgagaa aagcagctca ccggaagaac    2760
atccacacac aggatgcatc ccaggcaaag acatgggca agagggcagg gtgtgcatga     2820
gccataagca ggctggacag ctgactccag gctcaaggca gggttggggc tgggtcacaa    2880
ggaggccaag ttagggctcc ctccttgccc tgaccctgag gcttcctttg cactgggggt    2940
aaatatgaaa gagattcact cctcctcctg tccatcgtct gccttctggg aaaatcccag    3000
aatggcaggg tggtgctcag gctgggtcag gacttagtat gggggagatg ggtctcacct    3060
atgataggtt ctgagtctag ccaggaccac tctgggctga cgtgtggcgc tcagctggac    3120
agggccccgc cctagccttt ggaaagggac agggcaaagc tgacaggcct cactcttgat    3180
ctcaaggaca gggactccct cctctccctc tgggagagcc ctcgccctgt ggcccactct    3240
gcctgccccc tctgacctct ccacccttcc cactctgcct tgtgaaaggc aggacatccc    3300
caaagcttgc tgtatttgga gcctgactcc acagcgccct catgtgacag agacccatca    3360
cagaccatga cccaaatgat tactctgtac tgtgccaggt gggtgacctg cccagaatag    3420
tgtgagctat tcacctctca ccttctaggt tctatacttc tgttaatgta gccgatgtcc    3480
ttctgagttt ttttttttctt tttgagacga agtcttgttc tgtcacccag gctggaagtg    3540
cagtgctgcg gtcttggctc actgcaactc tctgcctccc gggttcaagc aattctcctg    3600
cctcagtttc ccaagtagct gggattacag gtatgcgcca ccacacctgg ctaattttg    3660 tatttttaat agagacaggg tttcgccatg ttggccaggc tggtctcaaa ctcctgacct    3720
caagtgatcc acctgcctca gcctcccaaa gtgctgggat tacaggtatg agccaccgca    3780
cccggcccct cttgagcttt cttaatgatt gcctgttaca aaccacccct gagccttttcc    3840 cacaggcccg agccactcca caaggacaca ggagggctc gttcaccatc taatcctgtg    3900
gcaggcacag gtgggggtgg atactggaga ccctgggtga accaggggca cctctggaac    3960
ccagttggac tgcctggccc cttggtatgc acgtcccacc ttgctgctca gtgcccaggc    4020
cacttgcctt gtgggtgaag ttcctgccct gatgcctcat gctatttta gcccaagtaa    4080 gaccataatt ttccactcct ggccccagac cattgtccag cagtgacgtg aggggatctg    4140
cctgccctca aaatatctcc tattaccctc caatattccc tgcccccttc acacctccct    4200
aacctgacat cacttcctgg gctgttgact catgaaggcc actgtgaaag gcacgtgag    4260 ttgcccatcc actgagcaga cccagggat tatccagccc agctgcagac tcaaggccag    4320
agatgggcag ggctgagccc aaggtcattc agcaggtcag cgtggcgcct ggatgtaagc    4380
aagtgccttg gtgacgatcc tgctgtcact cacactgccc agctcttcct gcccagggtg    4440
actgggatgg agccatagac ctgaggccag ggacaggaca gggatgggag gaaagggagg    4500
gtagagagtt gagtgtcagg gagtaaatgt ctgctgatgt gcctgcagca gctgttctca    4560
atgaactgca tgacatcagg gcagggtccc tggcacacag gggtctctgc cctgggtggc    4620
aggtgtccca gggtccagga gggatggagg aaccccaggg tacattccca cttt caccccc    4680 ctgaggttag aagaggccct aagcaacatg ttatccacac atggttgctc caggtcaagt    4740
```

```
caccaaagct acctctctgt caccccttgtc atggcagatt tgggctgctc tgtttagaat    4800
caggcacatg agggagggaa gtcgtgtatt gacccatgtc ccacgcaccc tctcatctat    4860
gttatatggt ggatgcttca cagaagccct gggaagtaga tgctatgatc ctatttagca    4920
gatgaggaaa caggagaagg gcgtgagaag tgaggacttg ttccaggtta tccaggctgt    4980
cagggtgagt cagagtgagt ccaggttcac ctgatggcca gaatcatgcc ctttatagtg    5040
ccccacgaca ctcacagccc tgcagggcag aagggtctat aagtggcccc tcgcatgatt    5100
caagatgaca gaggcagtgt agcaaggatg tgagaacaca gatgctccac ccagaccacc    5160
tcagtgtcaa tattgtcccc actttcctgg ctggggtctc ttgggcaagt tacctaatct    5220
tgcagcacct cagttttccc atttctaaag tgtgctgcta ccttccatgc agggcgttga    5280
ggggcttccc tacgttatta cgcacaaagt cctcctcaca gtgcctggtg tgtggtcagc    5340
atttatatgc ctggcaccag gccgggggct atggaggcaa atcagctggg ccctgccctc    5400
acagagttga catcacttag tacgtaacca cattgggata catgttttga aggagaggac    5460
agtgtgtctg gccagtgagc aacagtgggc catacgtctc cagggaaccc ccgtgggggtg    5520
tgggaggagg gaagcaggtc tgtcctgggg gaatgtgtgg gaccacctct gccctgcttg    5580
gcagtaggtg gatttcagga ccatgggcct gtgctgttta cagaaccttg tccaggtgcc    5640
cagctgtggg agggcagcat ggagaggagg aagaggggggc cctagtagc aagcttcaga    5700
aacttgccac ttcaggctag agagctcgca ccctcccacg gcagcagggt agccatttct    5760
ccctgactgg ggtgtccacc atggtgctct gcagccacct ctcacttcat taagagtcca    5820
cagatctagg agcagaggac tggtctggag ctgggcaagg gcaggcagca atgggggagt    5880
ttttgctgtg tgacctgagg tcacttgcct gccttctctg gactgcactg tagggcctgg    5940
agacctgttc ccctgttcca atttccccac ctcagtgaag gcacaaccaa cagctgctcc    6000
ccgggcattt ccaagaccct ccaggccccc agctctgagg actagggtgg aggcagtgtt    6060
tctccccagc atcaagtgac cagagaagtg aagtgacccc actgccgcca cacagagcca    6120
cacagtgcga tgtctggagc tcctgcctcc tgcaaggtgg agggtggggc ttggccagga    6180
gtgaccagac tacagagtga ggggtgtgct tgtgggggtg aagggttggg gtgagaactg    6240
agcccgagtc gaactcatcc tcctctgccc tgatgcactg tgcaacttgg gggagtcact    6300
gtccctctct gggcctcgct ttccccatct tcgataggac ttggctctgc ctggccactc    6360
ctcctccaat gggggaattc ctgggcttgc ctctgtcttg gctccagctc aggtgtcagt    6420
ctcagccctg tccagccagg aacaatgggc caggcaggg ccagtcaccc cctgtccctg    6480
ggggctccac ccacggccct ggactatttt cagcccttgc agatggagtc agaagaggat    6540
tttccactcc cagtacaatg actgccctgg accattgtcc agcagtgacg cgggggacct    6600
gcctgcccca aaatatctcc tgcccctagt ttccaagcct ctttgccctg ctcctcacct    6660
cctggccctg ctccttacct ccccaccctg atgtcatttc ctggggctct taactcctga    6720
aggccattgt gaaacatcac gtgagactcc tgggagacac aaccagttgg aatgagtttt    6780
ccctcctggc agggacccca gggattgttt ggctgcttag tgggactggt ggcccagaga    6840
gggctgtgcc ttacccagtc acacagcagt cagtgtgaag cttaggtgta agcccagggc    6900
tctttggctg ctcccactgc ctcagccaac ttcattagct ccagtctgtg gctcctggac    6960
tggagctaca gtggtgagag ctcaccactg agcttcctgg gatgggcacc tgggatagca    7020
gcccaagtgg tgtgggtgga gaggtgcagc tcatgctctg accttggagt gagcccagtg    7080
caggggcctg accttaaacc ctttctcccc actgagtccc attttttacca aatgtggctg    7140
```

```
ttaggaactg aatgtttgtg tcccccgccc cacaaatcca tatgtcaaaa tcccaactgc    7200
caaggtgatg gtattagaag gtggggcctt tgggaagtaa ccaggtccta agggtgcagc    7260
cctcatgaat gggtttagtg cccttacaga atggacccca gagagctcct caccctcttt    7320
ccaccatgtg aggatataat gagaagttgg cagtctgcaa cctggaagag gtccctcacc    7380
agatcccaac catgctggca ccccgatctt agacttccag tcttcagaat ggtgagaaat    7440
aaatgtctct tgtttctaat ccacccagtc ggtggcattt tgttatagca gcccacgctg    7500
actgtgactg aactcagggt gacagagcag cagctctggg gcaaggggga gggtgggggc    7560
cacagggcag ctgatgcagg agcagggctc tggcacagtt cagccatcac caattctggg    7620
actgcaaatt cagtttcttc atctggaaaa ttgaactggt aataccaata cctcttttcc    7680
cggtttacta gacagagaca atgcagtgag gcacaaacat gcaactgttt gattttcctc    7740
ccacccatgc tccctgctca gtgacgtgtg attttccttt cccatccata aactgcgcat    7800
ttggcaaact ccaaactttt gagtcacttt tgggtaacaa agtcaggttt aagatttcca    7860
tcgcctgctt aattgaatgc tcacctgtcc tcttccccca tgctgtgagg accttcatca    7920
ctcctcttct gggtccctct ctcctctagg tgttggggca gggtggggag gaaagggacc    7980
aatgtgtctt tcctggtgat gctacagccc tctcttgctg accttgcttc ctgggccatc    8040
agtgcccccct gcacagaact ctccaaacat cagtccacac ctttgtaaaa acagtctctc    8100
cgctaagcta tcccaaaatg acctgattag agtgtgcaac gtctttcctg ctgggactct    8160
gactgatacc ctggtctccc tgagtgattt tcctgcacac cctgctgggg atgtggaagc    8220
ctgtccccct cccaccccac accccacact tggctgagat ctcacagtgg caaagatgtc    8280
tttgaatcca tggtgcccag ggttcagcgt gtagagtgag gtggggtgtg tagagagctg    8340
gggcaaggaa ccctgagaag atgtcttacc ccagttgttt ccaggtttct ttagaaagcg    8400
ggctatttta ccccatgtgt cctcagattt atgtcctgga accaaattcc aaatcagcag    8460
ccacatgaaa agtcccctcc tctctggcgt ggaattaaac tgttagacct gcctttgtga    8520
ccaaagcaat tgtaaaacgt gggggaggaa attaaaagcc tgccaccta gtccacacag    8580
tgtgtgctgt ctctgtgtgt gtgcacgtgt gtttatgtgt gtgttgaatg atcacatgtt    8640
ccagggagga tggtgagggg cgagggg                                        8667
```

<210> SEQ ID NO 10
<211> LENGTH: 115
<212> TYPE: PRT
<213> ORGANISM: homo sapiens
<220> FEATURE:
<221> NAME/KEY: MISC_FEATURE
<223> OTHER INFORMATION: amino acid sequence of P2Y2R

<400> SEQUENCE: 10

```
Met Arg Pro Pro His Ile Cys Ser Thr Trp Leu Cys Leu Met His Cys
1               5                   10                  15

Met Arg Pro Pro Cys Arg Cys Trp Ser Ile Thr Thr Pro Ala Ala Thr
            20                  25                  30

Thr Gly Pro Ser Ala Arg Cys Ser Ala Ser Trp Cys Ala Ser Ser Ser
        35                  40                  45

Thr Pro Thr Phe Thr Ala Ala Ser Ser Ser Pro Ala Ser Ala Cys
    50                  55                  60

Thr Gly Val Trp Ala Ser Tyr Asp Leu Cys Ala Pro Cys Ala Gly Ala
65                  70                  75                  80
```

```
Gly Pro Ala Thr Leu Ala Gly Trp Pro Pro Cys Gly Cys Trp Cys
                85                  90                  95

Trp Pro Ala Arg Pro Pro Cys Ser Thr Leu Ser Pro Ala Arg Ala
            100                 105                 110

Gly Ala Ala
        115

<210> SEQ ID NO 11
<211> LENGTH: 393
<212> TYPE: PRT
<213> ORGANISM: homo sapiens
<220> FEATURE:
<221> NAME/KEY: MISC_FEATURE
<223> OTHER INFORMATION: amino acid sequence of p53 human

<400> SEQUENCE: 11

Met Glu Glu Pro Gln Ser Asp Pro Ser Val Glu Pro Pro Leu Ser Gln
1               5                   10                  15

Glu Thr Phe Ser Asp Leu Trp Lys Leu Leu Pro Glu Asn Asn Val Leu
            20                  25                  30

Ser Pro Leu Pro Ser Gln Ala Met Asp Asp Leu Met Leu Ser Pro Asp
        35                  40                  45

Asp Ile Glu Gln Trp Phe Thr Glu Asp Pro Gly Pro Asp Glu Ala Pro
    50                  55                  60

Arg Met Pro Glu Ala Ala Pro Pro Val Ala Pro Ala Pro Ala Ala Pro
65                  70                  75                  80

Thr Pro Ala Ala Pro Ala Pro Ala Pro Ser Trp Pro Leu Ser Ser Ser
                85                  90                  95

Val Pro Ser Gln Lys Thr Tyr Gln Gly Ser Tyr Gly Phe Arg Leu Gly
            100                 105                 110

Phe Leu His Ser Gly Thr Ala Lys Ser Val Thr Cys Thr Tyr Ser Pro
        115                 120                 125

Ala Leu Asn Lys Met Phe Cys Gln Leu Ala Lys Thr Cys Pro Val Gln
    130                 135                 140

Leu Trp Val Asp Ser Thr Pro Pro Gly Thr Arg Val Arg Ala Met
145                 150                 155                 160

Ala Ile Tyr Lys Gln Ser Gln His Met Thr Glu Val Val Arg Cys
                165                 170                 175

Pro His His Glu Arg Cys Ser Asp Ser Asp Gly Leu Ala Pro Pro Gln
            180                 185                 190

His Leu Ile Arg Val Glu Gly Asn Leu Arg Val Glu Tyr Leu Asp Asp
        195                 200                 205

Arg Asn Thr Phe Arg His Ser Val Val Val Pro Tyr Glu Pro Pro Glu
    210                 215                 220

Val Gly Ser Asp Cys Thr Thr Ile His Tyr Asn Tyr Met Cys Asn Ser
225                 230                 235                 240

Ser Cys Met Gly Gly Met Asn Arg Arg Pro Ile Leu Thr Ile Ile Thr
                245                 250                 255

Leu Glu Asp Ser Ser Gly Asn Leu Leu Gly Arg Asn Ser Phe Glu Val
            260                 265                 270

Arg Val Cys Ala Cys Pro Gly Arg Asp Arg Arg Thr Glu Glu Glu Asn
        275                 280                 285

Leu Arg Lys Lys Gly Glu Pro His His Glu Leu Pro Pro Gly Ser Thr
    290                 295                 300

Lys Arg Ala Leu Pro Asn Asn Thr Ser Ser Ser Pro Gln Pro Lys Lys
305                 310                 315                 320
```

```
Lys Pro Leu Asp Gly Glu Tyr Phe Thr Leu Gln Ile Arg Gly Arg Glu
            325                 330                 335

Arg Phe Glu Met Phe Arg Glu Leu Asn Glu Ala Leu Glu Leu Lys Asp
        340                 345                 350

Ala Gln Ala Gly Lys Glu Pro Gly Gly Ser Arg Ala His Ser Ser His
        355                 360                 365

Leu Lys Ser Lys Lys Gly Gln Ser Thr Ser Arg His Lys Lys Leu Met
    370                 375                 380

Phe Lys Thr Glu Gly Pro Asp Ser Asp
385                 390

<210> SEQ ID NO 12
<211> LENGTH: 390
<212> TYPE: PRT
<213> ORGANISM: mus musculus
<220> FEATURE:
<221> NAME/KEY: MISC_FEATURE
<223> OTHER INFORMATION: amino acid sequence of p53 mouse

<400> SEQUENCE: 12

Met Thr Ala Met Glu Glu Ser Gln Ser Asp Ile Ser Leu Glu Leu Pro
1               5                   10                  15

Leu Ser Gln Glu Thr Phe Ser Gly Leu Trp Lys Leu Leu Pro Pro Glu
            20                  25                  30

Asp Ile Leu Pro Ser Pro His Cys Met Asp Asp Leu Leu Leu Pro Gln
        35                  40                  45

Asp Val Glu Glu Phe Phe Glu Gly Pro Ser Glu Ala Leu Arg Val Ser
    50                  55                  60

Gly Ala Pro Ala Ala Gln Asp Pro Val Thr Glu Thr Pro Gly Pro Val
65                  70                  75                  80

Ala Pro Ala Pro Ala Thr Pro Trp Pro Leu Ser Ser Phe Val Pro Ser
                85                  90                  95

Gln Lys Thr Tyr Gln Gly Asn Tyr Gly Phe His Leu Gly Phe Leu Gln
            100                 105                 110

Ser Gly Thr Ala Lys Ser Val Met Cys Thr Tyr Ser Pro Pro Leu Asn
        115                 120                 125

Lys Leu Phe Cys Gln Leu Ala Lys Thr Cys Pro Val Gln Leu Trp Val
    130                 135                 140

Ser Ala Thr Pro Pro Ala Gly Ser Arg Val Arg Ala Met Ala Ile Tyr
145                 150                 155                 160

Lys Lys Ser Gln His Met Thr Glu Val Val Arg Arg Cys Pro His His
                165                 170                 175

Glu Arg Cys Ser Asp Gly Asp Gly Leu Ala Pro Pro Gln His Leu Ile
            180                 185                 190

Arg Val Glu Gly Asn Leu Tyr Pro Glu Tyr Leu Glu Asp Arg Gln Thr
        195                 200                 205

Phe Arg His Ser Val Val Val Pro Tyr Glu Pro Pro Glu Ala Gly Ser
    210                 215                 220

Glu Tyr Thr Thr Ile His Tyr Lys Tyr Met Cys Asn Ser Ser Cys Met
225                 230                 235                 240

Gly Gly Met Asn Arg Arg Pro Ile Leu Thr Ile Ile Thr Leu Glu Asp
                245                 250                 255

Ser Ser Gly Asn Leu Leu Gly Arg Asp Ser Phe Glu Val Arg Val Cys
            260                 265                 270

Ala Cys Pro Gly Arg Asp Arg Arg Thr Glu Glu Glu Asn Phe Arg Lys
```

```
            275                 280                 285
Lys Glu Val Leu Cys Pro Glu Leu Pro Pro Gly Ser Ala Lys Arg Ala
            290                 295                 300

Leu Pro Thr Cys Thr Ser Ala Ser Pro Gln Lys Lys Lys Pro Leu
305                 310                 315                 320

Asp Gly Glu Tyr Phe Thr Leu Lys Ile Arg Gly Arg Lys Arg Phe Glu
                325                 330                 335

Met Phe Arg Glu Leu Asn Glu Ala Leu Glu Leu Lys Asp Ala His Ala
                340                 345                 350

Thr Glu Glu Ser Gly Asp Ser Arg Ala His Ser Ser Tyr Leu Lys Thr
                355                 360                 365

Lys Lys Gly Gln Ser Thr Ser Arg His Lys Lys Thr Met Val Lys Lys
                370                 375                 380

Val Gly Pro Asp Ser Asp
385                 390

<210> SEQ ID NO 13
<211> LENGTH: 354
<212> TYPE: PRT
<213> ORGANISM: homo sapiens
<220> FEATURE:
<221> NAME/KEY: MISC_FEATURE
<223> OTHER INFORMATION: amino acid sequence of p53 delta 40

<400> SEQUENCE: 13

Met Asp Asp Leu Met Leu Ser Pro Asp Asp Ile Glu Gln Trp Phe Thr
1               5                   10                  15

Glu Asp Pro Gly Pro Asp Glu Ala Pro Arg Met Pro Glu Ala Ala Pro
                20                  25                  30

Pro Val Ala Pro Ala Pro Ala Ala Pro Thr Pro Ala Ala Pro Ala Pro
            35                  40                  45

Ala Pro Ser Trp Pro Leu Ser Ser Ser Val Pro Ser Gln Lys Thr Tyr
        50                  55                  60

Gln Gly Ser Tyr Gly Phe Arg Leu Gly Phe Leu His Ser Gly Thr Ala
65                  70                  75                  80

Lys Ser Val Thr Cys Thr Tyr Ser Pro Ala Leu Asn Lys Met Phe Cys
                85                  90                  95

Gln Leu Ala Lys Thr Cys Pro Val Gln Leu Trp Val Asp Ser Thr Pro
                100                 105                 110

Pro Pro Gly Thr Arg Val Arg Ala Met Ala Ile Tyr Lys Gln Ser Gln
            115                 120                 125

His Met Thr Glu Val Val Arg Arg Cys Pro His His Glu Arg Cys Ser
130                 135                 140

Asp Ser Asp Gly Leu Ala Pro Pro Gln His Leu Ile Arg Val Glu Gly
145                 150                 155                 160

Asn Leu Arg Val Glu Tyr Leu Asp Asp Arg Asn Thr Phe Arg His Ser
                165                 170                 175

Val Val Val Pro Tyr Glu Pro Pro Glu Val Gly Ser Asp Cys Thr Thr
                180                 185                 190

Ile His Tyr Asn Tyr Met Cys Asn Ser Ser Cys Met Gly Gly Met Asn
            195                 200                 205

Arg Arg Pro Ile Leu Thr Ile Ile Thr Leu Glu Asp Ser Ser Gly Asn
        210                 215                 220

Leu Leu Gly Arg Asn Ser Phe Glu Val Arg Val Cys Ala Cys Pro Gly
225                 230                 235                 240
```

-continued

```
Arg Asp Arg Arg Thr Glu Glu Glu Asn Leu Arg Lys Lys Gly Glu Pro
            245                 250                 255

His His Glu Leu Pro Pro Gly Ser Thr Lys Arg Ala Leu Pro Asn Asn
        260                 265                 270

Thr Ser Ser Ser Pro Gln Pro Lys Lys Lys Pro Leu Asp Gly Glu Tyr
    275                 280                 285

Phe Thr Leu Gln Ile Arg Gly Arg Glu Arg Phe Glu Met Phe Arg Glu
290                 295                 300

Leu Asn Glu Ala Leu Glu Leu Lys Asp Ala Gln Ala Gly Lys Glu Pro
305                 310                 315                 320

Gly Gly Ser Arg Ala His Ser Ser His Leu Lys Ser Lys Lys Gly Gln
                325                 330                 335

Ser Thr Ser Arg His Lys Lys Leu Met Phe Lys Thr Glu Gly Pro Asp
            340                 345                 350

Ser Asp

<210> SEQ ID NO 14
<211> LENGTH: 261
<212> TYPE: PRT
<213> ORGANISM: homo sapiens
<220> FEATURE:
<221> NAME/KEY: MISC_FEATURE
<223> OTHER INFORMATION: amino acid sequence of p53 delta 133

<400> SEQUENCE: 14

Met Phe Cys Gln Leu Ala Lys Thr Cys Pro Val Gln Leu Trp Val Asp
1               5                   10                  15

Ser Thr Pro Pro Pro Gly Thr Arg Val Arg Ala Met Ala Ile Tyr Lys
            20                  25                  30

Gln Ser Gln His Met Thr Glu Val Val Arg Arg Cys Pro His His Glu
        35                  40                  45

Arg Cys Ser Asp Ser Asp Gly Leu Ala Pro Pro Gln His Leu Ile Arg
    50                  55                  60

Val Glu Gly Asn Leu Arg Val Glu Tyr Leu Asp Asp Arg Asn Thr Phe
65                  70                  75                  80

Arg His Ser Val Val Pro Tyr Glu Pro Pro Glu Val Gly Ser Asp
                85                  90                  95

Cys Thr Thr Ile His Tyr Asn Tyr Met Cys Asn Ser Ser Cys Met Gly
            100                 105                 110

Gly Met Asn Arg Arg Pro Ile Leu Thr Ile Ile Thr Leu Glu Asp Ser
        115                 120                 125

Ser Gly Asn Leu Leu Gly Arg Asn Ser Phe Glu Val Arg Val Cys Ala
    130                 135                 140

Cys Pro Gly Arg Asp Arg Arg Thr Glu Glu Glu Asn Leu Arg Lys Lys
145                 150                 155                 160

Gly Glu Pro His His Glu Leu Pro Pro Gly Ser Thr Lys Arg Ala Leu
                165                 170                 175

Pro Asn Asn Thr Ser Ser Ser Pro Gln Pro Lys Lys Lys Pro Leu Asp
            180                 185                 190

Gly Glu Tyr Phe Thr Leu Gln Ile Arg Gly Arg Glu Arg Phe Glu Met
        195                 200                 205

Phe Arg Glu Leu Asn Glu Ala Leu Glu Leu Lys Asp Ala Gln Ala Gly
    210                 215                 220

Lys Glu Pro Gly Gly Ser Arg Ala His Ser Ser His Leu Lys Ser Lys
225                 230                 235                 240
```

```
Lys Gly Gln Ser Thr Ser Arg His Lys Lys Leu Met Phe Lys Thr Glu
                    245                 250                 255

Gly Pro Asp Ser Asp
            260
```

<210> SEQ ID NO 15
<211> LENGTH: 341
<212> TYPE: PRT
<213> ORGANISM: homo sapiens
<220> FEATURE:
<221> NAME/KEY: MISC_FEATURE
<223> OTHER INFORMATION: amino acid sequence of p53 beta

<400> SEQUENCE: 15

```
Met Glu Glu Pro Gln Ser Asp Pro Ser Val Glu Pro Pro Leu Ser Gln
1               5                   10                  15

Glu Thr Phe Ser Asp Leu Trp Lys Leu Leu Pro Glu Asn Asn Val Leu
                20                  25                  30

Ser Pro Leu Pro Ser Gln Ala Met Asp Asp Leu Met Leu Ser Pro Asp
            35                  40                  45

Asp Ile Glu Gln Trp Phe Thr Glu Asp Pro Gly Pro Asp Glu Ala Pro
    50                  55                  60

Arg Met Pro Glu Ala Ala Pro Arg Val Ala Pro Ala Pro Ala Ala Pro
65                  70                  75                  80

Thr Pro Ala Ala Pro Ala Pro Ala Pro Ser Trp Pro Leu Ser Ser Ser
                85                  90                  95

Val Pro Ser Gln Lys Thr Tyr Gln Gly Ser Tyr Gly Phe Arg Leu Gly
                100                 105                 110

Phe Leu His Ser Gly Thr Ala Lys Ser Val Thr Cys Thr Tyr Ser Pro
            115                 120                 125

Ala Leu Asn Lys Met Phe Cys Gln Leu Ala Lys Thr Cys Pro Val Gln
    130                 135                 140

Leu Trp Val Asp Ser Thr Pro Pro Gly Thr Arg Val Arg Ala Met
145                 150                 155                 160

Ala Ile Tyr Lys Gln Ser Gln His Met Thr Glu Val Val Arg Arg Cys
                165                 170                 175

Pro His His Glu Arg Cys Ser Asp Ser Asp Gly Leu Ala Pro Pro Gln
            180                 185                 190

His Leu Ile Arg Val Glu Gly Asn Leu Arg Val Glu Tyr Leu Asp Asp
    195                 200                 205

Arg Asn Thr Phe Arg His Ser Val Val Val Pro Tyr Glu Pro Pro Glu
210                 215                 220

Val Gly Ser Asp Cys Thr Thr Ile His Tyr Asn Tyr Met Cys Asn Ser
225                 230                 235                 240

Ser Cys Met Gly Gly Met Asn Arg Arg Pro Ile Leu Thr Ile Ile Thr
                245                 250                 255

Leu Glu Asp Ser Ser Gly Asn Leu Leu Gly Arg Asn Ser Phe Glu Val
            260                 265                 270

Arg Val Cys Ala Cys Pro Gly Arg Asp Arg Arg Thr Glu Glu Glu Asn
    275                 280                 285

Leu Arg Lys Lys Gly Glu Pro His His Glu Leu Pro Pro Gly Ser Thr
290                 295                 300

Lys Arg Ala Leu Pro Asn Asn Thr Ser Ser Pro Gln Pro Lys Lys
305                 310                 315                 320

Lys Pro Leu Asp Gly Glu Tyr Phe Thr Leu Gln Asp Gln Thr Ser Phe
                325                 330                 335
```

Gln Lys Glu Asn Cys
            340

<210> SEQ ID NO 16
<211> LENGTH: 346
<212> TYPE: PRT
<213> ORGANISM: homo sapiens
<220> FEATURE:
<221> NAME/KEY: MISC_FEATURE
<223> OTHER INFORMATION: amino acid sequence of p53 gamma

<400> SEQUENCE: 16

Met Glu Glu Pro Gln Ser Asp Pro Ser Val Glu Pro Pro Leu Ser Gln
1               5                   10                  15

Glu Thr Phe Ser Asp Leu Trp Lys Leu Leu Pro Glu Asn Asn Val Leu
            20                  25                  30

Ser Pro Leu Pro Ser Gln Ala Met Asp Asp Leu Met Leu Ser Pro Asp
        35                  40                  45

Asp Ile Glu Gln Trp Phe Thr Glu Asp Pro Gly Pro Asp Glu Ala Pro
    50                  55                  60

Arg Met Pro Glu Ala Ala Pro Pro Val Ala Pro Ala Pro Ala Ala Pro
65                  70                  75                  80

Thr Pro Ala Ala Pro Ala Pro Ala Pro Ser Trp Pro Leu Ser Ser Ser
            85                  90                  95

Val Pro Ser Gln Lys Thr Tyr Gln Gly Ser Tyr Gly Phe Arg Leu Gly
            100                 105                 110

Phe Leu His Ser Gly Thr Ala Lys Ser Val Thr Cys Thr Tyr Ser Pro
        115                 120                 125

Ala Leu Asn Lys Met Phe Cys Gln Leu Ala Lys Thr Cys Pro Val Gln
    130                 135                 140

Leu Trp Val Asp Ser Thr Pro Pro Gly Thr Arg Val Arg Ala Met
145                 150                 155                 160

Ala Ile Tyr Lys Gln Ser Gln His Met Thr Glu Val Val Arg Arg Cys
                165                 170                 175

Pro His His Glu Arg Cys Ser Asp Ser Asp Gly Leu Ala Pro Pro Gln
            180                 185                 190

His Leu Ile Arg Val Glu Gly Asn Leu Arg Val Glu Tyr Leu Asp Asp
        195                 200                 205

Arg Asn Thr Phe Arg His Ser Val Val Val Pro Tyr Glu Pro Pro Glu
    210                 215                 220

Val Gly Ser Asp Cys Thr Thr Ile His Tyr Asn Tyr Met Cys Asn Ser
225                 230                 235                 240

Ser Cys Met Gly Gly Met Asn Arg Arg Pro Ile Leu Thr Ile Ile Thr
                245                 250                 255

Leu Glu Asp Ser Ser Gly Asn Leu Leu Gly Arg Asn Ser Phe Glu Val
            260                 265                 270

Arg Val Cys Ala Cys Pro Gly Arg Asp Arg Arg Thr Glu Glu Glu Asn
        275                 280                 285

Leu Arg Lys Lys Gly Glu Pro His His Glu Leu Pro Pro Gly Ser Thr
    290                 295                 300

Lys Arg Ala Leu Pro Asn Asn Thr Ser Ser Ser Pro Gln Pro Lys Lys
305                 310                 315                 320

Lys Pro Leu Asp Gly Glu Tyr Phe Thr Leu Gln Met Leu Leu Asp Leu
                325                 330                 335

Arg Trp Cys Tyr Phe Leu Ile Asn Ser Ser

<210> SEQ ID NO 17
<211> LENGTH: 19
<212> TYPE: RNA
<213> ORGANISM: artificial
<220> FEATURE:
<223> OTHER INFORMATION: siRNA anti-p53

<400> SEQUENCE: 17
gacuccagug guaaucuac                                                  19

<210> SEQ ID NO 18
<211> LENGTH: 19
<212> TYPE: RNA
<213> ORGANISM: artificial
<220> FEATURE:
<223> OTHER INFORMATION: siRNA anti p53

<400> SEQUENCE: 18
gcaugaaccg gaggcccau                                                  19

<210> SEQ ID NO 19
<211> LENGTH: 25
<212> TYPE: RNA
<213> ORGANISM: artificial
<220> FEATURE:
<223> OTHER INFORMATION: siRNA anti-delta 133TP53

<400> SEQUENCE: 19
uguucacuug ugcccugacu uucaa                                           25

<210> SEQ ID NO 20
<211> LENGTH: 19
<212> TYPE: RNA
<213> ORGANISM: artificial
<220> FEATURE:
<223> OTHER INFORMATION: siRNA anti-delta 133TP53

<400> SEQUENCE: 20
cuugugcccu gacuuucaa                                                  19

<210> SEQ ID NO 21
<211> LENGTH: 18
<212> TYPE: RNA
<213> ORGANISM: artificial
<220> FEATURE:
<223> OTHER INFORMATION: siRNA anti-ATM

<400> SEQUENCE: 21
ugaaguccau ugcuaauc                                                   18

<210> SEQ ID NO 22
<211> LENGTH: 19
<212> TYPE: RNA
<213> ORGANISM: artificial
<220> FEATURE:
<223> OTHER INFORMATION: siRNA anti-ATM

<400> SEQUENCE: 22
aacauacuac ucaaagaca                                                  19

<210> SEQ ID NO 23
<211> LENGTH: 19
<212> TYPE: RNA
<213> ORGANISM: artificial

```
<220> FEATURE:
<223> OTHER INFORMATION: siRNA antiATR

<400> SEQUENCE: 23
ccuccgugau guugcuuga                                                19

<210> SEQ ID NO 24
<211> LENGTH: 19
<212> TYPE: RNA
<213> ORGANISM: artificial
<220> FEATURE:
<223> OTHER INFORMATION: siRNA anti-ATR

<400> SEQUENCE: 24
gccaagacaa auucugugu                                                19

<210> SEQ ID NO 25
<211> LENGTH: 19
<212> TYPE: RNA
<213> ORGANISM: artificial
<220> FEATURE:
<223> OTHER INFORMATION: siRNA anti-BRCA1

<400> SEQUENCE: 25
gcaaccuguc uccacaaag                                                19

<210> SEQ ID NO 26
<211> LENGTH: 19
<212> TYPE: RNA
<213> ORGANISM: artificial
<220> FEATURE:
<223> OTHER INFORMATION: siRNA anti-BRCA1

<400> SEQUENCE: 26
ugccaaagua gcuaaugua                                                19

<210> SEQ ID NO 27
<211> LENGTH: 19
<212> TYPE: RNA
<213> ORGANISM: artificial
<220> FEATURE:
<223> OTHER INFORMATION: siRNA anti-BRCA2

<400> SEQUENCE: 27
cugagcaagc cucagucaa                                                19

<210> SEQ ID NO 28
<211> LENGTH: 19
<212> TYPE: RNA
<213> ORGANISM: artificial
<220> FEATURE:
<223> OTHER INFORMATION: siRNA anti-BRCA2

<400> SEQUENCE: 28
caacaauuac gaaccaaac                                                19

<210> SEQ ID NO 29
<211> LENGTH: 19
<212> TYPE: RNA
<213> ORGANISM: artificial
<220> FEATURE:
<223> OTHER INFORMATION: siRNA anti-LKB1

<400> SEQUENCE: 29
ggacugacgu guagaacaa                                                19
```

```
<210> SEQ ID NO 30
<211> LENGTH: 19
<212> TYPE: RNA
<213> ORGANISM: artificial
<220> FEATURE:
<223> OTHER INFORMATION: siRNA anti-LKB1

<400> SEQUENCE: 30
guccuuacgg caaggugaa                                                      19

<210> SEQ ID NO 31
<211> LENGTH: 19
<212> TYPE: RNA
<213> ORGANISM: artificial
<220> FEATURE:
<223> OTHER INFORMATION: siRNA anti-p15INK4b

<400> SEQUENCE: 31
cucagugcaa acgccuaga                                                      19

<210> SEQ ID NO 32
<211> LENGTH: 21
<212> TYPE: RNA
<213> ORGANISM: artificial
<220> FEATURE:
<223> OTHER INFORMATION: siRNA anti-p15INK4b

<400> SEQUENCE: 32
aacucagugc aaacgccuag a                                                   21

<210> SEQ ID NO 33
<211> LENGTH: 20
<212> TYPE: RNA
<213> ORGANISM: artificial
<220> FEATURE:
<223> OTHER INFORMATION: siRNA anti-p63

<400> SEQUENCE: 33
ccaugagcug agccgugaau                                                     20

<210> SEQ ID NO 34
<211> LENGTH: 19
<212> TYPE: RNA
<213> ORGANISM: artificial
<220> FEATURE:
<223> OTHER INFORMATION: siRNA anti-p63

<400> SEQUENCE: 34
agcagcaagu uucggacag                                                      19

<210> SEQ ID NO 35
<211> LENGTH: 19
<212> TYPE: RNA
<213> ORGANISM: artificial
<220> FEATURE:
<223> OTHER INFORMATION: siRNA anti-p73

<400> SEQUENCE: 35
ccacgagcuc gggagggac                                                      19

<210> SEQ ID NO 36
<211> LENGTH: 19
<212> TYPE: RNA
<213> ORGANISM: artificial
<220> FEATURE:
<223> OTHER INFORMATION: siRNA anti-p73
```

<400> SEQUENCE: 36
acguccaugc uggaauccg                                                   19

<210> SEQ ID NO 37
<211> LENGTH: 19
<212> TYPE: RNA
<213> ORGANISM: artificial
<220> FEATURE:
<223> OTHER INFORMATION: siRNA anti-par4

<400> SEQUENCE: 37
guggguuccc uagauauaa                                                   19

<210> SEQ ID NO 38
<211> LENGTH: 19
<212> TYPE: RNA
<213> ORGANISM: artificial
<220> FEATURE:
<223> OTHER INFORMATION: siRNA anti-par4

<400> SEQUENCE: 38
cagccguuug aauauauuu                                                   19

<210> SEQ ID NO 39
<211> LENGTH: 19
<212> TYPE: RNA
<213> ORGANISM: artificial
<220> FEATURE:
<223> OTHER INFORMATION: siRNA anti PTEN

<400> SEQUENCE: 39
gucagaggcg cuaugugua                                                   19

<210> SEQ ID NO 40
<211> LENGTH: 19
<212> TYPE: RNA
<213> ORGANISM: artificial
<220> FEATURE:
<223> OTHER INFORMATION: siRNA anti-PTEN

<400> SEQUENCE: 40
caccacagcu agaacuuau                                                   19

<210> SEQ ID NO 41
<211> LENGTH: 19
<212> TYPE: RNA
<213> ORGANISM: artificial
<220> FEATURE:
<223> OTHER INFORMATION: siRNA anti-Rb

<400> SEQUENCE: 41
gaaaggacau gugaacuua                                                   19

<210> SEQ ID NO 42
<211> LENGTH: 19
<212> TYPE: RNA
<213> ORGANISM: artificial
<220> FEATURE:
<223> OTHER INFORMATION: siRNA anti-Rb

<400> SEQUENCE: 42
cgaaaucagu guccauaaa                                                   19

<210> SEQ ID NO 43

```
<211> LENGTH: 19
<212> TYPE: RNA
<213> ORGANISM: artificial
<220> FEATURE:
<223> OTHER INFORMATION: siRNA anti-p21WAF1

<400> SEQUENCE: 43
cuucgacuuu gucaccgag                                                     19

<210> SEQ ID NO 44
<211> LENGTH: 21
<212> TYPE: RNA
<213> ORGANISM: artificial
<220> FEATURE:
<223> OTHER INFORMATION: siRNA anti-p21WAF1

<400> SEQUENCE: 44
caguuugugu gucuuaauua u                                                  21

<210> SEQ ID NO 45
<211> LENGTH: 19
<212> TYPE: RNA
<213> ORGANISM: artificial
<220> FEATURE:
<223> OTHER INFORMATION: siRNA anti-beclin1

<400> SEQUENCE: 45
gauugaagac acaggaggc                                                     19

<210> SEQ ID NO 46
<211> LENGTH: 25
<212> TYPE: RNA
<213> ORGANISM: artificial
<220> FEATURE:
<223> OTHER INFORMATION: siRNA anti-beclin 1

<400> SEQUENCE: 46
ccacucugug aggaaugcac agaua                                              25

<210> SEQ ID NO 47
<211> LENGTH: 19
<212> TYPE: RNA
<213> ORGANISM: artificial
<220> FEATURE:
<223> OTHER INFORMATION: siRNA anti-FOXO1

<400> SEQUENCE: 47
gcccuggcuc ucacagcaa                                                     19

<210> SEQ ID NO 48
<211> LENGTH: 19
<212> TYPE: RNA
<213> ORGANISM: artificial
<220> FEATURE:
<223> OTHER INFORMATION: siRNA anti-FOXO1

<400> SEQUENCE: 48
ccgcgcaaga gcagcucgu                                                     19

<210> SEQ ID NO 49
<211> LENGTH: 19
<212> TYPE: RNA
<213> ORGANISM: artificial
<220> FEATURE:
<223> OTHER INFORMATION: siRNA anti-FOXO3

<400> SEQUENCE: 49
```

```
gggcgacagc aacagcucu                                    19
```

<210> SEQ ID NO 50
<211> LENGTH: 19
<212> TYPE: RNA
<213> ORGANISM: artificial
<220> FEATURE:
<223> OTHER INFORMATION: siRNA anti-FOXO3

<400> SEQUENCE: 50

```
ggaugacguc caggaugau                                    19
```

<210> SEQ ID NO 51
<211> LENGTH: 19
<212> TYPE: RNA
<213> ORGANISM: artificial
<220> FEATURE:
<223> OTHER INFORMATION: siRNA anti-FOXO4

<400> SEQUENCE: 51

```
cccgaccaga gaucgcuaa                                    19
```

<210> SEQ ID NO 52
<211> LENGTH: 19
<212> TYPE: RNA
<213> ORGANISM: artificial
<220> FEATURE:
<223> OTHER INFORMATION: siRNA anti-FOXO4

<400> SEQUENCE: 52

```
ggacaagggu gacagcaac                                    19
```

<210> SEQ ID NO 53
<211> LENGTH: 19
<212> TYPE: RNA
<213> ORGANISM: artificial
<220> FEATURE:
<223> OTHER INFORMATION: siRNA antiP2Y2R

<400> SEQUENCE: 53

```
ggauagaaga uguguugggg                                   19
```

<210> SEQ ID NO 54
<211> LENGTH: 19
<212> TYPE: RNA
<213> ORGANISM: artificial
<220> FEATURE:
<223> OTHER INFORMATION: siRNA anti-P2Y2R

<400> SEQUENCE: 54

```
ggcuguaacu uauacuaaa                                    19
```

<210> SEQ ID NO 55
<211> LENGTH: 19
<212> TYPE: RNA
<213> ORGANISM: artificial
<220> FEATURE:
<223> OTHER INFORMATION: siRNA control

<400> SEQUENCE: 55

```
gccgguaugc cgguuaagu                                    19
```